(12) United States Patent  
Fulghum, Jr.

(10) Patent No.: US 7,404,929 B2  
(45) Date of Patent: Jul. 29, 2008

(54) SPECTROSCOPIC DIAGNOSTIC METHODS AND SYSTEM BASED ON SCATTERING OF POLARIZED LIGHT

(75) Inventor: Stephen F. Fulghum, Jr., Marblehead, MA (US)

(73) Assignee: Newton Laboratories, Inc., Belmont, MA (US)

( * ) Notice: Subject to any disclaimer, the term of this patent is extended or adjusted under 35 U.S.C. 154(b) by 414 days.

(21) Appl. No.: 10/347,134

(22) Filed: Jan. 17, 2003

(65) Prior Publication Data

US 2003/0232445 A1 Dec. 18, 2003

Related U.S. Application Data

(60) Provisional application No. 60/349,958, filed on Jan. 18, 2002.

(51) Int. Cl.  
*G01N 21/00* (2006.01)

(52) U.S. Cl. .................. 422/82.05; 422/82.09

(58) Field of Classification Search .................. None  
See application file for complete search history.

(56) References Cited

U.S. PATENT DOCUMENTS

| | | | |
|---|---|---|---|
| 4,497,577 A | 2/1985 | Sato et al. | 356/336 |
| 4,541,719 A | 9/1985 | Wyatt | 356/343 |
| 4,768,879 A | 9/1988 | McLachlan et al. | 356/301 |
| 5,151,909 A * | 9/1992 | Davenport et al. | 372/22 |
| 5,303,026 A | 4/1994 | Strobl et al. | 356/318 |
| 5,636,637 A | 6/1997 | Guiolet et al. | 128/665 |
| 5,940,425 A | 8/1999 | Lasser et al. | 372/72 |
| 6,006,001 A | 12/1999 | Alfano et al. | 385/115 |
| 6,028,622 A | 2/2000 | Suzuki | 348/65 |
| 6,212,425 B1 | 4/2001 | Irion et al. | 600/476 |
| 6,217,510 B1 | 4/2001 | Ozawa et al. | 600/129 |
| 6,293,911 B1 | 9/2001 | Imaizumi et al. | 600/160 |
| 6,422,994 B1 | 7/2002 | Kaneko et al. | 600/160 |
| 6,462,770 B1 | 10/2002 | Cline et al. | 348/65 |
| 2002/0007123 A1* | 1/2002 | Balas | 600/476 |
| 2002/0035330 A1 | 3/2002 | Cline et al. | 600/476 |

(Continued)

FOREIGN PATENT DOCUMENTS

DE 227044 9/1985

(Continued)

OTHER PUBLICATIONS

"Diode Lasers", http://repairfaq.ece.drexel.edu/sam/laserdio.htm.*

(Continued)

*Primary Examiner*—Yelena G Gakh  
(74) *Attorney, Agent, or Firm*—Weingarten, Schurgin, Gagnebin & Lebovici LLP

(57) ABSTRACT

The present invention provides systems and methods for the determination of the physical characteristics of a structured superficial layer of material using light scattering spectroscopy. The light scattering spectroscopy system comprises optical probes that can be used with existing endoscopes without modification to the endoscope itself. The system uses a combination of optical and computational methods to detect physical characteristics such as the size distribution of cell nuclei in epithelial layers of organs. The light scattering spectroscopy system can be used alone, or in conjunction with other techniques, such as fluorescence spectroscopy and reflected light spectroscopy.

39 Claims, 40 Drawing Sheets

U.S. PATENT DOCUMENTS

| | | | |
|---|---|---|---|
| 2002/0049366 A1 | 4/2002 | Kehr | 600/172 |
| 2002/0077677 A1 | 6/2002 | Beck et al. | 607/88 |

FOREIGN PATENT DOCUMENTS

| | | |
|---|---|---|
| EP | 0 590 268 | 4/1994 |
| JP | 173020 | 11/1984 |
| JP | 7250812 A | 10/1995 |
| JP | 8224209 A | 9/1996 |
| JP | 8224210 A | 9/1996 |
| JP | 8252218 A | 10/1996 |
| JP | 200097859 A | 4/2000 |
| JP | 2002095624 A | 4/2002 |
| WO | WO 96/05693 | 2/1996 |
| WO | WO 96/42006 | 12/1996 |
| WO | WO 00/19889 | 4/2000 |
| WO | WO 00/43750 | 7/2000 |
| WO | WO 01/34031 | 5/2001 |
| WO | WO 02/07587 | 1/2002 |

OTHER PUBLICATIONS

Li et al. "New Thin Film Polarizing Beamsplitter", 1998, http://www.sspectra.com/designs/ftr_polar.html.*

* cited by examiner

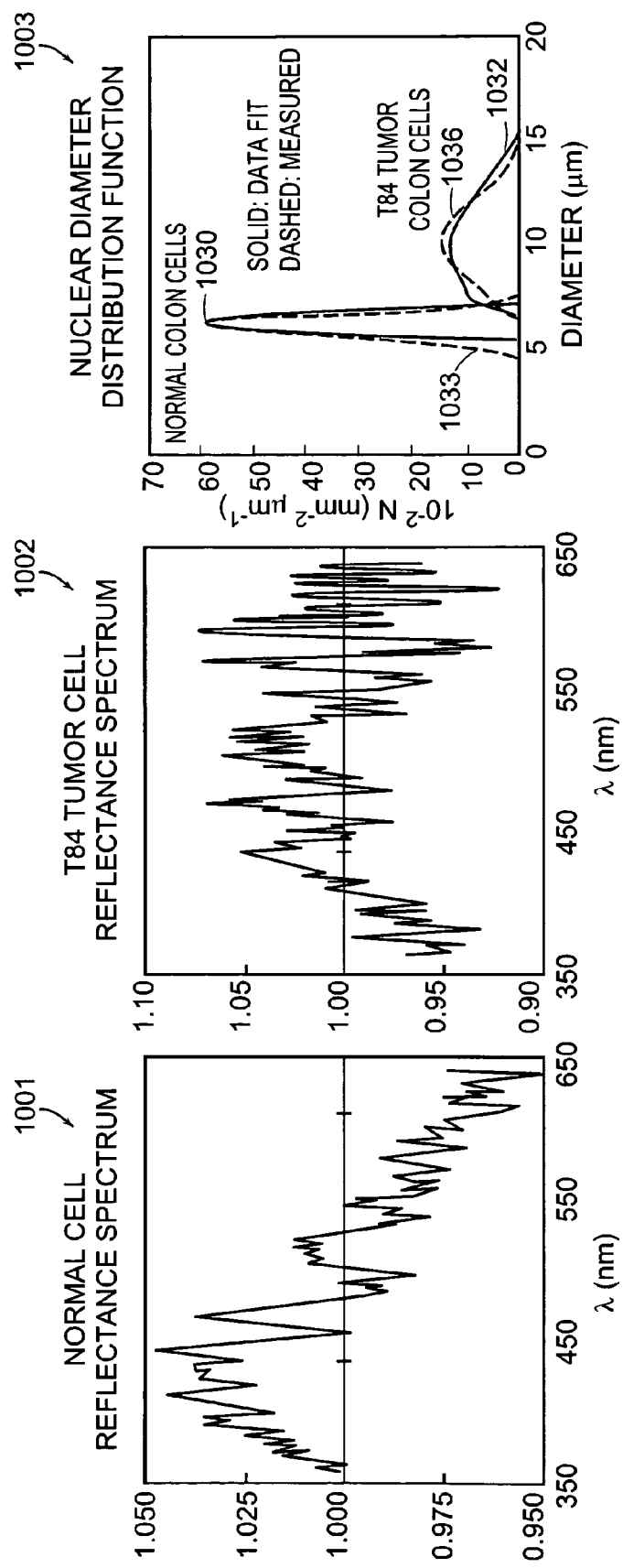

DIFFUSE BACKSCATTER

TISSUE TRANSMISSION

SPECTROSCOPIC DIAGNOSTIC METHODS AND SYSTEM BASED ON SCATTERING OF POLARIZED LIGHT

CROSS REFERENCES TO RELATED APPLICATIONS

The present application claims the benefit of and priority to U.S. Provisional Application No. 60/349,958, filed Jan. 18, 2002. The entire contents of the above application is incorporated herein by reference in its entirety.

BACKGROUND OF THE INVENTION

It is often necessary to obtain quantitative information that characterizes the features of a surface layer of microscopic objects relatively free from the influence of underlying structures. Light-scattering spectroscopy (LSS) is one technique that can provide the desired information. One such application is monitoring the precancerous condition of the cells in the epithelial layer that cover surfaces or body organs.

The ability to measure quantitative changes in intracellular structures in situ provides an opportunity for early diagnosis of cancer or precancerous lesions. More than 90% of all cancers are epithelial in origin. Most epithelial cancers have a well-defined precancerous stage characterized by nuclear atypia and dysplasia. Lesions detected at this stage can potentially be eradicated with early diagnosis. However, many forms of atypia and dysplasia are flat and not visually observable. Thus, surveillance for invisible dysplasia employs random biopsy, followed by microscopic examination of the biopsy material by a pathologist. However, usually only a small fraction of the epithelial surface at risk for dysplasia can be sampled in this way, potentially resulting in a high sampling error.

Body surfaces are covered with a thin layer of epithelial tissue. The thickness of the epithelium in various organs ranges from less than 10 µm in simple squamous epithelia (having single layer of epithelial cells) to several hundred µm in stratified epithelia that have multiple layers of epithelial cells. Beneath all epithelia are variable layers of the supporting components including relatively hypocellular connective tissues, inflammatory cells, and neurovascular structures.

For example, in hollow organs, such as the gastrointestinal tract, the epithelial cell layer is from 20 µm to 300 µm thick, depending on the part of the tract. Below the epithelium is a relatively acellular and highly vascular loose connective tissue, the lamina propria, that can be up to 500 µm in thickness containing a network of collagen and elastic fibers, and a variety of white blood cell types. Beneath the lamina propria there is a muscular layer, the muscularis mucosae, (up to 400 µm thick) and below that, another layer, about 400-600 µm thick, of moderately dense connective tissue containing many small blood vessels and abundant collagen and elastic fibers called the submucosa. The overall thickness of those layers is about 1 mm. Since a characteristic penetration depth of optical radiation into biological tissue does not usually exceed 1 mm, for a preferred embodiment it is sufficient to limit measurements of tissue by those layers.

Light traversing the epithelial layer can be scattered by cell organelles of various sizes, such as mitochondria and nuclei, which have refractive indices higher than that of the surrounding cytoplasm. Elastic scattering of light by cells is due to a variety of intracellular organelles, including mitochondria, a variety of endosomes and other cytoplasmic vesicles, nucleoli, and nuclei. The smaller organelles are responsible for large angle scattering, whereas the nucleus contributes to scattering at small angles.

The cell nuclei are appreciably larger than the optical wavelength (typically 5-10 µm compared to 0.5 µm). They predominantly scatter light in the forward direction, and there is appreciable scattering in the backward direction, as well. The backscattered light has a wavelength-dependent oscillatory component. The periodicity of this component increases with nuclear size, and its amplitude is related to cellularity or the population density of the epithelial nuclei. By analyzing the frequency and amplitude of this oscillatory component, the size distribution and density of epithelial nuclei can be extracted.

In order to detect changes in epithelial cell nuclei associated with dysplasia, the light reflected from the epithelial layer must be distinguished from the light reflected from the underlying tissue. Since, as noted above, the penetration depth in tissue substantially exceeds the epithelial thickness, the backscattered light from epithelial nuclei is ordinarily very small in amplitude, and it is easily masked by the diffuse background of light reflected from the underlying tissue. This diffuse background reflected light must be removed in order to analyze the backscattered component.

Previous approaches have sought to remove the diffuse background reflected light by modeling the general spectral features of the background. However, this approach must be specifically adapted to each different type of tissue studied, and its accuracy is theory dependent. More robust methods of removing or significantly reducing the diffuse component of the scattered light are needed to extend the use of LSS to various medical applications.

The various forms of epithelial dysplasia exhibit some common morphological changes on microscopic examination, the most prominent of which relate to the nuclear morphology. The nuclei become enlarged, pleomorphic (irregular in contour and size distribution), "crowded" (they occupy more of the tissue volume), and hyperchromatic (they stain more intensely with nuclear stains). The diameter of non-dysplastic cell nuclei is typically 5-10 µm, whereas dysplastic nuclei can be as large as 20 µm across.

Epithelial cell nuclei can be modeled as transparent spheroids that are large in comparison to the wavelength of visible light (0.4-0.8 µm), and whose refractive index is higher than that of the surrounding cytoplasm because of their chromatin content. The spectrum of light backscattered by these particles contains a component that varies characteristically with wavelength, with this variation depending on particle size and refractive index.

The light scattering from epithelial cell nuclei can be isolated using polarized light. It is known that polarized light loses its polarization when traversing a turbid medium such as biological tissue. In contrast, polarized light scattered backward after a single scattering event does not lose its polarization. This property of polarized light has been used previously to image surface and near surface biological tissues. Thus, by subtracting the unpolarized spectral component of the scattered light, the portion of light scattering due to backscattering from epithelial cell nuclei can be readily distinguished. The difference spectrum can be further analyzed to extract the size distribution of the nuclei, their population density, and their refractive index relative to the surrounding medium.

Although many epithelial cancers are treatable provided they are diagnosed in a pre-invasive state, early lesions are often almost impossible to detect. Before they become invasive, at stages known as dysplasia and carcinoma in situ, early cancer cells alter the epithelial cell architecture. In particular, the nuclei become enlarged, crowded and hyperchromatic, that is, they stain abnormally dark with a contrast dye. These preinvasive signs have been detectable by histological examination of biopsy specimens, but no reliable optical technique to diagnose dysplasia in-vivo is available. Light-scattering spectroscopy (LSS) can provide a biopsy-free means to measure the size distribution and chromatin content of epithelial-cell nuclei as an indictor of pre-invasive neoplasia.

For a collection of nuclei of different sizes, the light-scattering signal is a superposition of these variations, enabling the nuclear-size distribution and refractive index to be determined from the spectrum of light backscattered from the nuclei. Once the nuclear-size distribution and refractive index are known, quantitative measures of nuclear enlargement, crowding and hyperchromasia can be obtained.

Barrett's esophagus is a pre-cancerous condition arising in approximately 10-20% of patients with chronic reflux of stomach contents into the esophagus. People who develop Barrett's esophagus may have symptoms of heartburn, indigestion, difficulty swallowing solid foods, or nocturnal regurgitation that awakens them from sleep. Patients with Barrett's esophagus have an increased risk of developing esophageal adenocarcinoma, the most rapidly increasing cancer in the United States.

Adenocarcinoma of the esophagus arises in metaplastic columnar epithelial cells in the esophagus, as a complication of such chronic gastrointestinal reflux. In this condition, the distal squamous epithelium is replaced by columnar epithelium consisting of a one cell layer which resembles that found in the intestines. Barrett's esophagus is frequently associated with dysplasia, which later can progress to cancer. Trials of endoscopic surveillance of patients with Barrett's esophagus have not resulted in a reduction of esophageal cancer mortality. The most likely explanation is that dysplasia occurring in the esophagus cannot be seen with standard endoscopic imaging and sporadic biopsy sampling is necessary. This procedure can sample only about 0.3% of the tissue at risk. Thus, there is tremendous potential for sampling error.

The application of optical techniques to diagnose dysplasia in Barrett's esophagus is limited by the fact that the primary alterations in the tissue occur in the epithelium which is one cell thick (~20-30 μm) while fluorescence or reflectance spectra are mostly formed in deeper tissue layers. One of the most prominent features of a dysplastic epithelium is the presence of enlarged, hyperchromatic, and crowded nuclei. In fact, these changes in nuclear size and spatial distribution are the main markers used by a pathologist to diagnose a tissue specimen as being dysplastic. No significant changes are observed in other tissue layers. Unfortunately, epithelium does not contain strong absorbers or fluorophores, and the thickness of the epithelium is relatively small and thus negligible. These make epithelium diagnosis in Barrett's esophagus a difficult problem. In such cases, LSS can provide a biopsy-free means to measure the size distribution and chromatin content of epithelial-cell nuclei as an indictor of pre-invasive neoplasia.

SUMMARY OF THE INVENTION

The present invention provides systems and methods for the determination of the physical characteristics of a structured layer of material using light scattering spectroscopy. In a preferred embodiment, the light scattering spectroscopy system comprises fiber optic probes that can be used with existing endoscopes without modification to the endoscope itself. The system uses a combination of optical and computational methods to detect physical characteristics such as the size distribution of cell nuclei in epithelial layers of organs. The light scattering spectroscopy system can be used alone, or in conjunction with other techniques, such as fluorescence spectroscopy and reflected light spectroscopy.

In general, the light scattering spectroscopy system of the present invention is suitable for determining particle size distributions, and comprises an optical probe comprising at least one illumination optical fiber, a plurality of collection optical fibers, at least two of the plurality of collection optical fibers being oriented at different angles or in different planes; a light source; a detector system that acquires spectra of polarized light and unpolarized light; an analysis program capable of receiving the acquired spectra and comprising executable instructions; and a data processor capable of executing the analysis program instructions and determining the particle size distribution. In general, the detector system comprises a charge coupled device (CCD), CMOS imaging device or other image sensor.

In one embodiment, the light scattering spectroscopy system acquires fluorescence spectra as well as light scattering spectra. In another embodiment, the light scattering spectroscopy system acquires reflectance spectra, fluorescence spectra as well as light scattering spectra.

In one preferred embodiment, at least one illumination optical fiber supplies an corrected broadband illumination that has been filtered to compensate in part for the net wavelength-dependent sensitivity of the optical system. Generally, when using a CCD detector, the optimized illumination power per unit wavelength will be greater at the blue end of the spectrum where CCD sensitivities are generally lower and lower at the red end of the spectrum where CCD sensitivity is generally high.

In accordance with a preferred embodiment of the present invention, a spectroscopic diagnostic system includes an optical probe that provides backscattered spectra so that any underlying fluctuations in the backscattered light spectra appear directly as the result of a differential spectroscopic measurement. In a particular embodiment, the probe is used to detect polarized light. In some embodiments, the probe contains crossed polarizers, while in other embodiments, the probe contains a single polarizer. By using polarized light, the spectrum of the background scattered light can be subtracted out automatically, making real-time analysis possible in place of current offline analysis methods.

The foregoing and other features and advantages of the articles, systems and methods of the present invention will be apparent from the following more particular description of preferred embodiments as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

Preferred embodiments of the present inventions are described with reference to the following drawings, wherein:

FIGS. 10A-B, illustrate reflectance spectra from cell monolayers for normal colon cells; and T84 cells respectively;

FIG. 10C illustrates nuclear size distributions from data of FIGS. 10A and 10B;

DETAILED DESCRIPTION OF THE INVENTION

Figure 1:
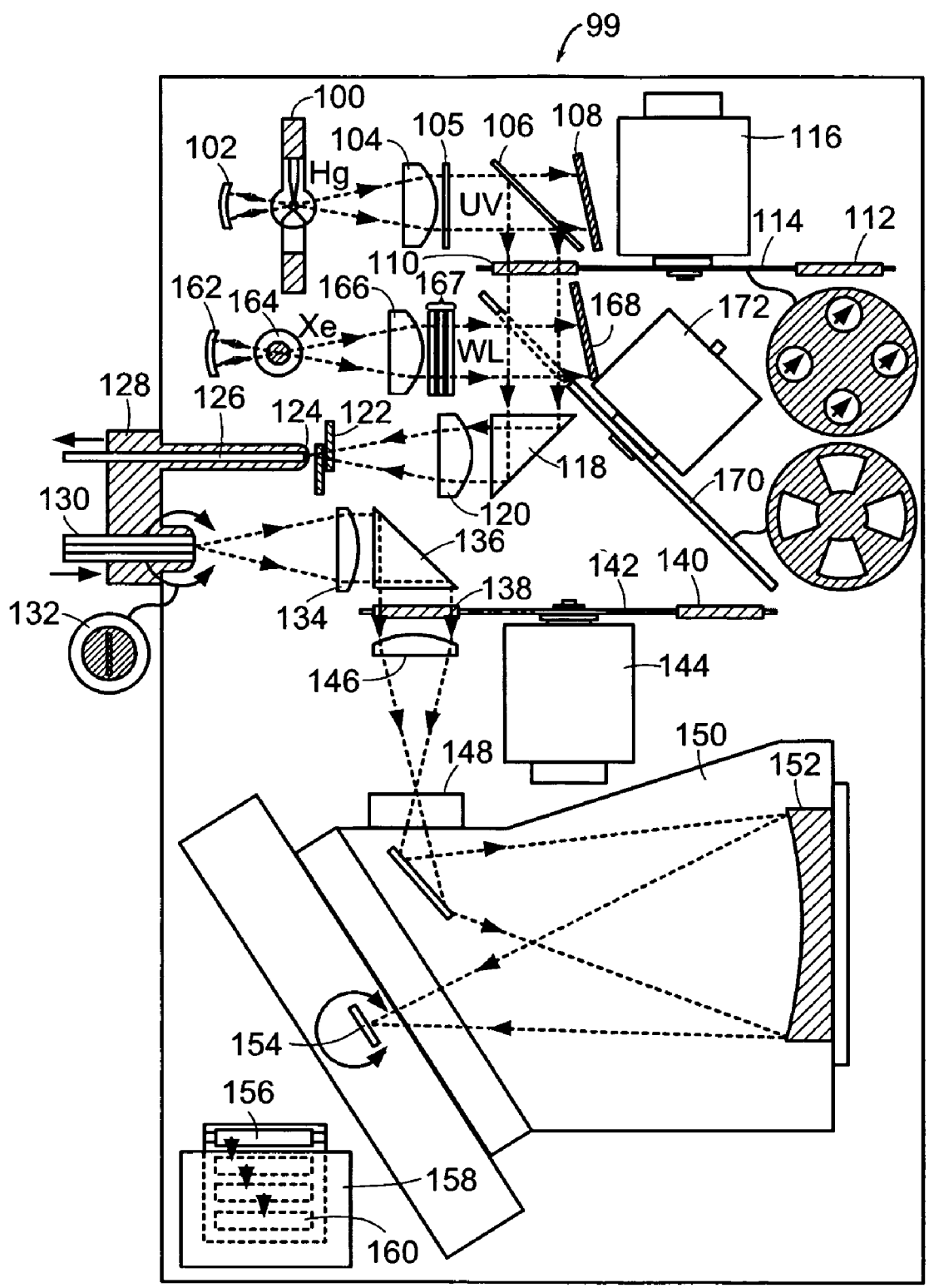
FIG. 1 is a schematic diagram illustrating one embodiment of a light source and detector system for a light scattering spectroscopic system.

In general, the light scattering spectroscopy system of the present invention is suitable for determining particle size distributions, and comprises an optical probe comprising at least one illumination optical fiber, a plurality of collection optical fibers, at least two of the plurality of collection optical fibers being oriented in different planes; a light source; a detector system that acquires spectra of polarized light and unpolarized light; an analysis program capable of receiving the acquired spectra and comprising executable instructions; and a data processor capable of executing the analysis program instructions and determining the particle size distribution. In general, the detector system comprises a charge coupled device (CCD) a CMOS imaging device or other pixellated imaging sensor.

The light scattering spectroscopy system of the present invention may further comprise a central processing unit, memory storage systems and display devices that are capable of executing sampling and analysis software. In one embodiment, software calculates the spectrum that a particular design of LSS probe will return for a given diameter of scattering particle in the absence of a diffusely scattering background. The software calculates the power scattered by a spherical particle with a given diameter and refractive index in a medium of a given refractive index for a range of wavelengths and for a set of scattering angles ranging from 0 degrees to 180 degrees. The full Mie calculation is moderately complex, so this data is preferably stored in a large look-up table for the remainder of the probe simulation. A Monte Carlo integration over all possible scattering angles that the particular probe recovers from the tissue is then performed, summing the spectra for each scattering angle as it is calculated. The range of angles possible is determined by the diameter of the illumination optical fiber (typically 200 µm), the diameter of the collection optical fibers (typically 50 µm to 200 µm), the separation of the optical fibers (typically 240 µm to 400 µm), the length of the window at the probe tip (typically 1 mm to 5 mm), the numerical apertures of the optical fibers (typically 0.22 to 0.4), the relative angle of the collection optical fibers to the axis of the probe (for preferred embodiment in which the fibers are canted inward to increase the overlap of the "viewed" area of the tissue) and the angle of orientation a polarizer if it is included. This software has been used to form the LSS spectra for unpolarized light optical probes as well as the spectra that can be produced by the improved, single-polarizer optical probe of the present invention.

The wavelength dependence of light backscattered from enlarged (and more refractive) cell nuclei is the physical basis for applying LSS to the detection of tissue dysplasia. An increase in the size and density of the cell nuclei at the tissue surface indicates dysplasia. A plot of backscattered light power versus wavelength (a spectrum) exhibits higher frequency oscillations in wavelength for larger, dysplastic nuclei than from smaller, normal cell nuclei. These oscillations are typically only a few percent of the total reflected light signal from the tissue. Subtraction of the large background signal is thus an important part of the analysis method.

One embodiment of a suitable light source and detector system 99 for the light scattering spectroscopy system is shown schematically in plan view in FIG. 1. Light is provided by a mercury (Hg) lamp 100 and a xenon lamp (Xe) 164, each provided with reflectors 102 and 162, respectively. In this figure, for purpose of illustration, the mercury lamp 100 has been rotated 90 degrees relative to the xenon lamp 164, but in most embodiments these lamps can be in the same orientation. Light from the mercury lamp 100 is collimated by lens 104, passes through filter 105 and the filtered light is redirected by dichroic reflector 106. Filter 105 is selected to reduce the short wavelength UV while passing longer wavelength UV and visible light. A suitable filter 105 is one of the Schott WG series filters. Visible and infrared radiation produced by mercury lamp 100 passes through the dichroic reflector 106 and is absorbed by filter 108. Redirected UV light passes alternatively through excitation filters 110 and 112 that are carried by filter wheel 114 that is moved by motor 116.

Similarly, white light from the xenon lamp 164 is collimated by lens 166, passes through filter group 167, and is either redirected by reflective coated wheel 107, or passes through sectors in wheel 107 to be absorbed by filter 186. Filter group 167 modifies the spectrum of the light collected from the xenon arc lamp 164 so that the number of photoelectrons generated in each pixel of the CCD detector is relatively uniform across the spectrum. The maximum number of photoelectrons at any point in the spectrum must not exceed the well depth of the particular CCD used to avoid spillover effects into neighboring pixels. The signal to noise ratio at any pixel in the detected spectrum is also proportional to the square root of the number of photoelectrons collected by that pixel. The optimum illumination is thus not white light, defined as a uniform power per unit wavelength across the spectrum, but a modified, broadband illumination ("white light" in quotes hereafter). Generally, the optimal illumination power per unit wavelength is greater at the blue end of the spectrum where CCD sensitivities are generally lower and lower at the red end of the spectrum where CCD sensitivity is generally high. Other factors to be considered are the dispersion of the spectrometer, the losses in the optical elements, the general reflectance spectrum of tissue and the spectral profile of the lamp generating the illumination. A stacked set of solid glass absorption filters, such as those produced by Schott, is suitable for obtaining an optimal illumination power. In particular, Schott WG, UG and GG filters can be used to enhance the spectrum at the blue end of the spectrum and infrared-absorbing filters, such as the Schott KV series, can be used to attenuate the red end of the spectrum.

Visible and infrared radiation passes through the dichroic reflector 106 and is absorbed by filter 108. Filter wheel 114 and reflective wheel 170 are controlled and moved by motors 116 and 172, respectively, so that white light and UV light are alternatively directed by prism 118 through lenses 120 and 124 onto the end of optical fiber 126. The timing of the illumination of the end of optical fiber 126 is controlled by shutter 122. In preferred embodiments, the power supply to either or both lamp 100 and lamp 164 can be pulsed.

Light gathered by one or more optical fibers 130 is passed by lenses 134 and 146 through the entrance slit 148 of holographic grating spectrometer 150. In a preferred embodiment, a linear array of multiple optical fiber ends 132 (shown here rotated by 90 degrees for illustrative purposes) is passed by lenses 134 and 146 through the entrance slit 148. Prism 138 directs the light path through UV blocking filters 138 and 140 that are carried on wheel 142 that is turned by motor 144. Spectra produced by grating 152 are imaged on CCD detector 154. In one embodiment, multiple spectra 156, 160 are imaged in succession on the CCD detector 154 by moving the detector beneath a mask 158. In another embodiment, several spectra can be imaged on the CCD detector separately, see FIG. 2, FIG. 3 and FIG. 4. In both embodiments several spectra are stored sequentially and the CCD is read once.

The unpolarized Tri-Modal Spectroscopy (TMS) system generally requires the acquisition of two or more fluorescence spectra and a white light reflectance spectrum. Various methods of TMS are described in International Application No. WO 02/057757, filed Jan. 18, 2002, U.S. Pat. Ser. No. 10/052, 583 filed Jan. 18, 2002, and U.S. patent Ser. No. 09/766,879, filed Jan. 19, 2001, which are incorporated herein by reference in their entirety. The optical probe consists of fused silica optical fibers (for the optimal transmission of the deeper UV fluorescence excitation wavelengths) which can be arranged in a hexagonal close-packed bundle for the minimal diameter. At least one optical fiber will be used to deliver light ("illumination optical fiber") to the tissue with the optical fibers not used for illumination being used for collection of the resulting fluorescence or reflected light for spectral analysis ("collection optical fiber").

Figure 2A:
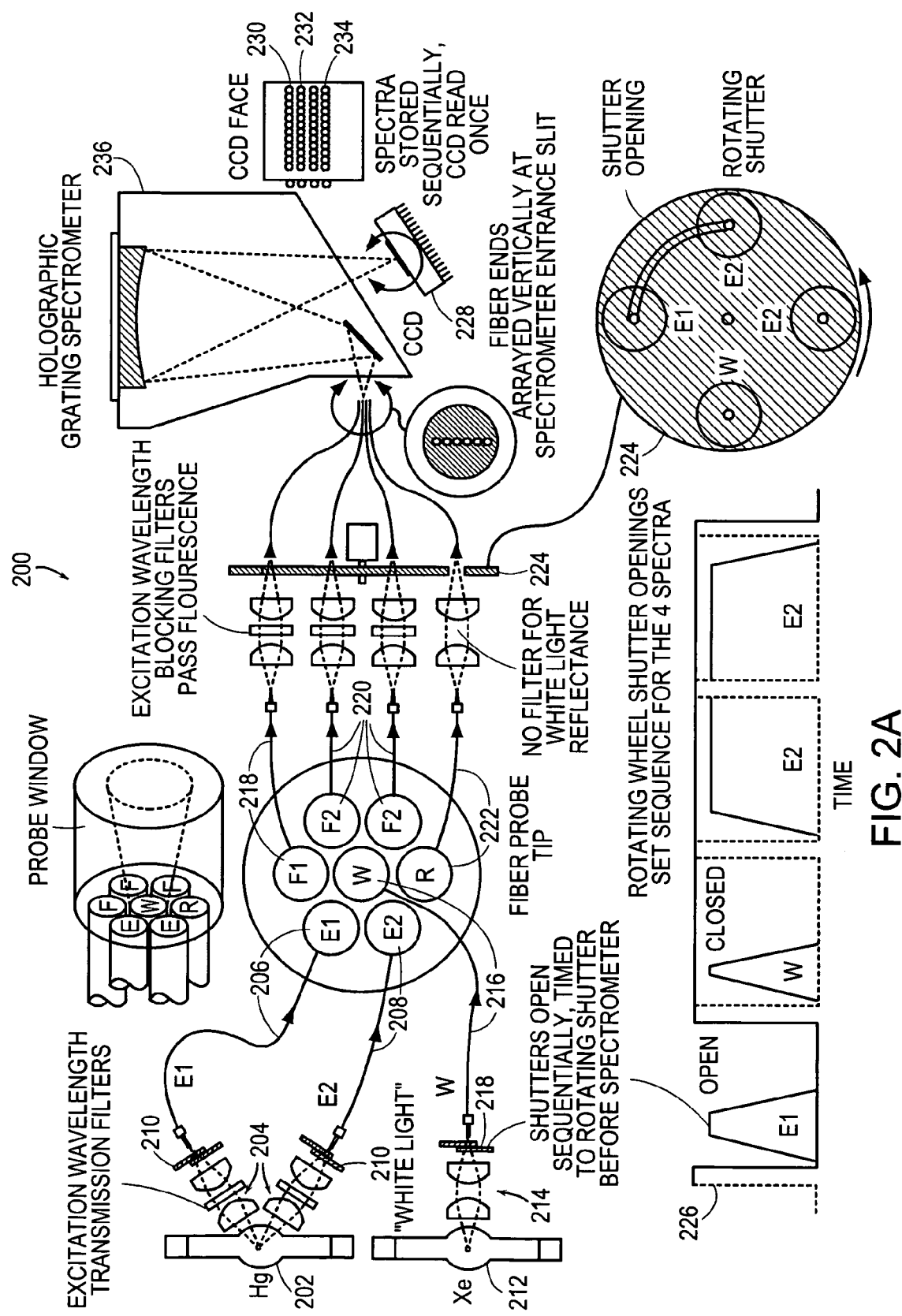
FIG. 2A is a schematic diagram illustrating one configuration of a system providing fluorescence and reflectance spectra as well as light scattering spectroscopy.

The use of more than one of the optical fibers for delivering light to the tissue has the advantage of simplifying the mechanical and electrical design of the system at the cost of reducing the amount of fluorescence light collected. The schematic diagram 200 in FIG. 2A illustrates an embodiment of an unpolarized TMS system using this type of light source and collection design. Two fluorescence wavelengths are simultaneously collected from a mercury arc lamp source 202 (at 340 nm and 405 nm for instance) using f/2 optical systems 204 to match the acceptance angle of typical all-fused-silica optical fibers 206, 280 with a numerical aperture (NA) of 0.22. The illumination is delivered by two separate optical fibers with individual fast blade shutters in each path so that pulses of the two excitation illuminations can be delivered to the tissue sequentially. Similarly, the corrected broadband illumination 212 ("white-light") required for the reflectance spectrum is collected by its own optics 214 and delivered into a separate illumination optical fiber 216 with its own shutter 218. This embodiment thus uses three of the seven fibers for light delivery but does not require optical or mechanical mixing of illumination power into a single illumination fiber. The higher speed at which this embodiment can switch between fluorescence illumination and white light illumination is another advantage of this system.

Because the fluorescence emitted from the tissue is weaker than the excitation by about a factor of 1000, the fluorescence collection path requires an excitation blocking filter to reduce scattered and reflected excitation wavelengths sufficiently to prevent saturating the fluorescence detection system. In the embodiment shown in the FIG. 2A, specific collection fibers 218, 220, 222 are assigned to specific fluorescence and reflectance wavelengths so that the required filters are always in place. Again, this speeds the overall spectral collection time since filters do not need to be moved into place, but reduces the amount of light collected for a given spectrum. A timed shutter needs to be in the individual collection paths as well, so that only a single path is open from the light source to the tissue to the spectrometer at a given time. This is achieved with a continuously rotating wheel shutter 224 with a timing cycle 226 as shown in the lower portion of FIG. 2A.

The detection system in FIG. 2 uses a CCD camera 228 to detect the resulting spectra. Since individual optical fibers are assigned to specific fluorescence or reflectance wavelengths the spectral acquisition is simplified. The exit faces of the four optical fibers shown are imaged onto different row positions 230, 232, 234 of the CCD detector and the spectra are spread out across the CCD columns by the spectrometer dispersion 236. The CCD stores each sequential spectrum as the illumination and collection paths are switched open. The acquired spectra are read-out at one time as a spectral "image" using standard CCD read-out electronics.

Figure 2B:
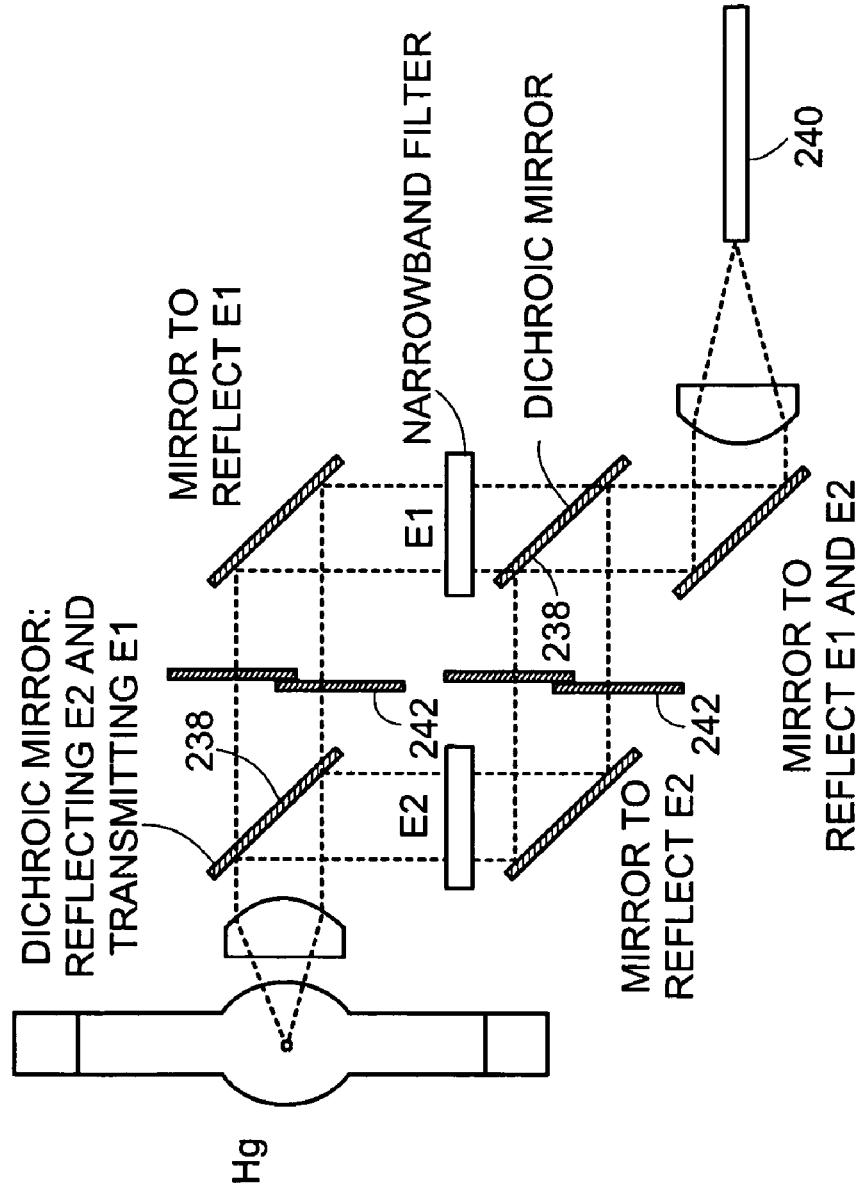
FIG. 2B is a schematic diagram illustrating an embodiment in which a dichroic mirror is used to separate two wavelengths and recombine them into one illumination optical fiber after filtering.

FIG. 2B illustrates schematically an embodiment 237 in which two excitation wavelenths, E1 and E2, that are sufficiently separated in wavelength that dichroic mirrors 238 can be used to separate the two wavelengths and then recombine them, after additional filtering into one illumination optical fiber 240. The two separate optical paths can also include shutters 242 to provide independent timing of illumination with E1 and E2.

Figure 3A:
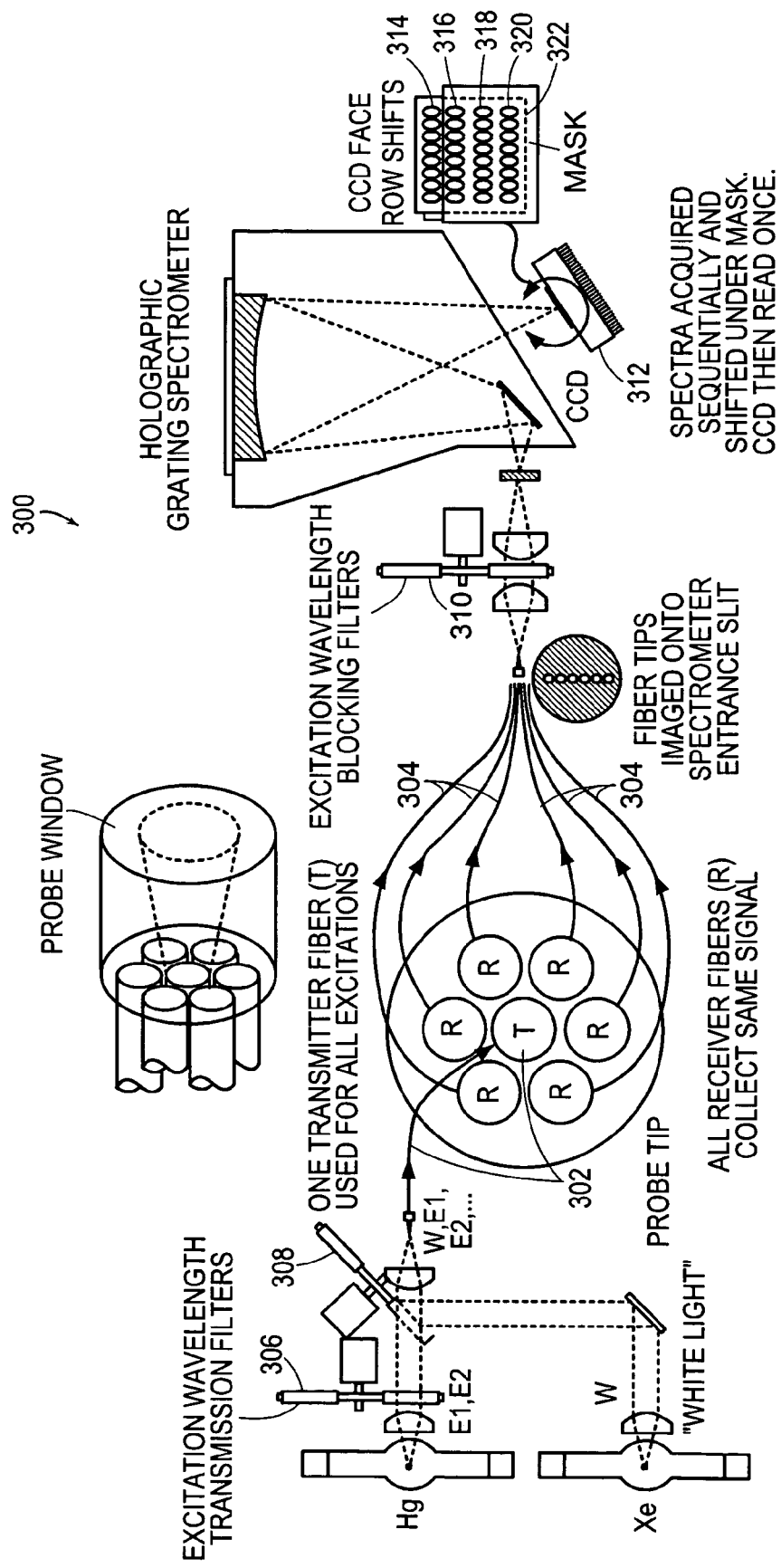
FIG. 3A is a schematic diagram illustrating another configuration of a light scattering spectroscopic system.

Another alternative embodiment is shown in FIG. 3A. In this embodiment 300, all of the illumination colors are multiplexed into a single illumination fiber 302 so that all of the remaining fibers 304 can be used for the collection of each resulting fluorescence or reflectance spectrum. This approach has the advantage of multiplying the collected power by a factor of six at the cost of having to shift appropriate filters into the optical paths at the appropriate times, which slows down the overall collection time for the system. Rotating wheels 306, 308 are used to shift the filters into place in the optical paths. The wheels can be continuously turning if the filters are large enough to accommodate the required exposure duration. Alternatively, stepper or servo motors can be used to rotate smaller filters into place at the appropriate time. Again, the excitation pass filter 306 and the excitation blocking filter 310 must be synchronized.

In the embodiment FIG. 3A, as in the embodiment of FIG. 1, the row shifting electronics in the CCD detector 312 are used to move each successive spectrum to a storage area on the CCD 314, 316, 318, 320 after it is acquired. This storage area on the CCD is preferably covered by an external mask 322 to prevent stray light from degrading the spectra. After all of the spectra are exposed, the row shifting is continued in the normal fashion to read out all of the spectra.

Figure 3B:
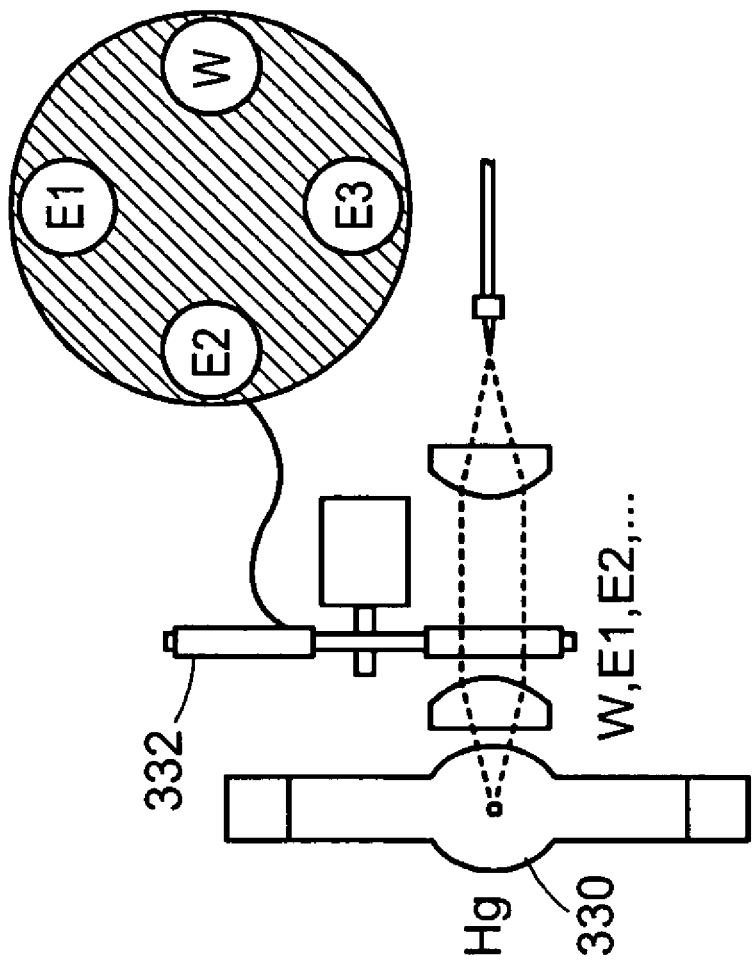
FIG. 3B is a schematic diagram illustrating another configuration of a light scattering spectroscopic system in which the mercury arc lamp is also used as the white light source.

The schematic diagram shown in FIG. 3B illustrates an embodiment 329 in which a single mercury lamp 330 can be used as a source for corrected broadband illumination ("white light" as described above), as well as several fluorescence excitation wavelengths, E1, E2 and E3. The different wavelengths are selected by movement of the appropriate filters, already discussed above, into the optical path using a filter wheel 332.

Figure 4:
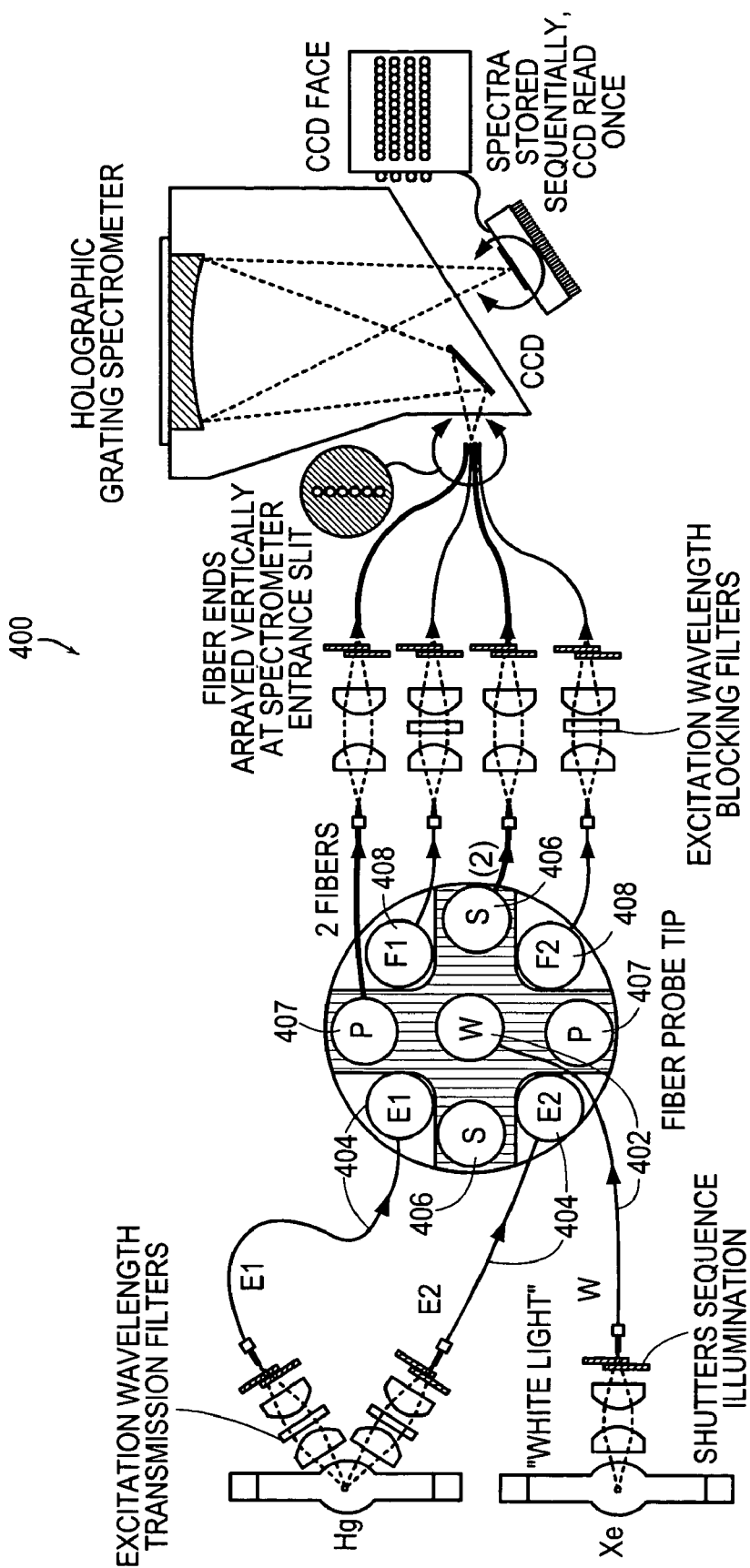
FIG. 4 is a schematic diagram illustrating one embodiment of a system providing fluorescence and reflectance spectra as well as polarized light scattering spectroscopy.

FIG. 4 illustrates an embodiment in which polarized light is emitted from the illumination optical fiber and the light collected by at least two collection optical fibers, preferably by four collection fibers. The details of the relationship of the illumination and collection optical fibers to the polarizer are illustrated schematically in FIGS. 5A-5B for both a single polarizer optical probe (FIG. 5A) and a crossed polarizer optical Probe (FIG. 5B).

Optical fiber probes for LSS typically transmit white light to the tissue through at least one illumination optical fiber and collect the reflected light from the tissue with one or more collection optical fibers. The light collected includes both backscattered light from the cell nuclei at the tissue surface (the signal of interest) and diffuse light scattered from deep in the tissue (the much larger background signal). The collected light is analyzed with a spectrometer to generate a spectrum over a wavelength range from the near ultraviolet (UV) to the near infra-red (IR). LSS optical probes currently used for clinical studies illuminate the tissue with unpolarized white light and collect a single, unpolarized, reflected light spectrum for analysis. The background signal must be removed from this unpolarized spectrum by modeling the expected spectrum of diffuse scattered light. The model includes, for example, parameters which account for the amount of blood in the tissue. This type of modeling is slow and subject to error. While unpolarized LSS optical probes have the advantages of returning a spectrum over the widest possible wavelength range and of being relatively simple to make, the need to use modeling for the background subtraction, however, is a significant disadvantage.

The use of crossed polarizers in an LSS probe has been proposed by various groups as a means of improving on the subtraction of the background signal as described in U.S. Pat. No. 6,404,497, issued Jun. 11, 2002 and International Application WO 00/43750, filed Jan. 25, 2000, both of which are incorporated herein by reference in their entirety. In a cross-polarized LSS probe the illumination fiber is covered with a polarizer (at its distal tip) so that the light reaching the tissue is polarized. In this case, the backscattered light from the cell nuclei at the tissue surface is also polarized in the same plane as the incident light. Diffuse scattered light from deeper in the tissue results, as before, in a large background signal compared to the backscattered light from the nuclei. This background light is, to a great extent (but not completely), depolarized by multiple, out-of-plane, scattering events before the light returns to the tissue surface. In a cross-polarized LSS optical probe, at least two collection optical fibers are also covered with a polarizing layer, one of which passes light which is polarized parallel to the polarization of the incident light and one of which passes light polarized perpendicular to the polarization of the incident light. The light scattering spectrum of collected light polarized parallel to the polarization of the incident light contains the spectrum of the backscattered signal from the cell nuclei plus the spectrum of the diffuse (unpolarized) background light. The light scattering spectrum of collected light polarized perpendicular to the polarization of the input light will contain only the spectrum of the diffuse background light. Differencing these two light scattering spectra leaves only the desired spectrum of the backscattered light from the nuclei of the epithelial cells.

While cross-polarized LSS optical probe designs have the advantage of not requiring the difficult background subtraction modeling, they are more expensive to make than the unpolarized designs. Currently available thin-film polarizers also have a limited useful spectral range of operation, so the acquired spectra are more difficult to analyze. There is also a considerable amount of power reflected from deeper in the tissue that retains the polarization of the input signal, and is thus not subtracted from the spectrum of the cell nuclei at the tissue surface. The background subtraction is thus not complete.

A design for a single-polarizer optical optic probe for LSS has the same advantage as the crossed-polarizer optical probe design in that the optical probe can be used to generate two light scattering spectra, rather than one. Differencing these two light scattering spectra eliminates the spectrum of the background diffusely scattered light.

However, the two light scattering spectra produced by the single polarizer optical probe have an important additional useful feature beyond that afforded by the crossed-polarizer probe design. By positioning the collection optical fibers properly in two different angles or planes relative to the position of the illumination optical fiber and the alignment of the single polarizer, the two light scattering spectra exhibit oscillations in wavelength which are at a much higher frequency (about six-fold) compared to the oscillations in-light scattering spectra acquired with unpolarized optical probes. These angles or oscillations in the spectra of light from the collection optical fibers placed in two different planes (designated "s" and "p") are also 180 degrees out of phase with each other, so that the differencing process which removes the background also effectively doubles the relative amplitude of this higher frequency oscillation. The higher oscillation frequency significantly simplifies the separation of this oscillating spectral component from low frequency spectral noise present in all LSS probe data.

Computer predictions of the signal generated by several optical probe embodiments are described below along with measurements using polystyrene beads in an index-matching fluid to simulate cell nuclei. Engineering design studies that indicate the preferred parameters for the probe, such as fiber size and position and the preferred length of the probe window, are also described.

In general, techniques are available for the construction positioning, and alignment of bundles of optical fibers in structures such as the optical probes of the present invention. See, for example U.S. Pat. No. 5,192,278, the teachings of which are incorporated by reference herein in their entirety.

Figure 5A:
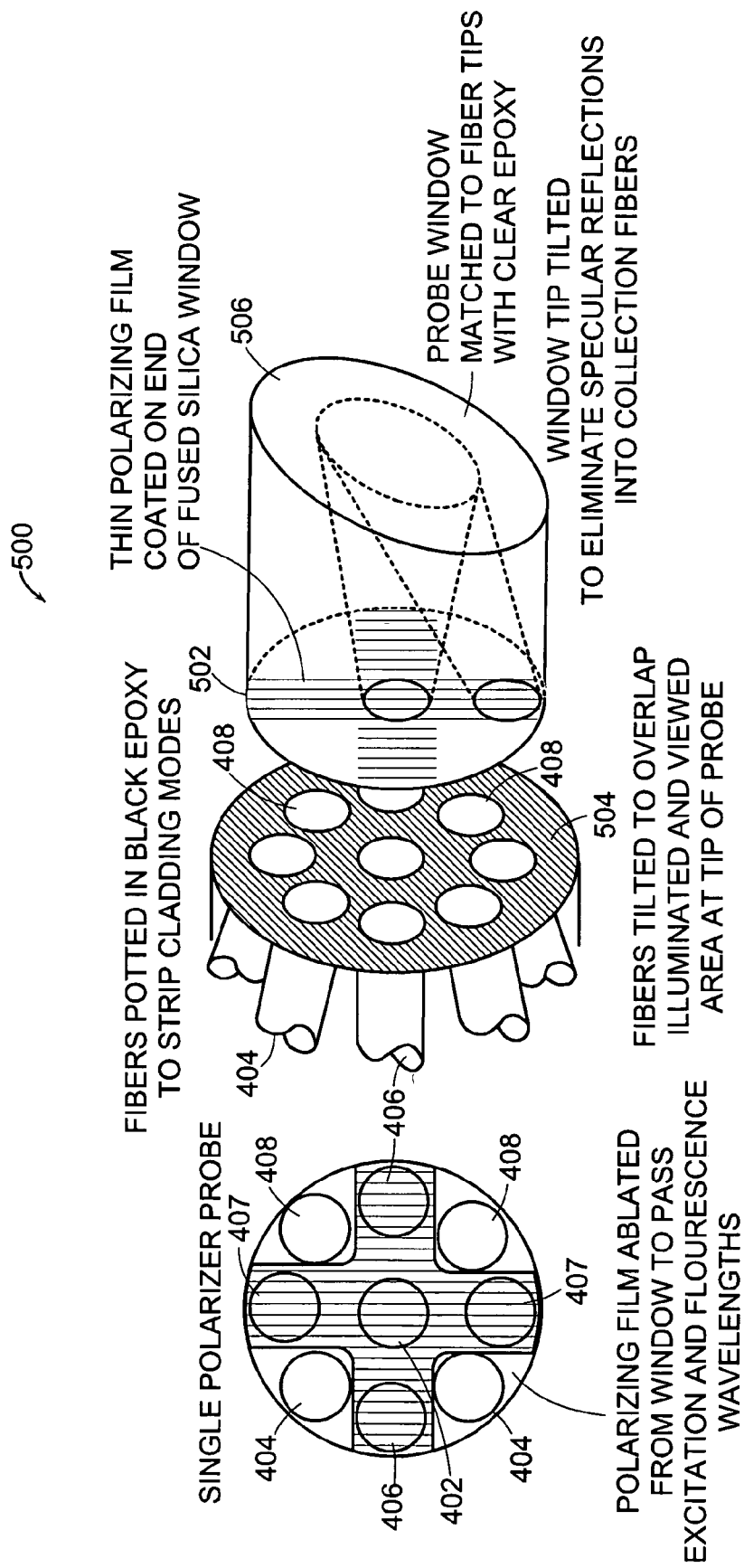
FIG. 5A is a schematic diagram illustrating one embodiment of an optical probe component of a polarized light scattering spectroscopic system that incorporates a single polarizer.
Figure 5B:
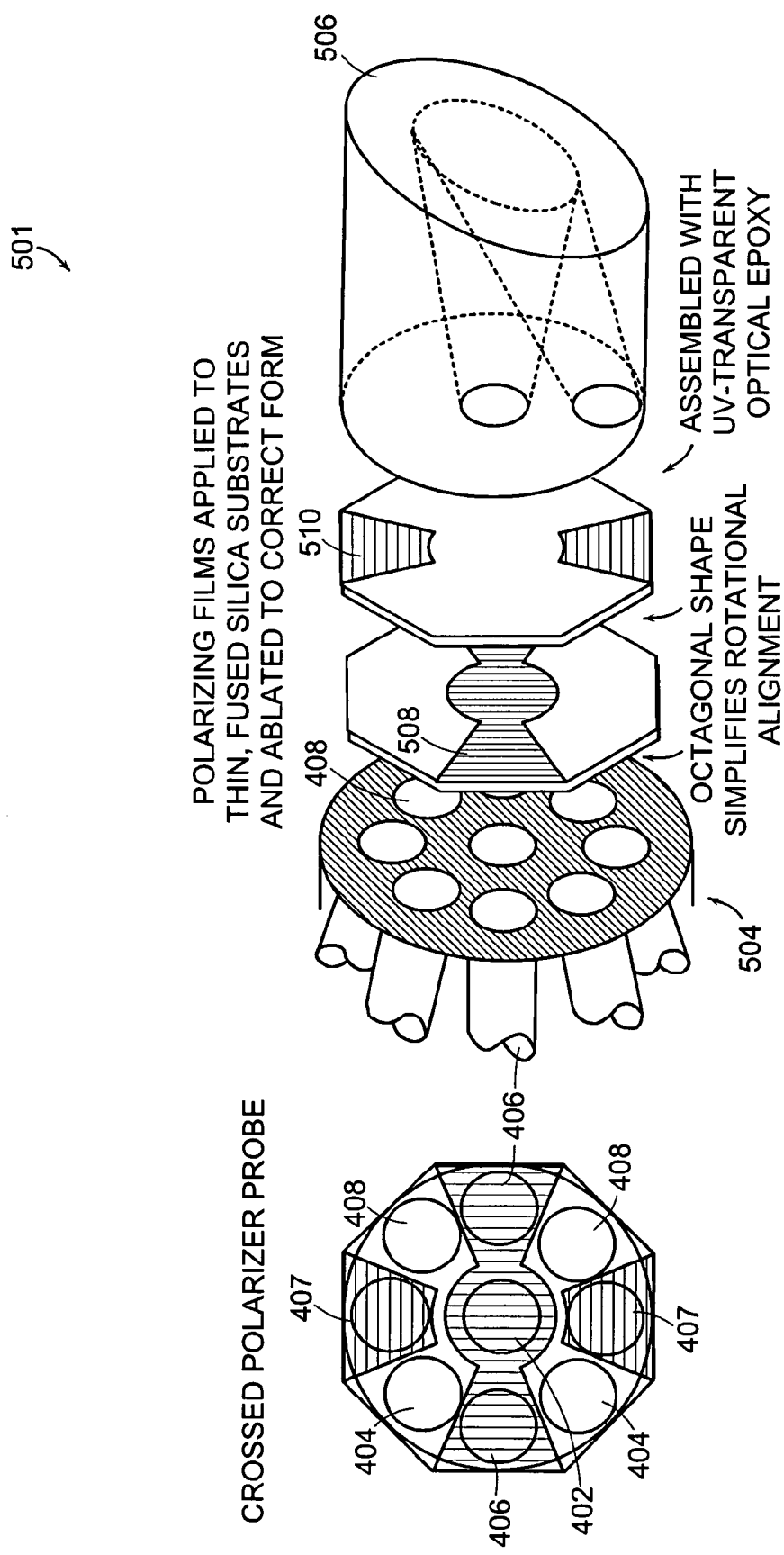
FIG. 5B is a schematic diagram illustrating one embodiment of an optical probe component of a polarized light scattering spectroscopic system that incorporates two crossed polarizers.

Two exemplary suitable probe designs 500, 501 are shown in FIGS. 5A-B. In these designs, a single illumination optical fiber 402 is used to deliver broadband illumination ("white light") to the tissue using the light source and detector system 400 of FIG. 4. The illumination optical fiber 402 is surrounded by a ring of optical fibers for excitation illumination 404 of the appropriate wavelengths for fluorescence spectroscopy, collecting the scattered light 406, 407 and collecting the emitted light 408, as shown in FIGS. 4 and 5A-B. The central illumination optical fiber 402 is typically 100 µm in diameter and the collection optical fibers 406-408 are typically 50 µm in diameter (with larger cladding diameters). The 2.4 mm overall diameter of the probe permits use of the probe with common biopsy channel dimensions of endoscopes such as gastroscopes. A single, thin film polarizer 502 can be placed between the tips 504 of the fibers and the probe window 506 as shown in FIG. 5A. In another embodiment, crossed polarizing films 508, 510 can be used as shown in FIG. 5B. In both embodiments, the polarizing film is preferably ablated over the fiber optics that are used to pass the excitation and emission wavelengths for fluorescence spectroscopy. In such a probe, the radial distance from the optical fiber tips to the central fiber is typically 0.35 mm. The distance from the tips of the optical fibers to the tissue, set by the combined thickness of the polarizer and window of the optical shield is typically 5 mm; resulting in a currently preferred central angle of 4 degrees for the collected backscattered light. This angle can suitably be in the range of about 2 degrees to about 6 degrees in various embodiments.

The overlap of the "illuminated" areas of the fibers can be obtained by angling the ring of optical fibers at 4 degrees as shown in FIGS. 5A and 5B. In one embodiment shown in FIGS. 5A and 5B, the ring of fiber optics is potted in black epoxy. In another embodiment, the central fiber optic can be surrounded by a relatively soft plastic plug that presses the ring of fibers against a tapered surface or hole in the main body of the probe tip. The fibers are tilted to overlap an illuminated and viewed area at the tip of the probe. This assembly is then epoxied together with the fibers extending slightly from the lower surface of this main body. Once the epoxy has hardened, the main body of the probe and its fibers is placed into a polishing jig and all of the fibers (and the tip of the main body itself) are polished back to a single plane. In one embodiment, the plastic thin film polarizer was cut separately and epoxied together with a fused silica rod (which forms the optical shield and window) into a thin metal sleeve fitted to the main body. The finish on the outer edges of this polarizer is not critical since the fiber tips are close to the central axis of the probe. It has been found that it is possible to polish the edge of the commercial plastic polarizers used in the scaled prototype probe to a figure of about 50 micrometers (measured under a microscope) without difficulty and without affecting the polarization effectiveness beyond that distance. The window tip and sleeve are then ground back to an angle of between 10 and 20 degrees, preferably about 15 degrees and polished together. A design study with the Zemax, non-sequential ray tracer showed that 15 degrees was a sufficient angle to prevent Fresnel reflections (even after dozens of internal reflections) from the glass/water discontinuity at the window tip from directing rays back into the acceptance angle of the collection fibers. A heat shrink tube of medical grade plastic protects the fibers and grasps a series of annular ridges on the outside of the main probe body to provide the structural rigidity required to push the probe through the biopsy channel and position it against the tissue. A similar heat shrink tubing was used in the fluorescence probe.

Figure 6:
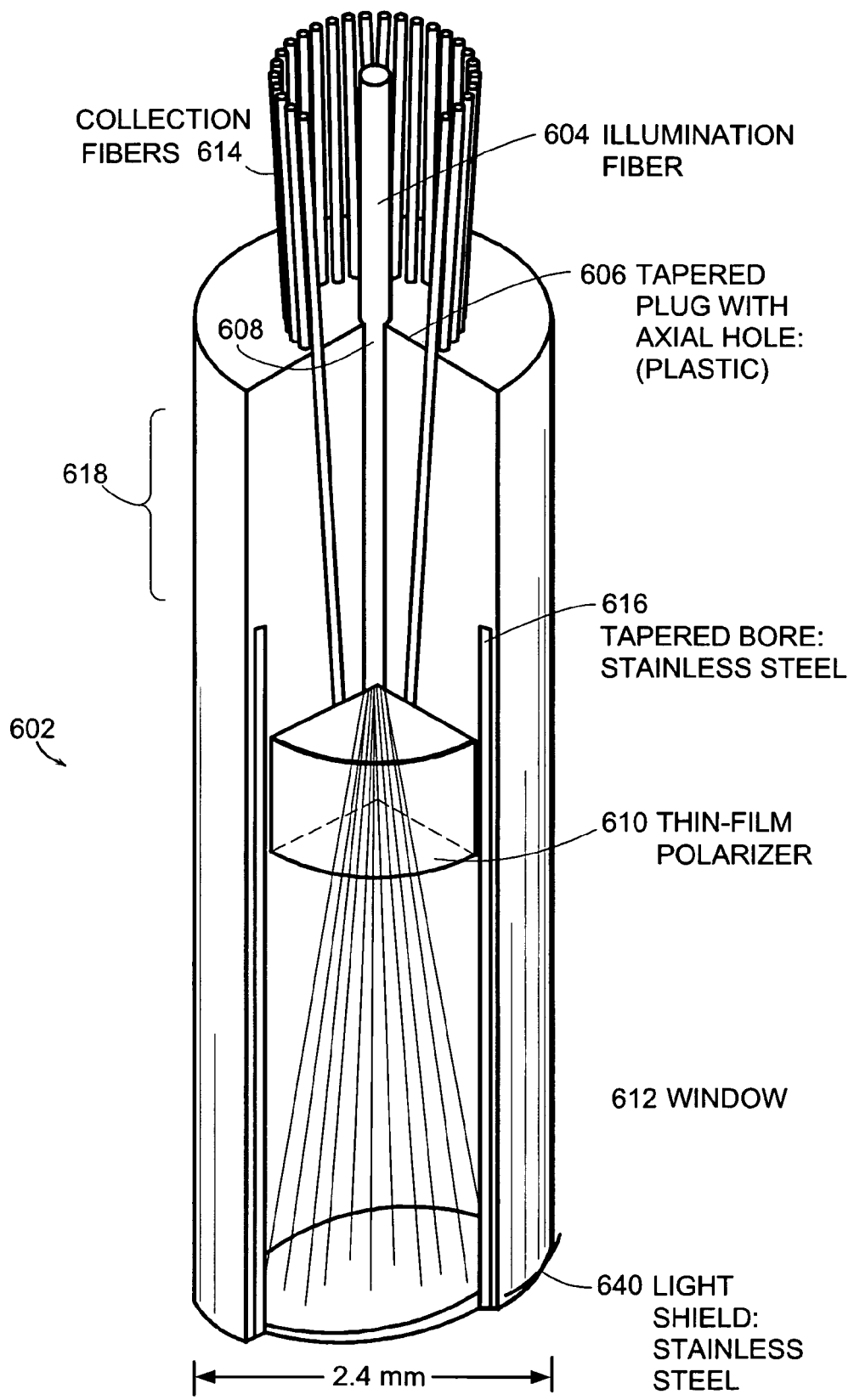
FIG. 6 is a schematic diagram illustrating one embodiment of an optical probe component of a polarized light scattering spectroscopic system that incorporates a retainer module that comprises an inner fiber support and an outer fiber support.

FIG. 6 is a more detailed schematic illustration of one embodiment of a single polarizer optical probe 602 suitable for the LSS system of the present invention. A single "white light" illumination optical fiber 604 is held on the probe axis by a tapered plug or retainer 606 with an axial hole 608. The retainer can be an epoxy, a plastic, or polymer material. The light from this fiber passes through the thin-film polarizer 610 which can be a separate optical component or laminated directly on the end of the probe window 612. The window 612 is of sufficient length that the light spread determined by the numerical aperture of the illuminating optical fiber covers most of the tip of the probe window. The distal sector 602 of the probe can be surrounded by a stainless steel cylinder 640 which also acts to shield the window prom peripheral light. A larger probe window is not desirable, since it would collect more background light into the probe tip than is necessary, increasing the likelihood that background light is scattered into the collection optical fibers 614. The collection optical fibers 614 are held at the appropriate collection angle by a tapered bore 616 in the probe tip body which matches the taper of the internal retainer 606 carrying the illumination fiber 604. The optical fiber retainer module 618 thus comprises an inner fiber support or retainer 606 and an outer fiber support 616 or the tapered bore of the probe tip body.

The optical fibers 614 shown in this embodiment are smaller in diameter than the illumination fiber 604, which results in a deeper modulation in the backscattered light spectrum. This is because the smaller fibers limit the angle over which the backscattered light is collected and thus reduces the averaging of the spectral oscillations that varies with backscattered angle. The optical fibers that collect the backscattered light in the plane of the input polarization can be separated from the optical fibers collecting light out of the input plane of polarization after the probe is assembled.

Figure 7:
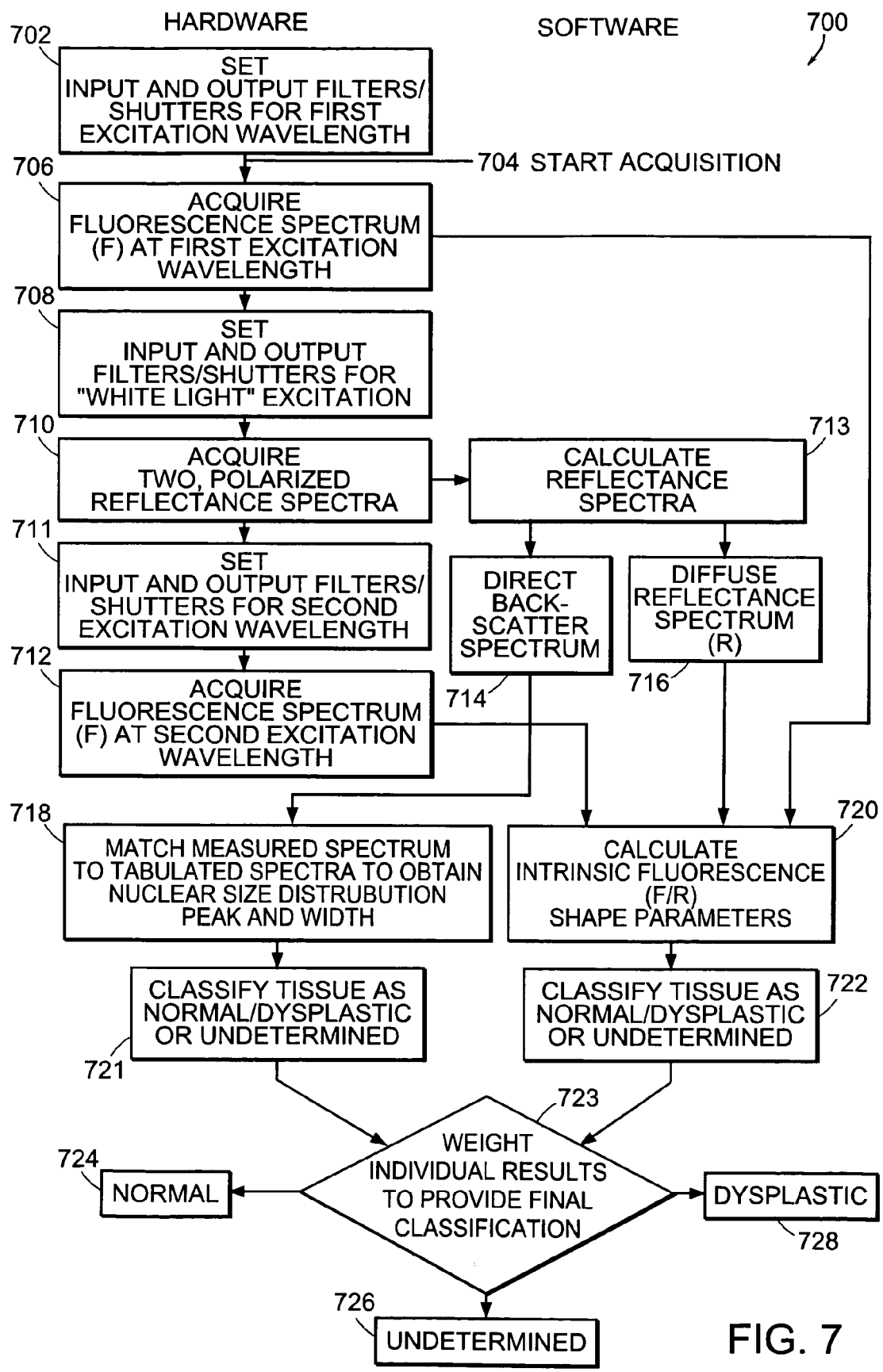
FIG. 7 is a schematic diagram illustrating an embodiment of an analysis program.

FIG. 7 is a flow chart 700 of a preferred embodiment of the process for analyzing the spectral data in accordance with the present invention. In general, the analysis process determines a set of particle size concentrations, $C_k$, that best fits the measured reflectance spectrum, $R(\lambda)$. The best fit is defined as the fit which minimizes the sum of the squares of the deviations at each wavelength divided by the estimated error in the measurement at that wavelength (chi-squared). The fit can be repeated for different refractive index ratios, m, if required. The solution for the desired coefficients is accomplished with the singular value decomposition method which is known to effectively avoid problems with singularities and computer round-off error. Typically, an analysis of this type can also be performed in a few milliseconds.

The flow chart in FIG. 7 indicates the steps involved in classifying the tissue state, as indicated by the distribution of the size of epithelial cell nuclei in one embodiment. The process is initiated by the clinician with a footswitch or other trigger. The system is initially maintained in a ready state to acquire a fluorescence spectrum, with the appropriate filters in place or shutters selected for triggering 702. Once initiated 704, the system takes the first fluorescence spectrum 706. The filters and shutters are then selected for "white light" excitation 708 and polarized reflectance spectra are acquired 710. The filters can be moved into position for the next fluorescence acquisition 711 (depending on the detailed design) while a reflectance spectrum is acquired 710. The final fluorescence spectrum is then acquired 712. The two reflectance spectra are differenced 713 to obtain the backscatter spectrum 714 for the LSS analysis and summed to obtain an unpolarized diffuse spectrum 716 for the intrinsic fluorescence spectra (IFS) analysis. The LSS analysis preferably proceeds as a least squares fit to the closest match in a pre-calculated table of spectra 718 predicted for the specific probe design in use. The table parameters include peak nuclear size, nuclear size distribution width and nuclear refractive index. The IFS analysis calculates the intrinsic fluorescence distribution (essentially F/R or fluorescence divided by reflectance) 720 and its characteristic parameters for comparison with previously obtained clinical spectra. A weighted result 723 of the two methods 721, 722 including their predicted reliability in each case, provides the final result for display 724, 726, 728 to the clinician.

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

An exact theory of light scattering from transparent spheres was developed by Gustav Mie in 1906, so the process has become known as Mie scattering. A modern description of the theory can be found in the publication by van de Hulst. Normal cell nuclei can be modeled as spheres with diameters of 5 to 7 µm and refractive indices of about 1.42 in a medium with a refractive index close to that of water (1.33). Dysplastic nuclei can be modeled as spheres with diameters of 10 µm and above.

Figure 8:
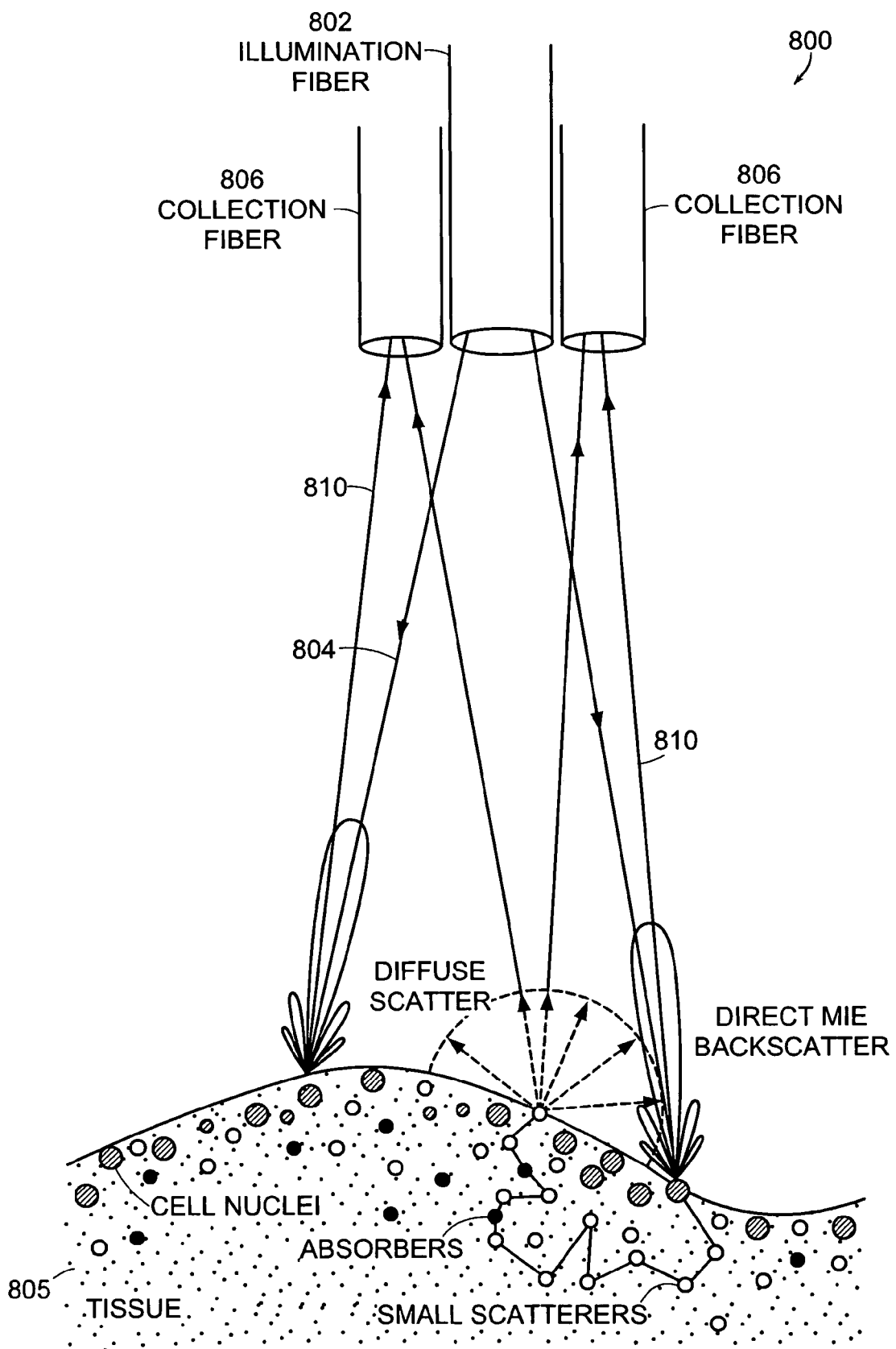
FIG. 8 is a schematic diagram illustrating an embodiment of an optical probe component of a light scattering spectroscopic system in relation to light from direct Mie backscatter and diffuse scattering.

The LSS spectra are collected with a fiber optic probe which is passed through a biopsy channel of an endoscope and pressed against the tissue to be measured. The tip of a typical probe 800 is shown schematically in a simplified form in FIG. 8. A central, illumination optical fiber 802 delivers "white light" 804 to the tissue 805 and separate collection optical fibers 806 return backscattered light 810 into a relatively narrow range of angles. The amount of light collected by these optical fibers at a particular wavelength depends upon the Mie scattering pattern for that wavelength. The size of the scattering particles can be determined by analyzing the spectrum of the returned light. In practice, a window in the optical shield on the probe tip holds the optical fibers at a fixed distance from the tissue so that the scattering geometry remains constant. The plane of the window can be perpendicular to the long axis of the probe, or tilted at another angle, such as 4 degrees, to reduce specular reflections into the collection fibers. See, for example, FIGS. 2A, 3, 5A and 5B.

As discussed above, the range of acceptance angles for a particular optical probe depend on the diameter of the illumination optical fiber, the diameter of the collection optical fibers, the spacing between the fibers, their numerical aperture (NA=sin(acceptance angle/2)) and the length of the probe tip from the distal end of the optical fibers to the window in the optical shield. The spectrum of the backscattered light detected by an LSS probe can thus be a product of a quite complex condition.

Figure 9A:
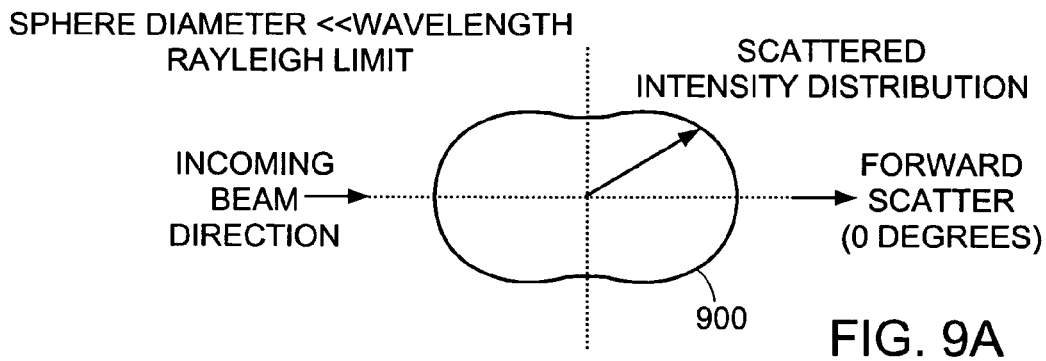
FIGS. 9A-C are diagrams illustrating typical Mie scattering intensity distributions for a single color for particles in the size ranges of interest for LSS measurements.
Figure 9B:
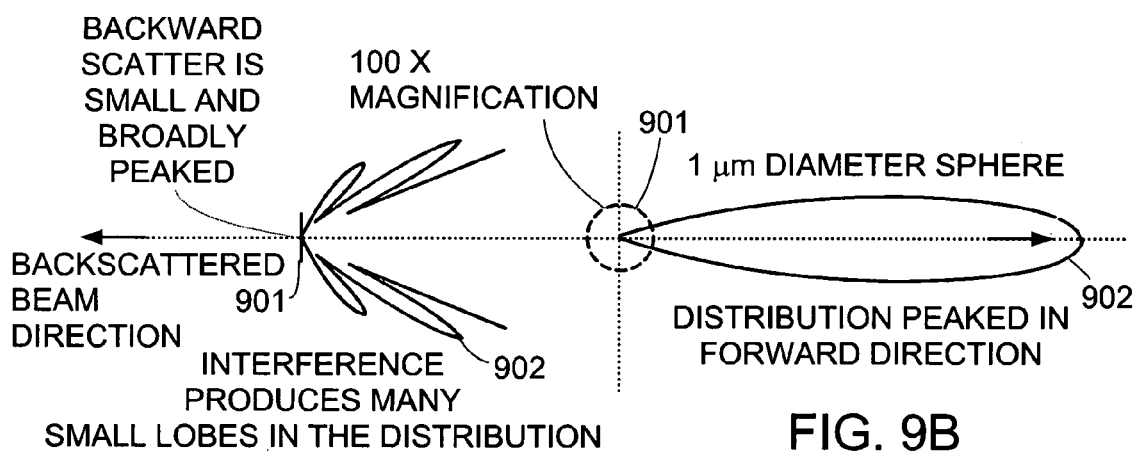
Figure 9C:
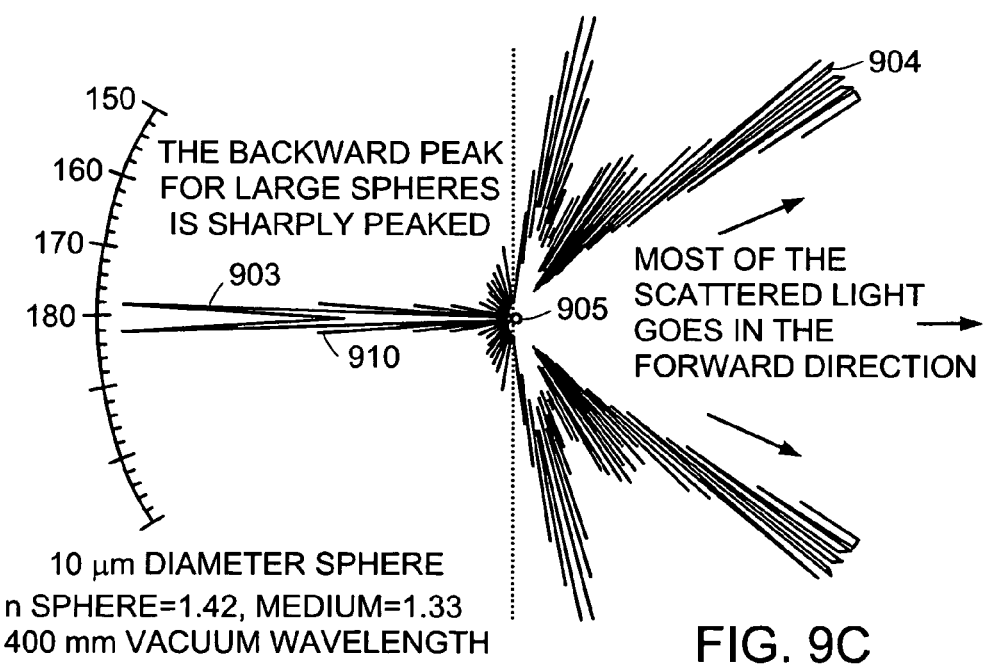

FIG. 9 shows schematically typical results of an exact Mie calculation of scattered intensity distributions 900 to illustrate how light scatters from particles 901, such as cell nuclei, that are much smaller than the wavelength of the incident light (FIG. 9A), and much larger than the wavelength of the incident light (FIG. 9B for a 1 µm diameter particle; FIG. 9C for a 10 µm diameter particle). The strong peaks near the direct backscatter direction (170 degrees to 180 degrees) are collected by the LSS optical probe and analyzed to determine the diameter of the scattering particles. These peaks shift rapidly in angle with changes in wavelength.

FIGS. 10A-D summarize the results of measurements taken by the research group at the MIT Biomedical Research Center using unpolarized LSS probes. Backman, V. et al., "Detection of preinvasive cancer cells. Early-warning changes in precancerous epithelial cells can now be spotted in situ," Nature, 406: 35-36 (2000); Wallace, M. B., et al., "Endoscopic detection of dysplasia in patients with Barrett's esophagus using light scattering spectroscopy," Gastroenterology 119: 677-682 (2000); Georgakoudi, I., et al., "Fluorescence, reflectance and light-scattering spectroscopy for evaluating dysplasia in patients with Barrett's esophagus," Gastroenterology 120: 1620-1629 (2000).

Figure 10E:
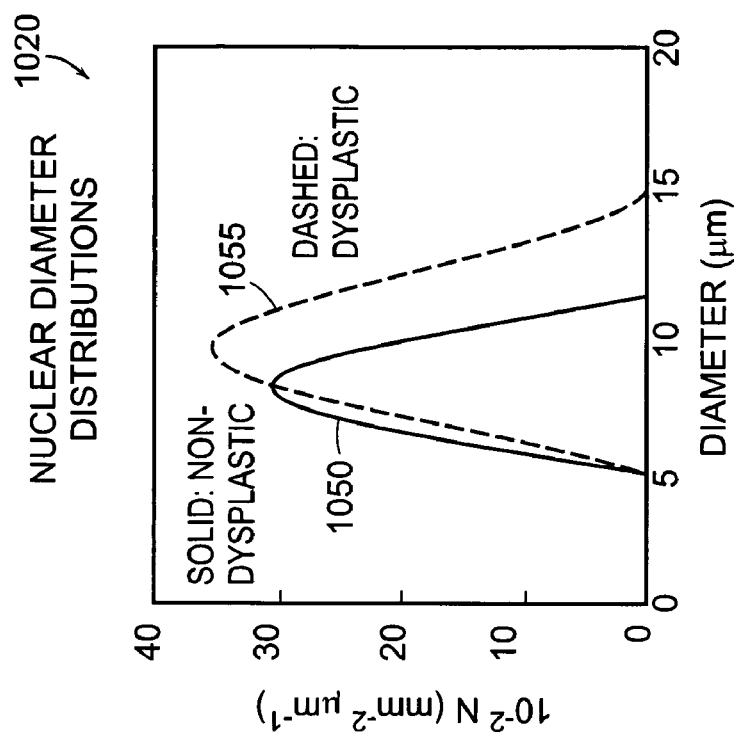
FIG. 10E illustrates nuclear size distributions for the data of FIG. 10D.

Data are shown in FIGS. 10A-E for both in vitro cultured cells and for in vivo Barrett's esophagus (BE) tissue. FIGS. 10A and 10B show the normalized reflectance $R(\lambda)/\overline{R}(\lambda)$ from normal 1001 and T84 tumor cell samples 1002, respectively. Distinct spectral features are apparent. In the cultured cell spectra, the broad peak which can be seen in the normal cell spectrum (FIG. 10A) near 400-450 nm is indicative of the scale size of the wavelength oscillation from unpolarized optical probes for the 6-7 μm diameter nuclei of a normal cell as shown in the analysis graph 1003 of FIG. 10C.

Figure 10D:
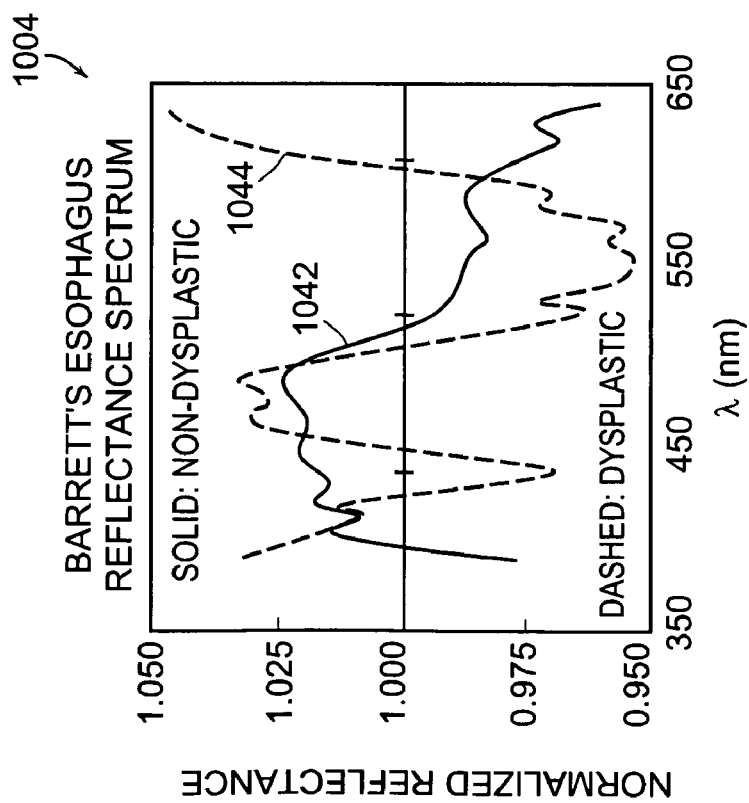
FIG. 10D is a reflectance spectra from Barretts' esophagus from a normal site (solid line), and dysplatstic site (dashed line)

To obtain information about the nuclear size distribution the reflectance data is inverted, for example, as described in U.S. Pat. No. 6,091,984 incorporated herein by reference in its entirety. The solid curves in FIG. 10C show the resulting fitted nuclear size distributions of the normal 1030 and T84 cell monolayer 1032 samples extracted from the spectra of FIGS. 10A and 10B. A nucleus-to-cytoplasm relative refractive index of n=1.06 and cytoplasm refractive index of $n_c$=1.36 were used. The dashed curves in FIG. 10C show the corresponding size distributions, measured morphometrically via light microscopy, of the normal 1033 and T84 cell monolayer 1062 samples. The extracted and measured distributions are in good agreement for both normal and T84 cell samples. FIG. 10D shows the reflectance spectra 1004, after removing the diffuse background structure by calculating $R(\lambda)/\overline{R}(\lambda)$, from two Barretts' esophagus tissue sites, both independently diagnosed by standard pathological analysis to indicate (1) normal (nondyplastic) 1042 and (2) precancerous (i.e. low grade dysplasia) 1044. After removing this diffuse background structure by calculating $R(\lambda)/\overline{R}(\lambda)$, the periodic fine structure is seen in FIG. 10D. Note that the fine structure from the dysplastic tissue site exhibits higher frequency content than that from the normal site. The extracted respective nuclear size distributions are shown in FIG. 10E. The difference between the distribution for the normal 1050 and dysplastic tissue 1055 sites is evident. The distribution of nuclei from the dysplastic site 1055 is much broader than that from the distribution from the normal site 1050 and the peak diameter is shifted from ~7 μm to about ~10 μm. In addition, both the relative number of large nuclei (>10 μm) and the total number of nuclei are significantly increased.

The particle size distributions derived from the spectra show that the nuclei of dysplastic cells in BE tissue exhibit measurable differences in their nuclear size and density. By comparing these size distributions with the results from pathology on biopsy samples taken from the same sites, a process sequence was developed that predicts the results of the biopsies from the nuclear size distribution analysis.

Figure 11:
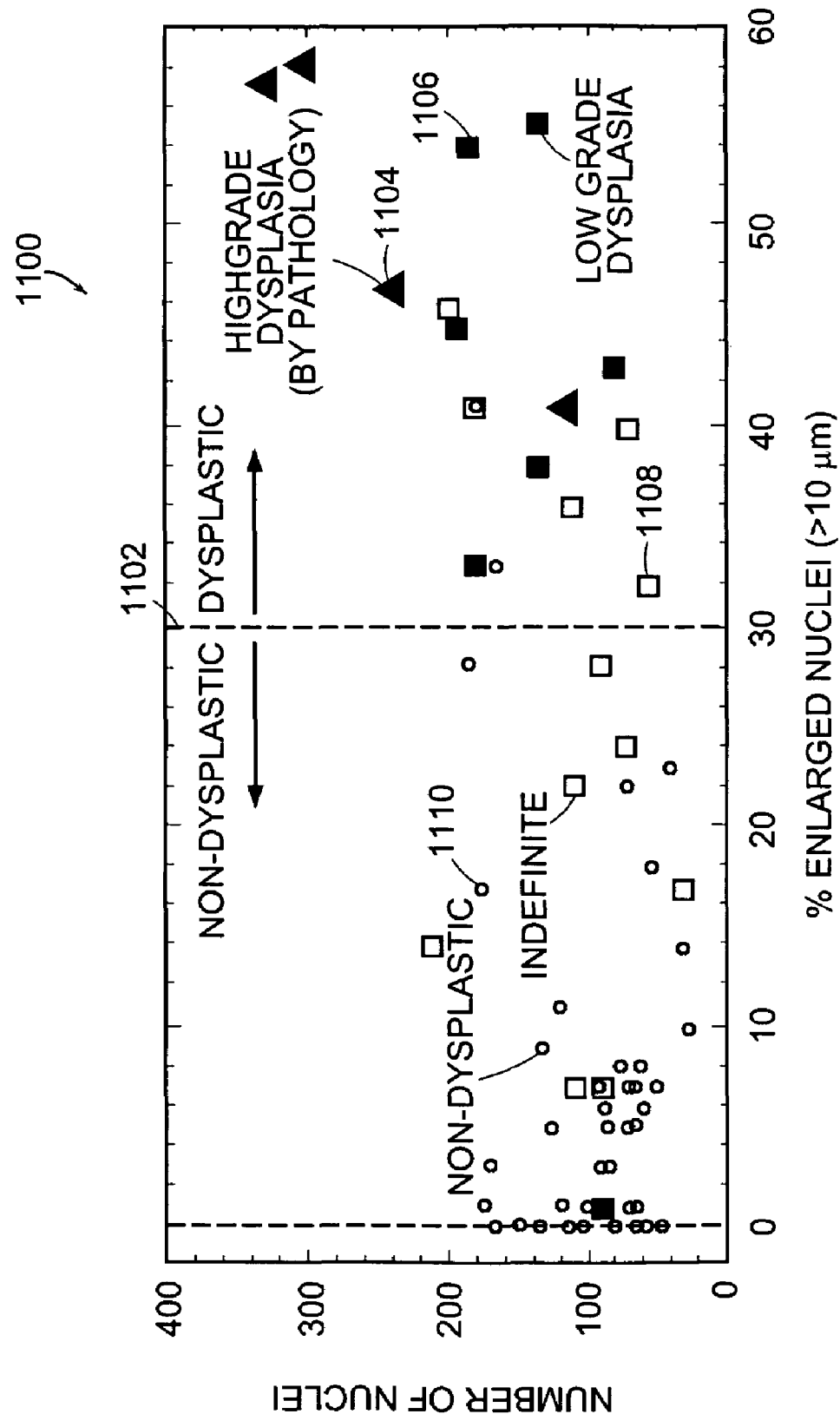
FIG. 11 is a diagram illustrating the results of clinical tests of the LSS technique indicating that dysplasia in Barrett's esophagus can be successfully diagnosed.

Referring to FIG. 11, a plot of the number of cell vs. the percentage of nuclei greater than 10 μm 1100 is shown. An assignment of dysplasia was made if greater than 30% of the nuclei were enlarged (with "enlarged" defined as having a measured nuclear diameter of 10 microns or greater) represented by a dashed dividing line 1102 in FIG. 11. The spectral diagnosis was compared to the average diagnoses using histology determined independently by four expert pathologists in a blind fashion. 874 esophageal sites from 49 patients were examined by histology. Four sites contained high grade dysplasia (HGD) 1104 (represented by filled triangles), 8 sites contained low grade dysplasia (LGD) 1106 (represented by filled squares), 12 sites were indefinite for dysplasia (IND) 1108 (represented by unfilled squares), and the remaining sites were non-dysplastic Barrett's (NDB) 1110 (represented by unfilled circles). A subset consisting of all of the HGD, LGD and IND sites and a random selection of 52 NDB sites were used for comparison of spectroscopy to histology. LSS detected a progressively increasing number of nuclei for epithelium in the categories NDB, IND, LGD and HGD, respectively. The diagnoses of all 76 samples are shown in FIG. 11.

The sensitivity and specificity of LSS for detecting low and high grade dysplasia were 92% and 91%, respectively. All high grade dysplasia sites and 7 of the 8 low dysplasia sites were correctly diagnosed. Use of a multivariate model that incorporates both the number and density of nuclei and the percentage of large nuclei further improved the sensitivity and specificity to 92% and 97%, respectively. Furthermore, inter-observer agreement between LSS and the four pathologists was 76%, better than that obtained by comparing the diagnoses of any one pathologist with the other three (65% on average). This large variation among pathologists is consistent with the literature and illustrates the difficulty in diagnosing this disease.

A practical difficulty in analyzing such spectral data was the need to remove background light due to diffusive scattering through the tissue under the epithelial layer. Typically, this light accounts for about 95% of the total signal. The background light is due to multiple photon scattering events, particularly from smaller structures, such as intracellular organelles, that scatter light more efficiently at large angles. The effective scattering length ranges from 0.1 to 1 μm, depending on wavelength, so that a significant fraction of scattered light will re-enter within the acceptance angle of the probe. This diffuse scattering also picks up spectral features due to absorption processes in the underlying tissue, particularly due to hemoglobin. For the data shown in FIGS. 10A-E the background subtraction was performed off-line by a time-consuming fit of the data to a representation of tissue transport and absorption. The fitting time required for this data was many minutes per point, making it impractical as a real-time measurement.

Figure 12A:
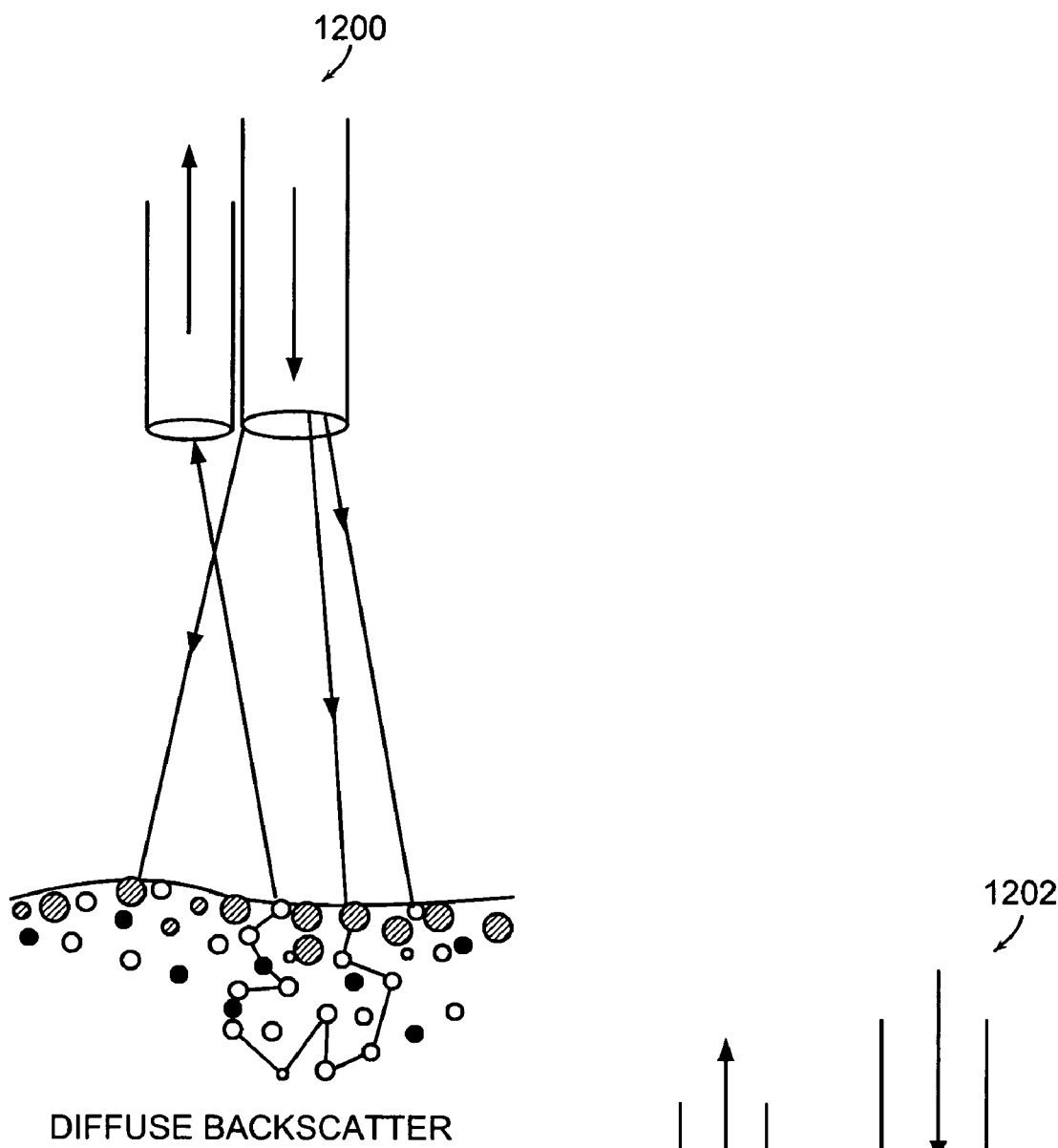
FIG. 12 is a schematic diagram illustrating two types of probe: the probe type shown in 12A receives both backscattered light and diffusely scattered light, while the probe type shown in 12B receives only diffusely scattered light.
Figure 12B:
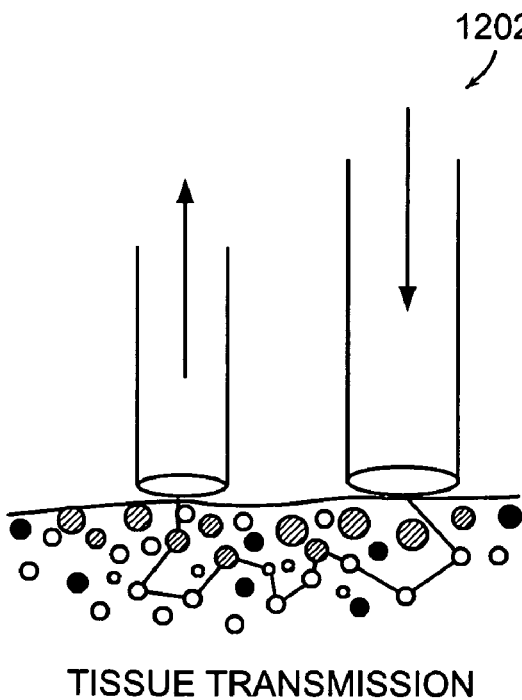

When light diffuses through tissue away from its entrance point, it picks up information on the size distribution of tissue components along its path. The LSS probes 1200 pick up some of this information in the background spectrum as shown schematically in FIG. 12A. Systems have utilized the polarization and spectral characteristics of light exiting turbid media at varying distances from the delivery fiber as a probe for the scattering characteristics of the tissue. A basic probe for this technique can have a geometry 1202 as shown schematically in FIG. 12B. Note that a probe as illustrated in FIG. 12B cannot measure the direct backscatter from cell nuclei as required for an LSS probe. Similarly, a probe as illustrated in FIG. 12B with a very thin window will not be able to measure direct backscatter efficiently.

In a preferred embodiment, the present invention provides a light scattering spectroscopy system to measure the angular distribution and polarization of backscattered light. The characteristics of such systems were studied using tissue phantoms. In this instrument, using a light source and detector system substantially similar to that illustrated schematically in FIG. 1, white light from a xenon arc lamp is filtered (10 nm bandpass), polarized, spatially filtered (<0.25 degree divergence) and collimated to provide a known incident light source. A non-polarizing beam splitter directs the incident light towards the tissue phantom and provides a return path for the scattered light. A lens system focuses the backscattered light onto a CCD detector nominally centered on the optical axis. Such lens systems are described in detail in published PCT applications WO 00/42910, corresponding to U.S. application Ser. No. 09/362,806 filed on Jul. 28, 1999 and WO 00/43750, corresponding to U.S. application Ser.

No. 09/491,025 filed on Jan. 25, 2000, which are incorporated by reference herein in their entirety.

The angle of the backscattered light is converted to an offset from the optical axis in the image. A polarizer in the backscattered light path can be rotated to either observe light with a polarization perpendicular to or parallel to the polarization of the incident illumination. The single-polarizer probe thus has the advantage of automatically removing the background diffuse scattering signal plus the advantage of increasing the frequency of the oscillation from which the diameter of the cell nuclei can be determined.

Figure 13:
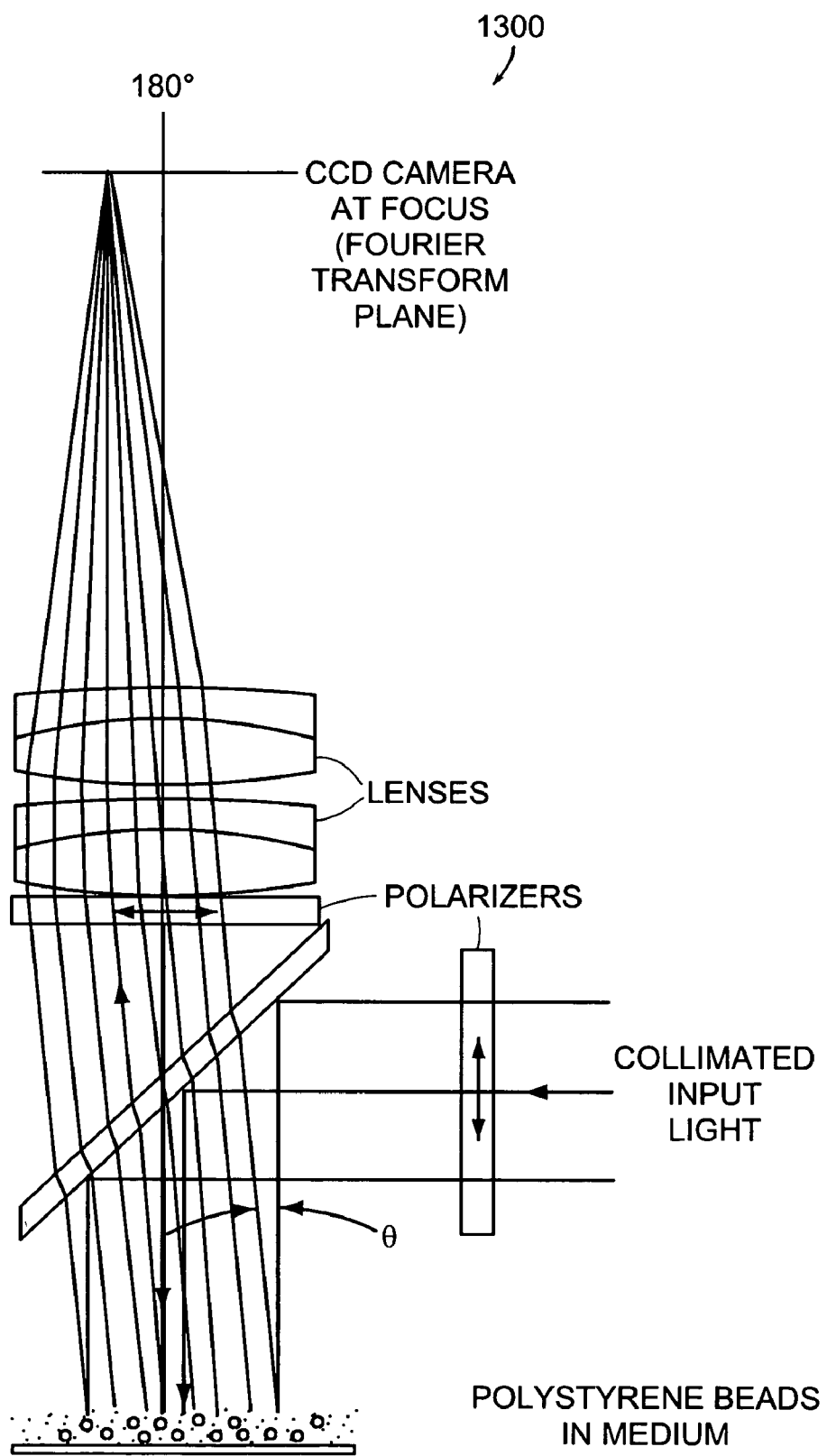
FIG. 13 is a schematic diagram illustrating an imaging LSS instrument suitable for measuring the angular distribution of backscattered intensity near 180 degrees.

In these experiments the individual spectra are obtained simultaneously with a prism spectrometer which disperses the image of an array of fiber tips (the output ends of the receiving fibers) across a CCD detector array, diagramed schematically 1300 in FIG. 13. The absolute calibration of the spectrometer is not particularly critical, but the relative error between spectra must be minimized to obtain a good difference signal. A steep slope in a common-mode spectrum (like the hemoglobin absorption) combined with a relative wavelength calibration error results in an offset in the difference spectrum. This type of error commonly results from field distortions in the imaging optics of the spectrometer. It has been found that such errors can be reduced by introducing deeply modulated light spectra into the spectrometer and minimizing the resulting squares of the difference spectra with a 2-D polynomial mapping function for the spectral error. The modulated light spectrum used was the combined spectra of numerous, evenly-spaced, narrowband filters placed in the illumination light path. By imaging a vertical array of fibers, through the prism, onto the CCD array all of the spectra can be obtained simultaneously. Binning the spectral channels on the CCD chip returns a 7×255 image containing the seven spectra.

Figure 14:
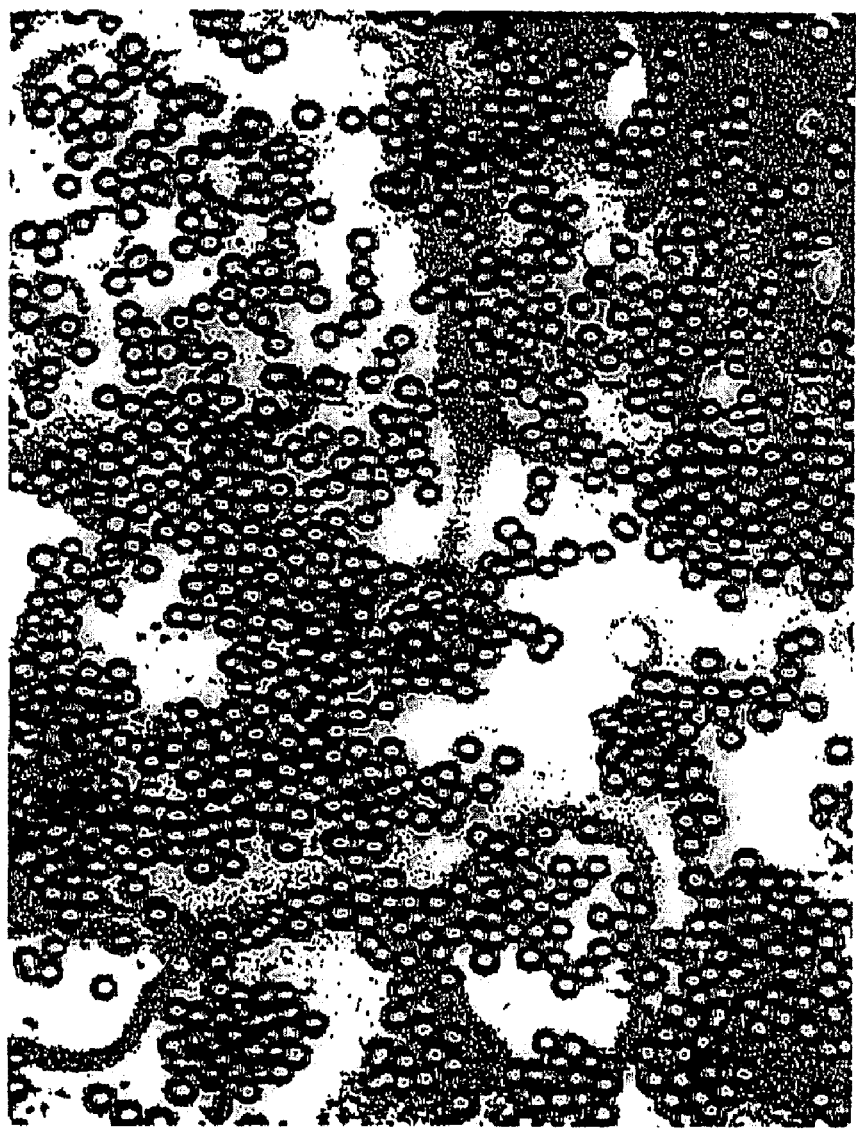
FIG. 14 is a microphotograph of the type of polystyrene beads used in tissue phantoms.

The tissue phantoms are made of polystyrene beads 1400 from Polysciences, Inc. with diameters specified as 4.562±0.209 µm, 9.14±0.709 µm, 14.9±2.21 µm and 21.4±3.21 µm, shown in FIG. 14. These will be referred to as nominal diameters of 5, 10, 15 and 20 µm respectively in the following text. Polystyrene beads have a refractive index, n, of 1.60. This is somewhat higher than cell nuclei, but scattering depends primarily on the ratio of $n_{sphere}$ to $n_{medium}$ which is generally referred to as the scattering variable, m. The value of m for biological tissue is in the range of 1.03 to 1.10. Some of the imaging experiments have been performed with water ($n_{water}$=1.33) as the medium, yielding m=1.203. For a better simulation of tissue, studies have also been performed using Cargille Type FF (Cargille Laboratories, Cedar Grove N.J.), low-fluorescence immersion oil with an index of 1.48 (m=1.081) or Epotex Type 310 optical epoxy with an index of 1.507 to yield m=1.06.

Figure 15:
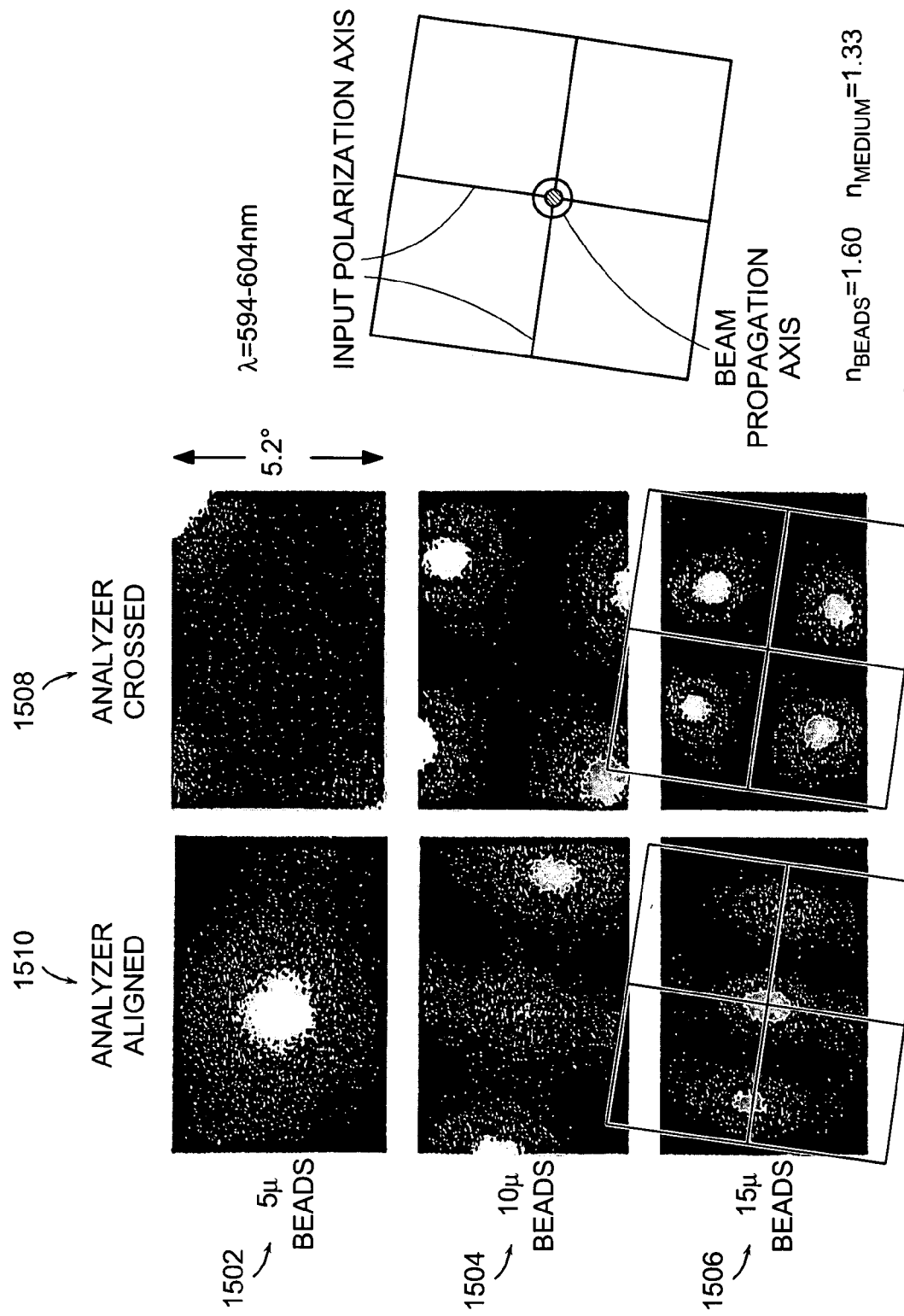
FIG. 15 is a diagram illustrating the angular distribution of backscattered light obtained using polarized illumination and using unpolarized illumination.
Figure 15:
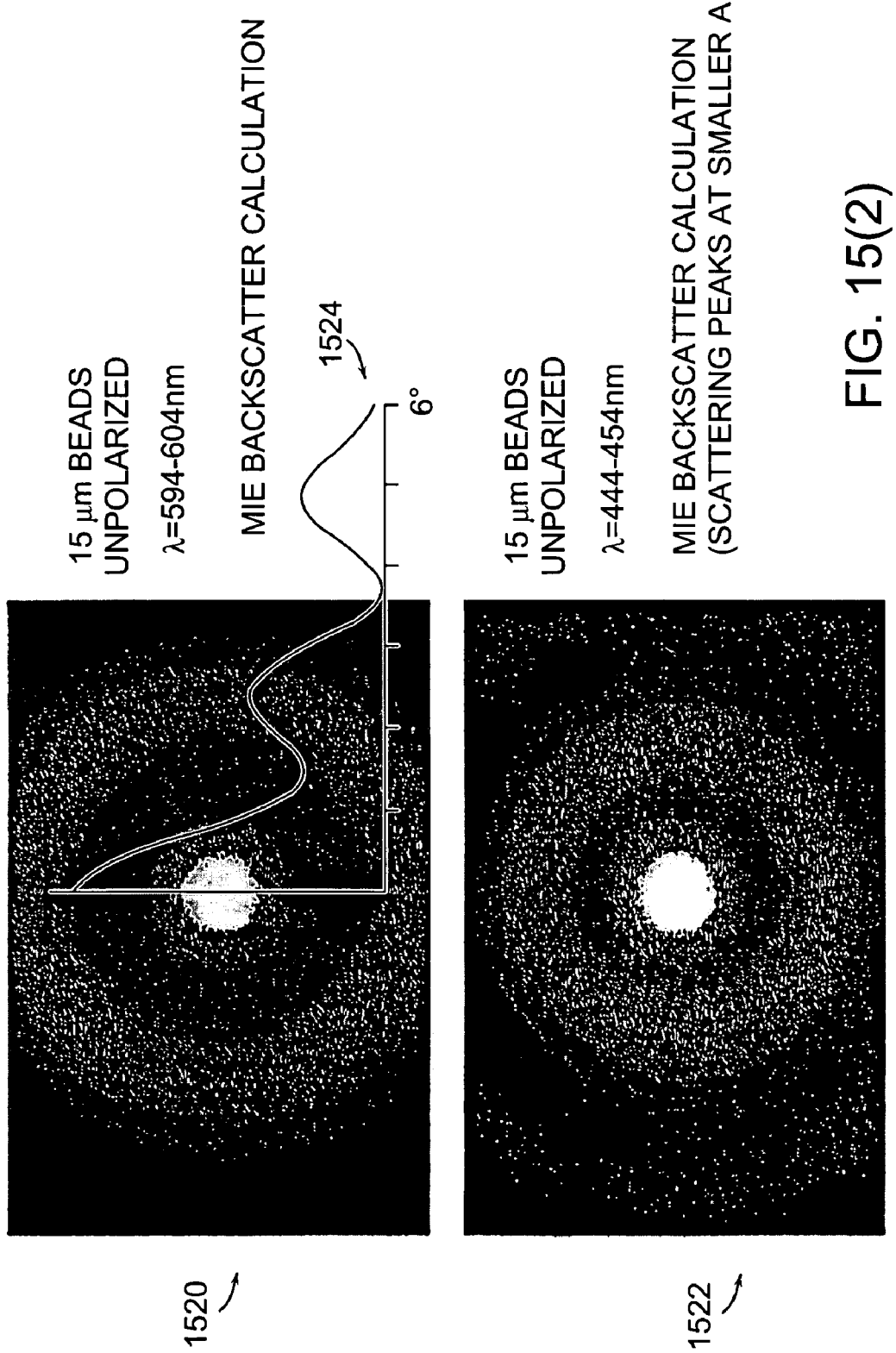

An example of the angular distribution measurements is shown in FIG. 15. The upper panels 1502, 1504, 1506 show the results obtained for polarized light of wavelength 594-604 nm and beads of nominal diameters of 5, 10 and 15 µm. Note the phase relationship of the images obtained with the analyzer crossed 1508 and aligned 1510. The lower panels 1520, 1522 show backscatter patterns obtained with unpolarized light of wavelengths 444-454 nm 1522 and 594-604 nm 1520 and 15 µm diameter beads. A plot of the results of the corresponding Mie backscatter calculation 1524 is overlaid for comparison.

Figure 16:
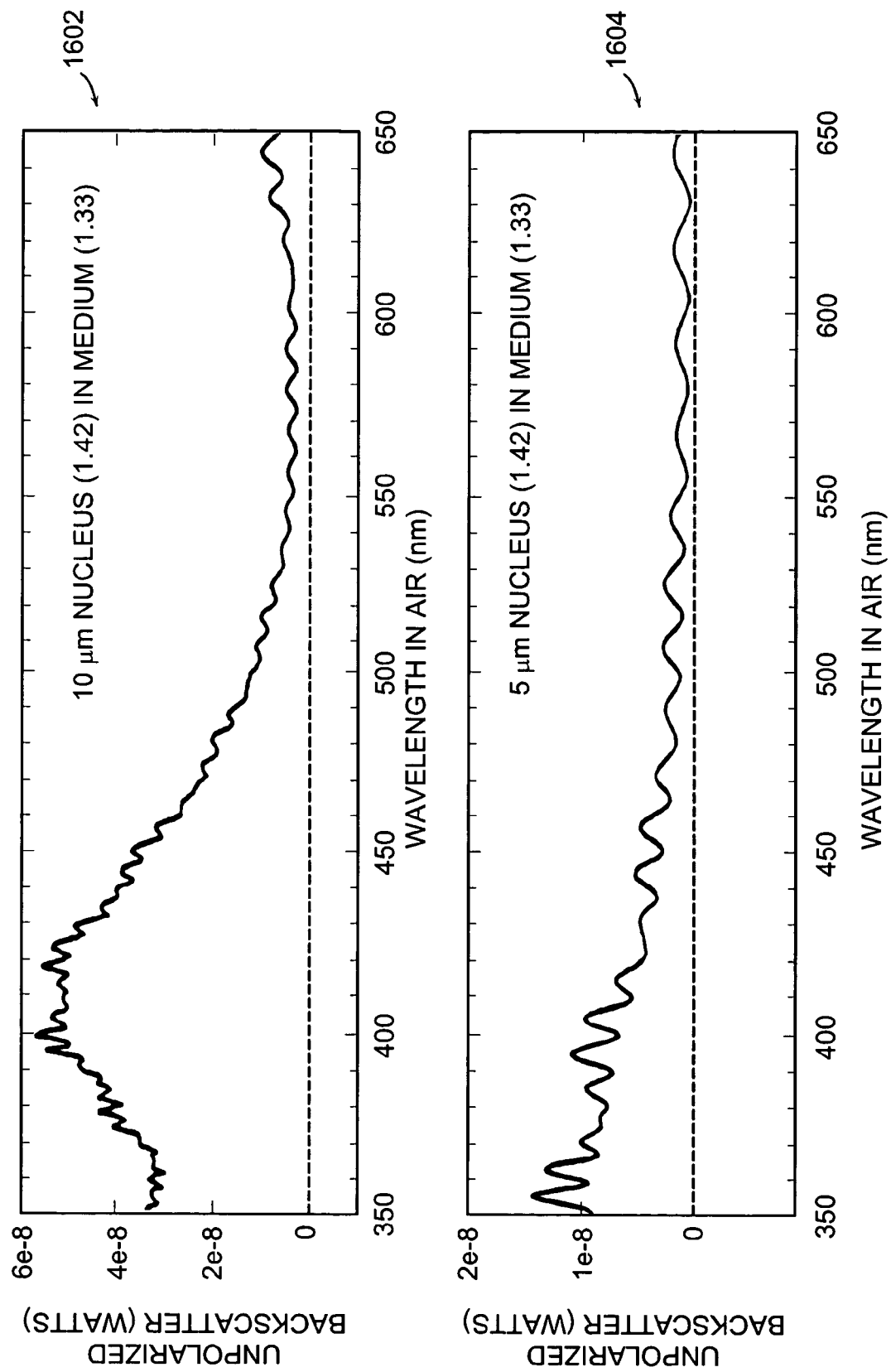
FIG. 16 is a graph illustrating the predicted unpolarized Mie scatter for an unpolarized optical probe with a 100 µm diameter illumination optical fiber and a 50 µm collection optical fiber spaced 350 µm apart behind a 5 mm thick optical window.

An example of the spectra calculated for an unpolarized probe is shown in FIG. 16 for both 5 µm 1604 and 10 µm 1602 diameter cell nuclei with refractive indices of 1.42 in a water medium of index 1.33. The unpolarized optical probe had a 100 µm diameter transmitting fiber optic and a 50 µm receiving fiber optic spaced 350 µm apart behind a 5 mm thick optical window. The analysis method determines the frequencies of the large scale oscillating structures using Fourier analysis and recovers from these frequencies and their amplitudes the size and density of the scattering particles (the nuclei). These predicted backscattered spectra have fine structure with a width of less than 10 nm, an intermediate structure with a width of about 50 nm and a large scale structure at the scale of the full visible wavelength range.

Figure 17:
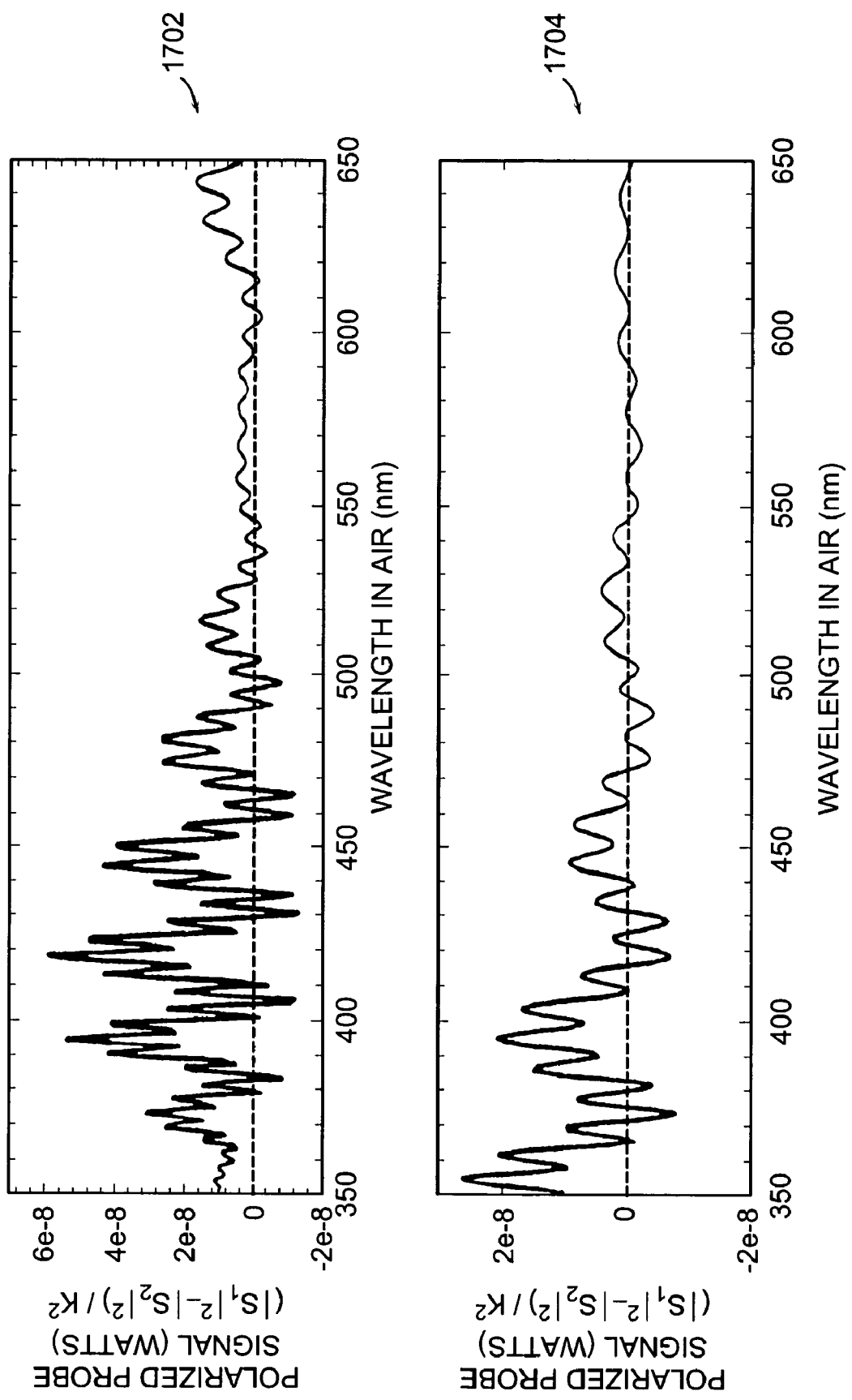
FIG. 17 is a graph illustrating the predicted spectra based on polarized Mie backscatter, for 10 µm (upper panel) and 5 µm (lower panel) cell nuclei, to be acquired using the improved fiber-optic probe.

FIG. 17 shows the predicted difference spectrum from the single-polarizer optical probe design for both 5 µm 1702 and 10 µm 1704 diameter cell nuclei. Note that the low frequency information has been removed, and that the intermediate frequencies and high frequencies in the spectral oscillations are enhanced compared to the case of the unpolarized probe. Experimental data taken with polystyrene beads and a prototype polarized probe verified that these predicted spectra are obtained experimentally, and are in good agreement. The intermediate frequency in the backscattered spectrum clearly increases with increasing scattering particle diameter. The cell nuclei in real tissue exhibit a range of diameters, so their reflectance spectrum is not represented by simple oscillations, but rather a linear combination of such spectra depending on the particle size distribution.

A polarized probe used in measurements was scaled up by a factor of 4 from the nominal 2.4 mm diameter practical for probes used in endoscopes. The optical performance of the probe is invariant with scale in terms of the backscattered spectrum that it returns. This probe was used to measure the spectra that are obtained with a relatively small range of backscattered light collection angles. The illumination optical fiber used in this particular 4× scaled probe is 400 µm in diameter with collection optical fibers which are 200 µm in diameter. The results are representative of those to be obtained from this probe with 100 µm diameter illumination optical fiber and 50 µm diameter collection optical fibers. Note, however, that the collection of the diffuse scattered light from deeper in tissue depends on the characteristic scattering distance in that tissue and is thus not invariant to scale. Comparisons between direct backscatter and diffuse scatter are properly made only with a 1× probe.

Seven spectra obtained with the 4× scaled single polarizer optical probe were analyzed in detail. Three of the spectra were for a backscattered angle of 4 degrees and four were for an angle of 8 degrees. A single polarizer covered the illumination fiber, three of the 4 degree collection fibers and three of the 8 degree collection fibers. A second polarizer, oriented at 90 degrees to the first polarizer, covered the fourth fiber at the 8 degree backscatter angle. The 4 and 8 degree collection fibers under the single polarizer were positioned so that their spectra represented return light scattered perpendicular to the polarizer axis (s), parallel to that axis (p) and at 45 degrees to that axis.

The spectra returned into the 8 degree angle were weaker than the 4 degree spectra and exhibited different oscillations, all as predicted for the probe.

The crossed polarizer optical probe, as expected, returned spectra for light that had been depolarized by the illuminated surface. Some surfaces, such as white Spectralon and hand tissue, depolarize light fairly well. These surfaces are translucent and the light transmitted into the surface undergoes many out-of-plane reflections before emerging from that surface. Other materials, such as partially-absorbing Spectralon and suspensions of beads in water, do not depolarize the light completely. The light reflected from these surfaces has undergone fewer internal scattering events and is predominately polarized in the plane of the illuminating light. It should be noted that the use of a cross-polarized light signal for background subtraction will not work properly unless the underlying tissue depolarizes the light well. The single-polarizer design for background subtraction does not suffer from this limitation.

Figure 18:
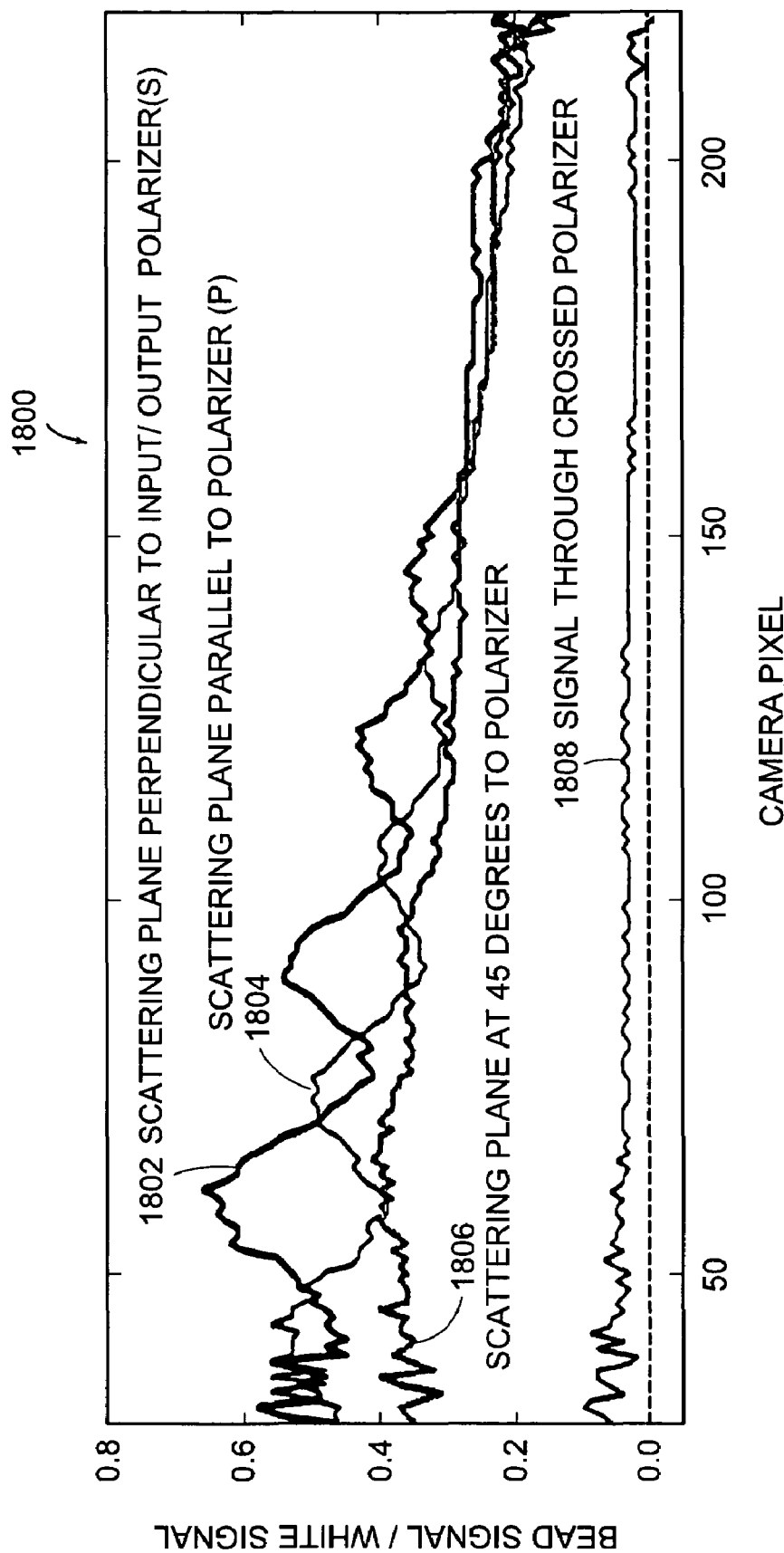
FIG. 18 is a graph illustrating the polarized backscatter spectra measured using a scaled LSS probe from a tissue phantom of polystyrene beads in an index-matching medium designed to simulate cell nuclei.

The spectra 1800 in FIG. 18 show the backscattered spectra acquired from a suspension of 9.14±0.709 µm polystyrene beads in optical epoxy. The ratio of bead refractive index to epoxy index is 1.06 so that the scattered spectrum is similar to that of 9 µm cell nuclei in epithelial tissue. The features to note are that the mid-frequency oscillations in the spectrum of light scattered perpendicular to the plane of the input polarization (s) 1802 are out of phase with the oscillations in the spectrum of light scattered parallel to the plane of the polarization (p) 1804. The lowest spectral frequencies form the slope in the spectrum which is common to both the s and p signals. The light scattered at 45 degrees 1806 has no mid-frequency oscillations and is thus similar to the unpolarized spectrum 1808. The backscattered light is also strongly polarized, as expected, as shown by the low signal in the crossed polarizer spectrum. Subtracting the p spectrum from the s spectrum removes the slowly varying background and any depolarized return light. The signal through the crossed polarizer is very low since there is no additional layer beneath the beads to simulate diffuse backscatter.

Figure 19:
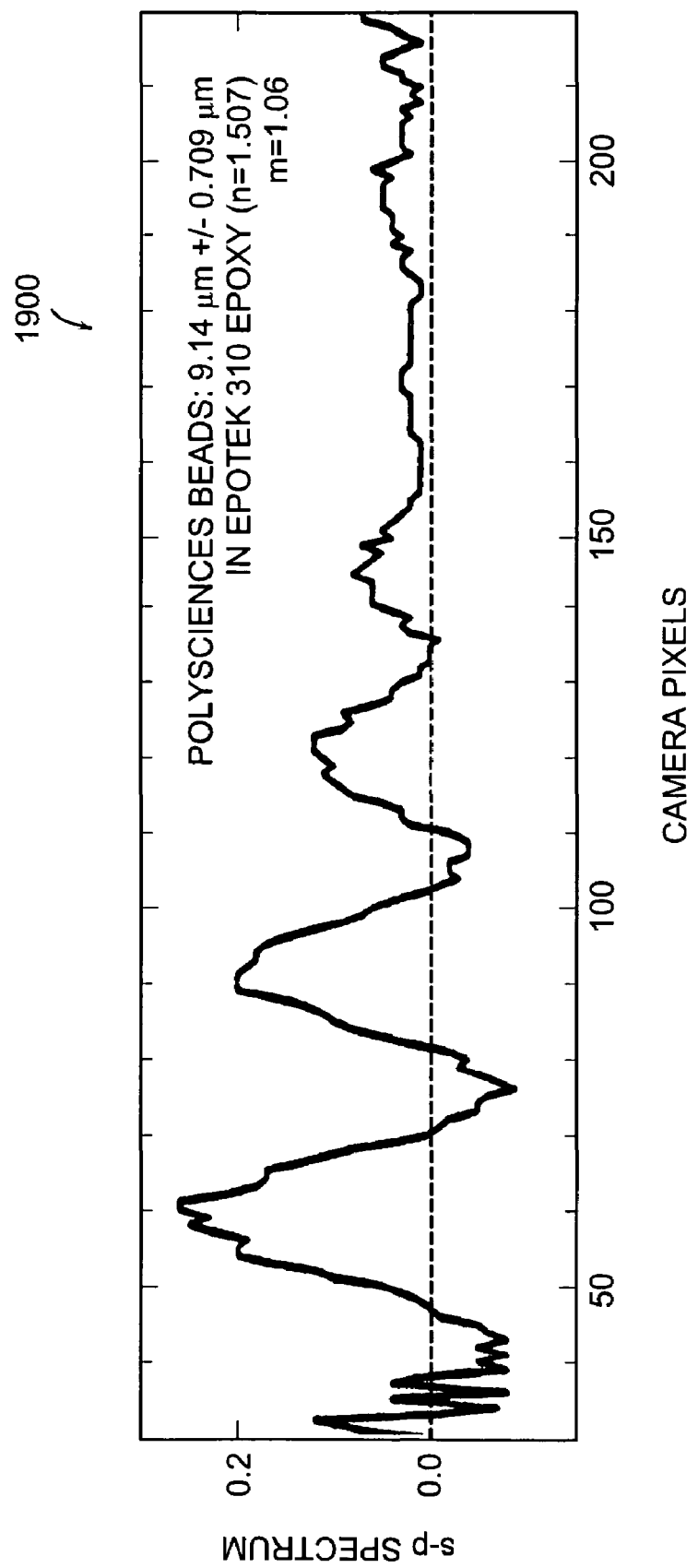
FIG. 19 is a graph showing that the difference spectrum, calculated as s minus p, exhibits little low frequency Mie backscatter or background light.

Notice that the intermediate frequency ripples in the s and p polarized spectra are out of phase. Also note that the high frequency ripples, present in the modeled data, are washed out due to the low resolution of the spectrometer. By subtracting the p-signal from the s-signal, 1900 the low frequency and diffuse backscatter components can be eliminated, as is shown in FIG. 19. Small differences in the collection efficiency of the two fibers results in a small DC component which can be taken out by applying a scaling factor to one of the spectra.

Figure 20:
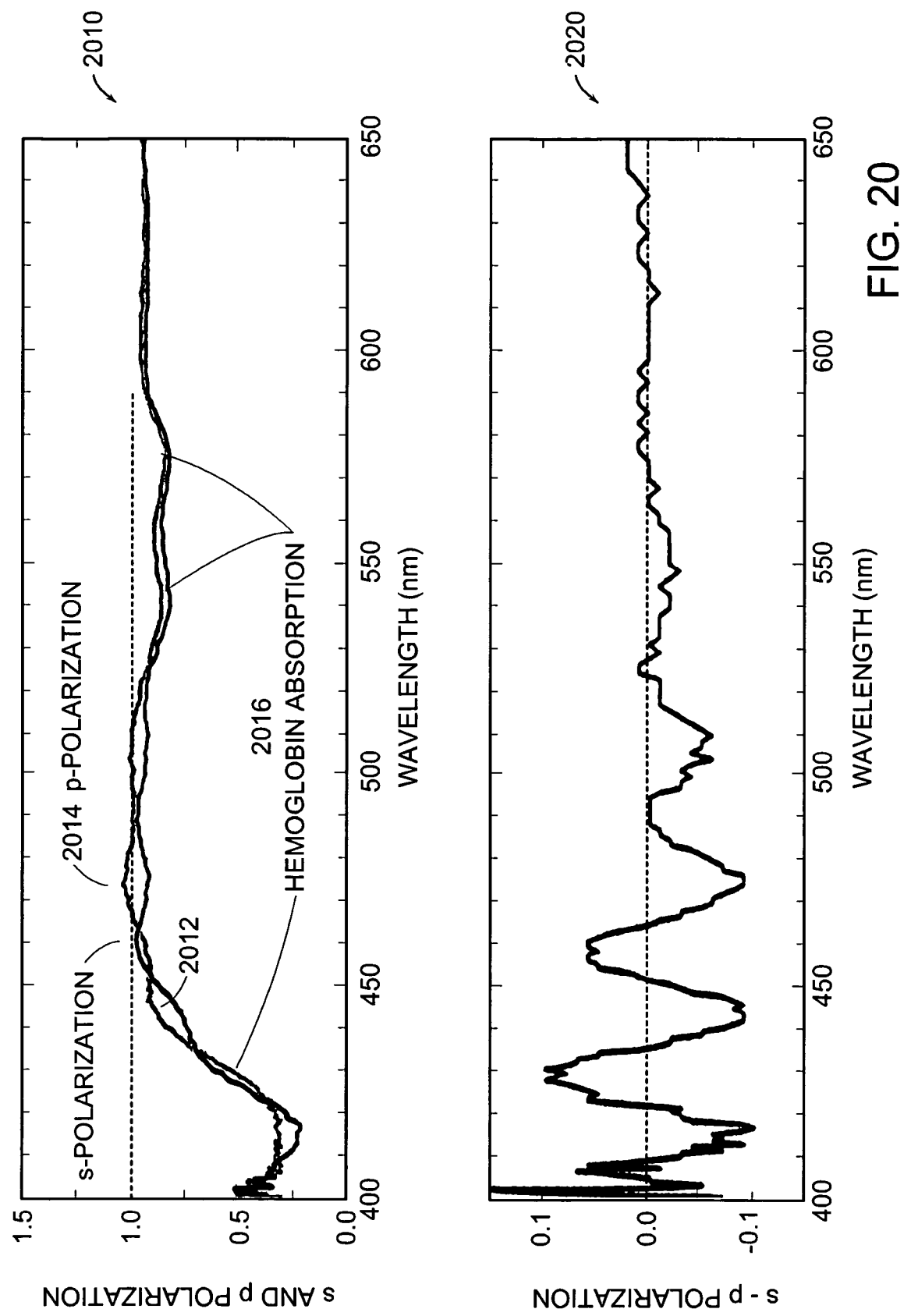
FIG. 20 is a graph showing the results of an experimental measurement of a polystyrene bead tissue phantom which includes a diffuse scattering sublayer with dissolved hemoglobin.

The upper graph of FIG. 20 shows the spectrum 2010 from a polystyrene bead layer over a sublayer of very fine barium sulfate particles suspended in water to which a small amount of hemoglobin has been added including both the s-polarization spectrum 2012 and the p-polarization spectrum 2014. The lower graph of FIG. 20 shows the resultant spectrum after s-p subtraction 2020. The hemoglobin (hemoglobin-$A_0$, ferrous, SIGMA) produced the dips in the spectrum at 415, 540 and 570 nm as observed 2016 in clinical tissue spectra. This background light was generally polarized in the same plane as the illumination, but the s-p subtraction method still removes it.

Figure 21:
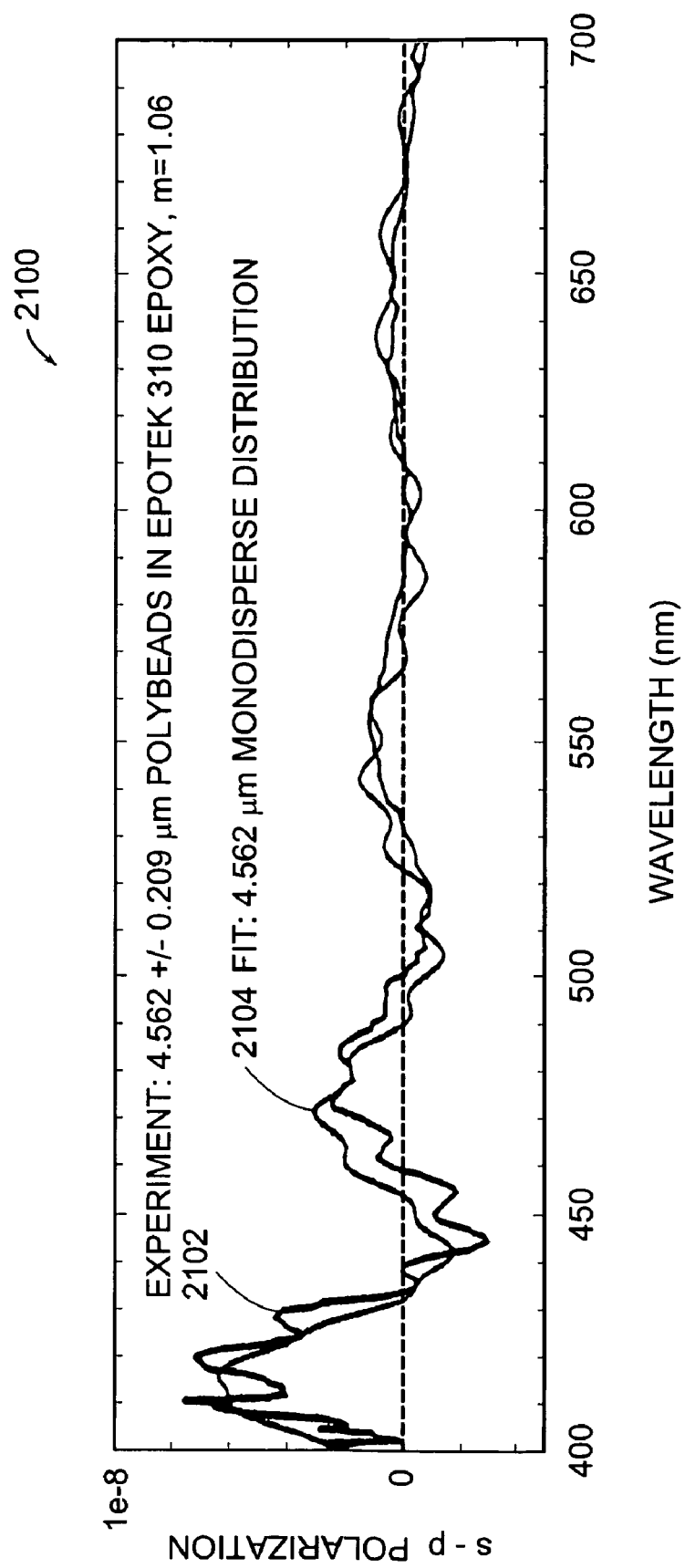
FIG. 21 is a graph showing difference spectrum of light backscattered from polystyrene beads compared to a theoretical calculation for spheres of the same central diameter.

FIG. 21 shows difference spectra 2100 for a suspension of 4.5 µm polystyrene beads in Epotek 310 epoxy, where m=1.06, 2102 compared to a theoretical model 2104 of the expected Mie backscatter assuming a single bead diameter (monodisperse distribution) of 4.562 µm. The fit is good, in that both the phase and amplitudes of the predicted intermediate and high frequency oscillations match the experiment. A linear, chi-square minimization program has been written to fit a basis set of spectra, distributed over a range of diameters, for a particular probe design. The program is not iterative and is thus very fast, but it can only fit diameters or diameter distributions for which it has stored spectra. A practical analysis method for a clinical LSS instrument, however, needs to be able to return a distribution of diameters.

Figure 22:
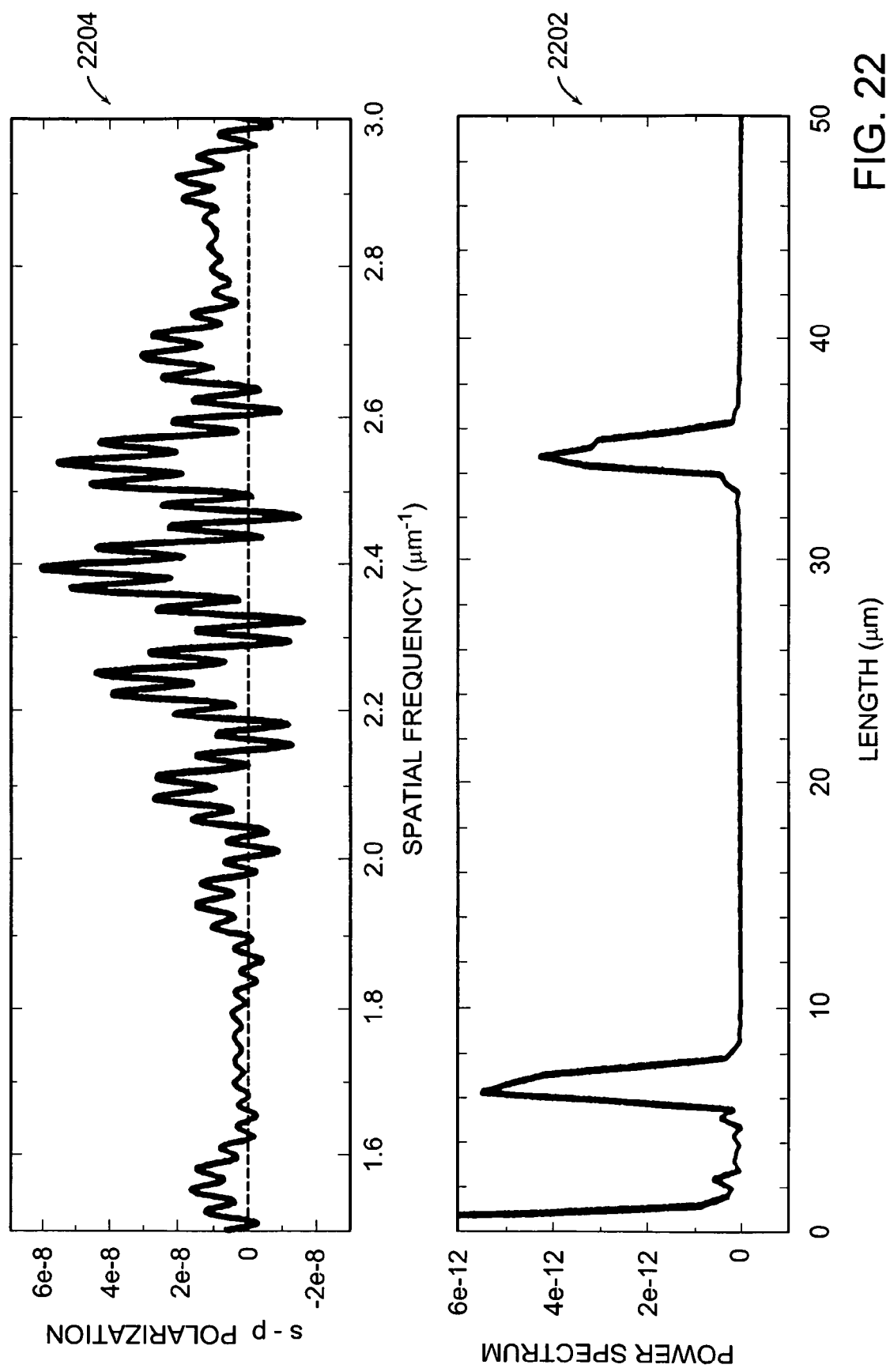
FIG. 22 is a graph showing the predicted s-p signal from a suspension of 10 µm beads (upper panel, FIG. 22A) and a FFT (lower panel, FIG. 22B) showing the frequency of the oscillations.
Figure 23:
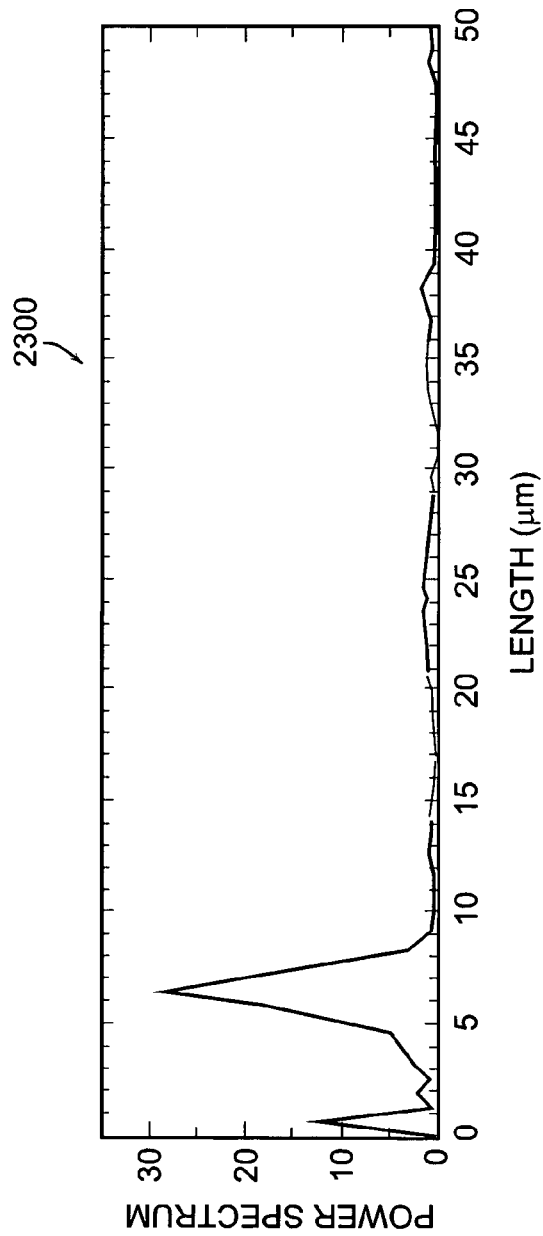
FIG. 23 is a graph showing the FFT of experimental data from 9.14 µm polystyrene beads.

A better analysis method for a clinical instrument is to extract the frequency of the oscillations from the spectra with a Fourier transform technique. The power spectrum 2202 of a predicted spectrum for 10 µm particles, for example, is shown in FIG. 22. The intermediate and high frequency peaks are easily quantified. FIG. 23 shows the fast fourier transform (FFT) of the experimental polystyrene bead data shown in FIG. 19. The high frequency oscillations in this case are above the resolution of the spectrometer, so they are not present in the power spectrum.

The calculated spectrum 2204 shown in FIG. 22 is plotted in inverse wavelength space with the units of 1/µm for convenience. Diffraction (and thus Mie scatter) is generally described by terms involving a multiple of a characteristic length divided by the wavelength of the light being diffracted. The spectral oscillation peaks are thus evenly spaced when plotted against $1/\lambda$. The Fourier transform of an oscillation with evenly spaced peaks in $1/\lambda$ space is a delta function at a characteristic length, L, in $1/(1/\lambda)$ space with units of µm. The peaks in the Fourier transform correspond to a scaled particle size (µm) with a scaling factor which can be determined from the program used to predict the Mie backscatter for a particular probe. The FFT peaks are narrow with a position which is a linear function of particle diameter over the range of interest 2300 as is shown in FIG. 23. The FFT can thus return the size distribution directly.

Figure 24:
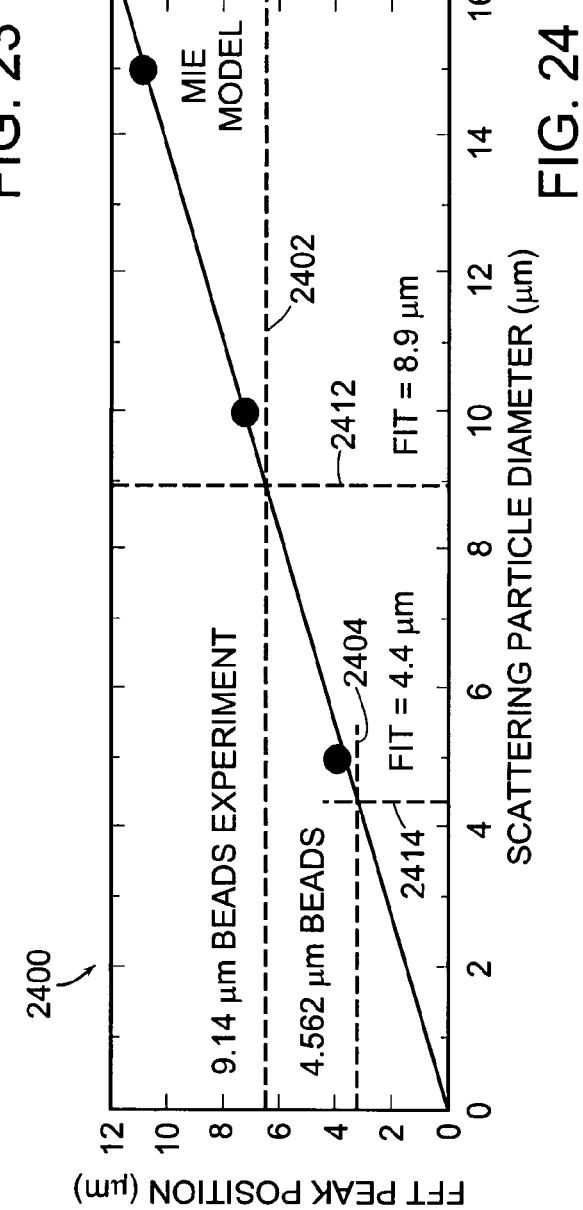
FIG. 24 is a graph showing the Fourier transform peak positions from predicted spectra (solid dots) are fit to a linear scaling constant which correctly determines the size of scattering particles in the experimental data from the Fourier transforms of the corresponding difference spectra.

FIG. 24 is a graph showing the Fourier transform peak positrons for predicted spectra fit to a linear scaling constant 2400. The horizontal dashed lines 2402, 2404 in FIG. 24 are the positions respectively of the FFT peaks for the experimental data taken with the 9.14±0.71 µm and 4.56±0.21 µm beads. The predicted diameters from the FFT analyses, horizontal dashed lines 2412, 2414, are well within the size distribution for these beads as specified by the manufacturer.

Figure 25A:
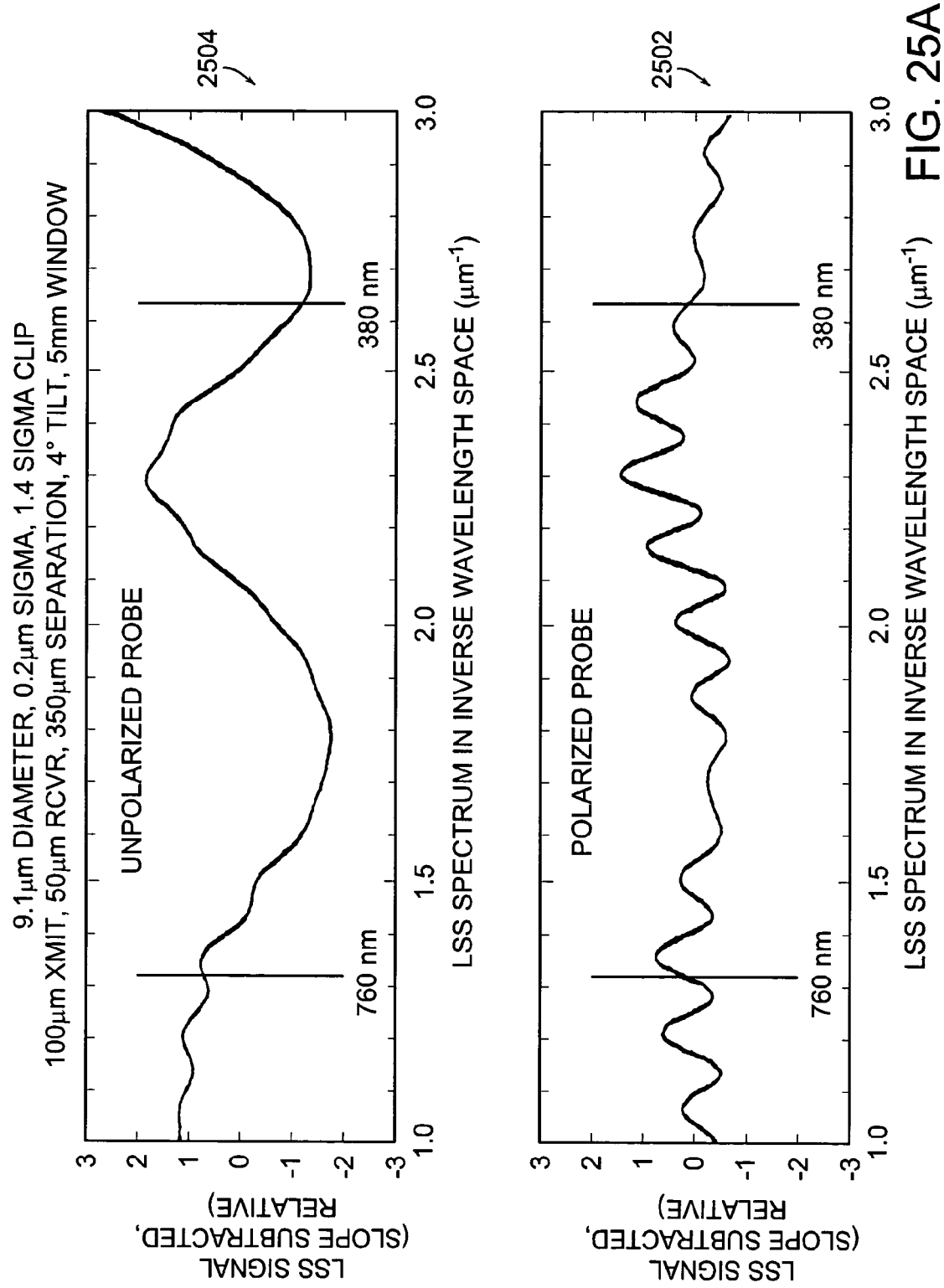
FIG. 25 is a set of graphs illustrating an example of spectra predicted for a population of particles having a broader size distribution, comparing the results predicted for an unpolarized light optical probe and a polarized light optical probe showing the LSS spectra plotted in inverse wavelength space (FIG. 25A) and the corresponding FFT (FIG. 25B)
Figure 25B:
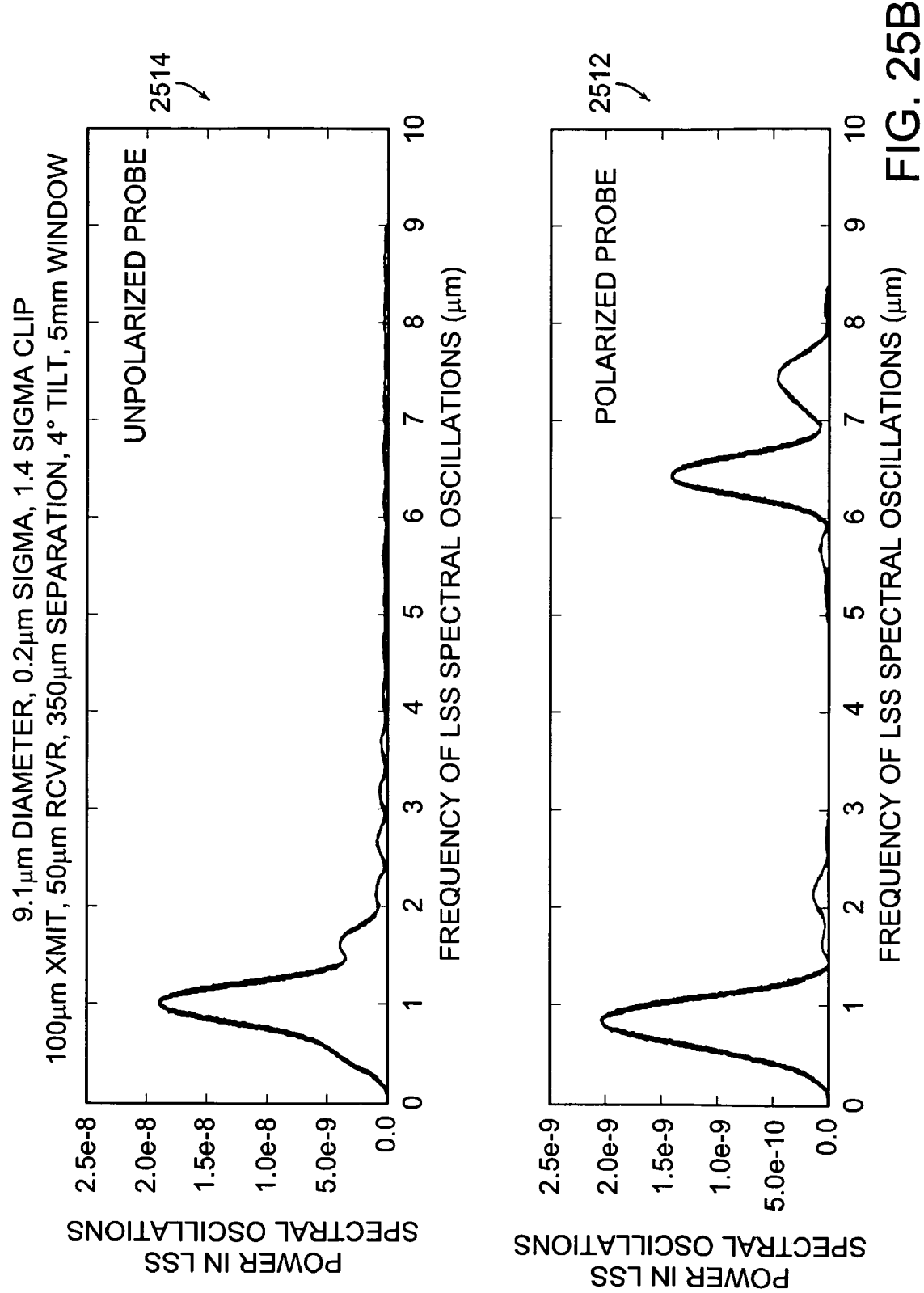

As can be seen in the comparison of the nuclear diameter distributions 1030 of normal colon cells 1033 and T84 tumor colon cells 1036 in FIG. 10C, it can be expected that the nuclei of dysplastic or tumor cells may differ in distribution breadth (expressed in these studies as sigma) as well as in average diameter. It has been found that the single polarized optical probe has characteristics that are an improvement over those of an unpolarized optical probe that are useful for broader distributions of nuclear diameters. FIGS. 25A-B compare the representations for single polarized optical probe 2502, 2512 and unpolarized optical probe 2504, 2514 for narrow distribution with a center at 9.1 µm diameter a sigma=0.2, and a 1.4 sigma clip for a probe with a 100 µm diameter central illumination fiber, 500 µm diameter collection fibers with 350 µm separation tilted at 4° and a 5 mm diameter window. The spectra are plotted in inverse wavelength space (FIG. 25A) 2502, 2504 and FFT (FIG. 25B) 2512, 2514. The high frequency oscillations and improved signal to noise characteristics of the single polarized optical probe were seen as described above.

Figure 26A:
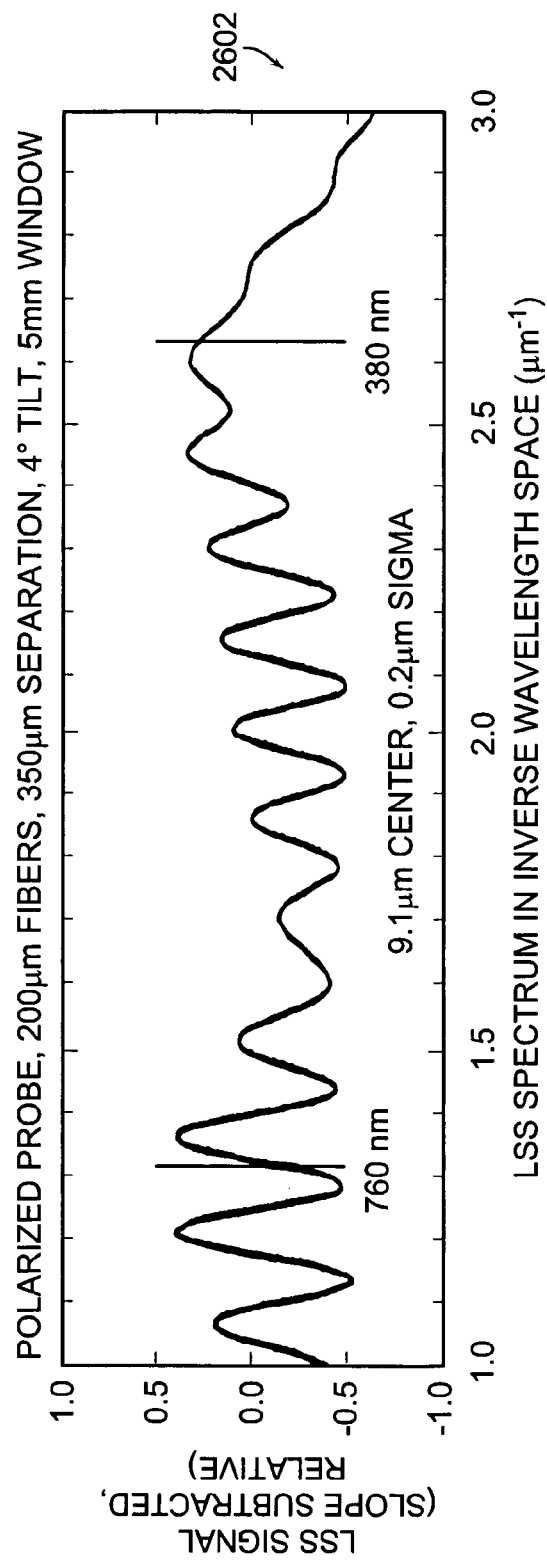
FIG. 26 is a set of graphs comparing spectra predicted for a population of particles having a narrow size distribution (mean=9.1 µm, sigma=0.2 µm) to those for a population of particles having a broader size distribution (mean=9.1 µm, sigma=1.0 µm) for a polarized light optical probe showing the LSS spectra plotted in inverse wavelength space (FIG. 26A) and the corresponding FFT (FIG. 26B)
Figure 26A:
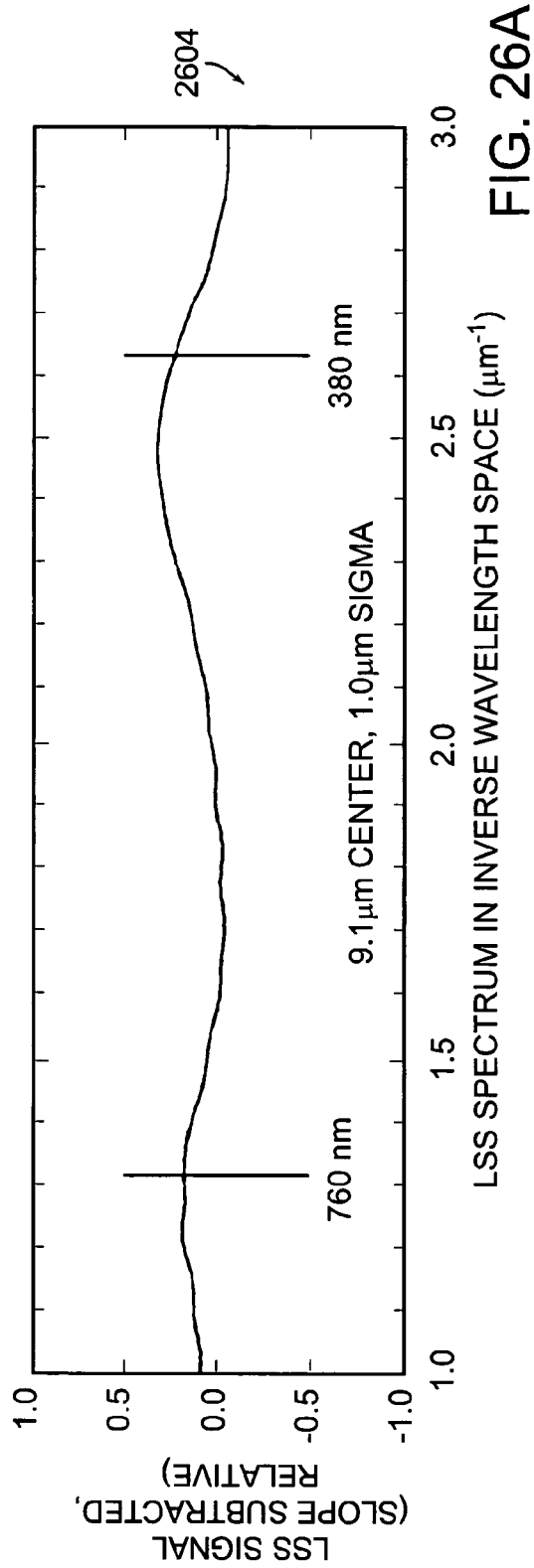
Figure 26B:
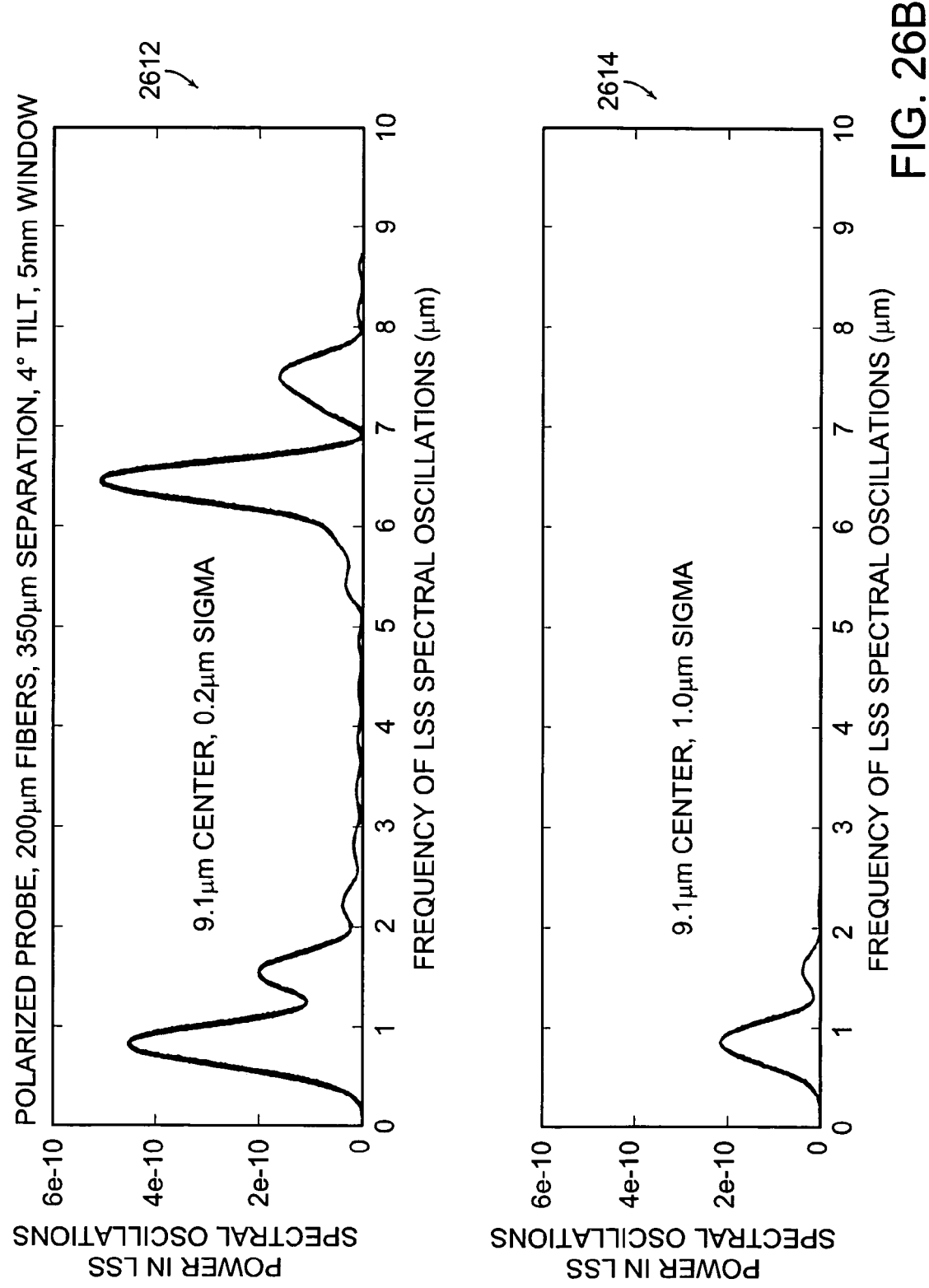

FIG. 26 compares the representation for single polarized optical probe for the same narrow distribution with sigma=0.2 2602, 2612 and a five-fold broader distribution with sigma=1.0, 2604, 2614 plotted in inverse wavelength space (FIG. 26A) 2602, 2604 and FFT (FIG. 26B) 2612, 2614. While the high frequency oscillations are reduced for broader distributions, and the improved signal to noise characteristics of the single polarized optical probe leads to the conclusion that the ability to identify the mean nuclear diameter is not compromised by a five-fold increase in the breadth of the size distribution.

Figure 27:
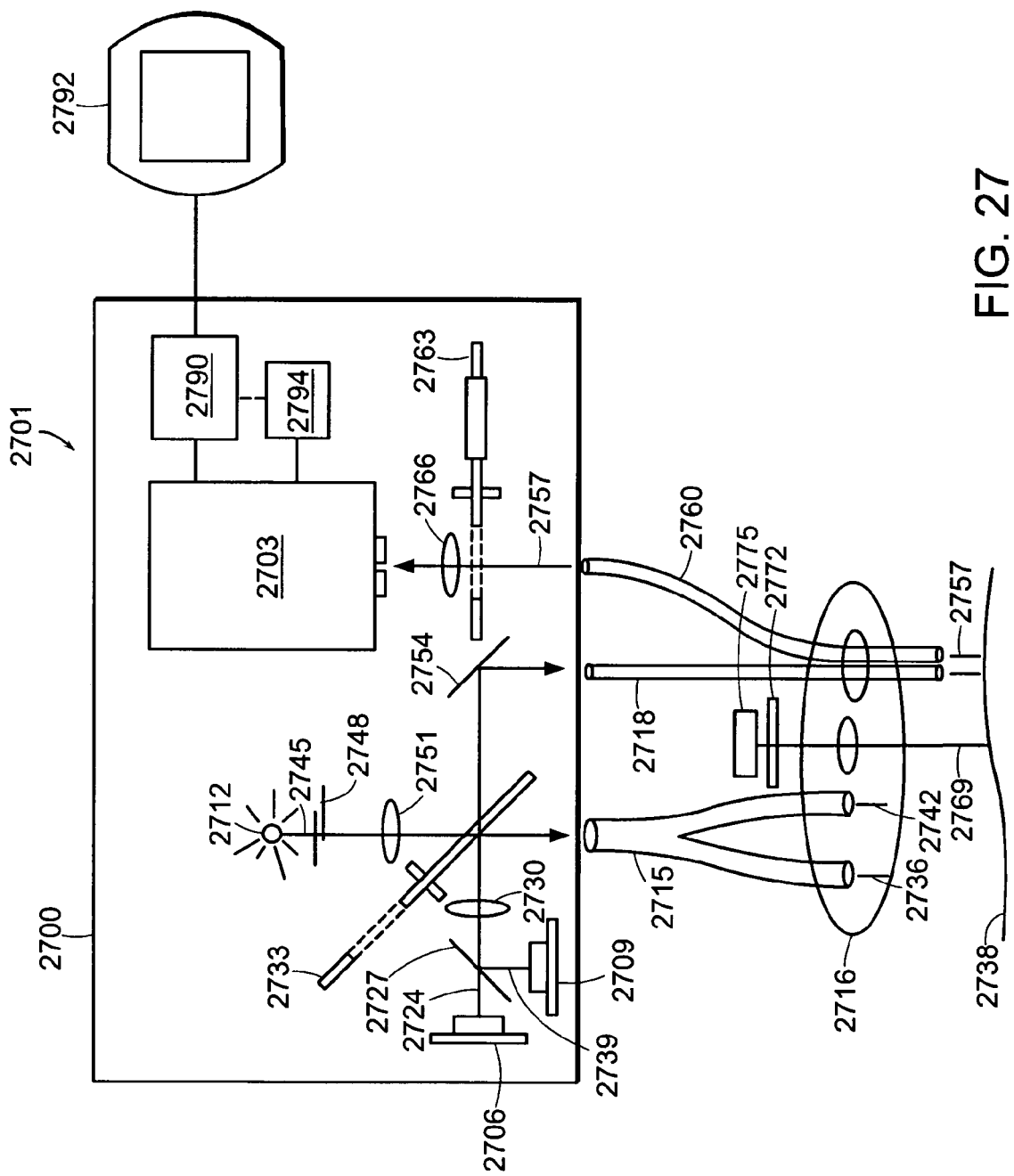
FIG. 27 is a schematic diagram of another embodiment of a light source and detector system for a light scattering spectroscopic system.

Referring to FIG. 27, another embodiment of a light source and detector system 2700 for both a light scattering spectroscopy system and the optical probes of the present invention is schematically shown 2701. The imaging system (light source and light collection fibers) provides a large area survey and the spectrometer system provides a detailed spectral measurement at a point. The spectrometer facilitates obtaining a more detailed spectrum from a small area on the tissue and thus a more precise estimate of the probability of dysplasia.

In one embodiment, light is provided by two laser sources 2706, 2709, and an illumination lamp 2712, such as, for example, a xenon (Xe) lamp, or a mercury (Hg) lamp optimized for broadband illumination. Preferably, the first laser source 2706 comprises a solid state laser providing UV/violet light, such as, for example, a gallium nitride laser diode operating at wavelengths in the range of 380 nm to 420 nm, and more preferably at about 405 nm. Preferably the second laser source comprises a solid state operating in the red, such as, for example, a diode laser operating at wavelengths in the range of 630 nm to 670 nm, such as, for example, an AlGaInP laser diode, and more preferably at about 650 nm.

In another embodiment, the light source comprises a laser diode operating in the red (e.g., from about 630-670 nm) a laser diode operating in the green (e.g. from about 500-550 nm), and a laser diode operating in the violet (e.g. from about 380-460 nm). In one version, the red, green and violet laser diodes are operated to provide both "white light" to serve as an illumination light source and excitation light. For example, corrected broadband illumination ("white light") can be provided by controlling the intensity and bandwidth of the light that reaches the tissue from each the three laser diodes. Excitation light could, e.g., then be provided by the violet laser diode, by frequency doubling the light from the red laser diode (e.g., with a $KTiOPO_4$ (KTP) crystal), or both, to provide one or more excitation wavelengths.

For imaging and obtaining IFS, the beams 2724, 2739 from the two lasers 2706, 2709 are combined into a single beam 2713 with a dichroic mirror and collimated by a lens (or system of lenses) 2730. A shutter mirror on a shutter wheel 2733 (the rotary position shown) and lens 2730 focus the combined beam 2713 onto the end of the illumination bundle 2715 of an endoscope 2716. The illumination bundle 2713 bifurcates at the distal tip of the endoscope 2716 into two bundles 2736, 2742 to illuminate the tissue 2738. Light from the tissue 2769 as a result of the illumination is detected with a color CCD chip 2775 at the distal tip of the endoscope 2716. The color CCD chip 2775 is covered with a blocking filter 2772 to block excitation light (e.g., a 405 nm long pass filter to block the light from a first laser comprising a laser diode operating at 405 nm). The blue sensitive elements of the CCD chip record tissue fluorescence and the red elements of the CCD chip record a red reference spectrum. Alternatively, the different images can be acquired in sequence using sequential illumination at each color. The fluorescence and red reference spectra can then be combined to produce an IFS spectrum that can be presented, for example, as a false-color image to facilitate determining regions of dysplasia.

In one preferred embodiment, the first laser comprises a laser diode operating at 405 nm, the second laser a laser diode operating at 650 μm, and the illumination lamp a Xe lamp. The light source and detector system 2700 can be operated as follows for TMS. For TMS, the shutter wheel 2733 is positioned to alternately: (1) reflect the broadband illumination ("white light") 2745 from the lamp 2712, collimated by a lens (or lens system) 2751 onto a reflector 2754, into the delivery fiber 2718 and onto the tissue 2738; and (2) transmit the 405 nm diode laser light onto a reflector 2754, into the delivery fiber 2718 and onto the tissue 2738. During the transmission of the 405 nm light the 650 nm laser light is stopped, e.g., by turning off the 650 nm laser and/or blocking its light.

Collection optical fibers 2760 in the probe 2716 carry light 2757 from the tissue 2738 back to a spectrometer 2703 in the system 2700. To record a fluorescence spectrum, when the 405 nm laser light is on the tissue, a rotary filter wheel 2763 places an excitation wavelength blocking filter (here a 405 nm long pass filter) in the collected light's 2757 path and the light is collimated by a lens (or system of lenses) 2766 into the spectrometer 2703. During fluorescence measurements the "white light" from lamp 2712 is stopped (e.g., by turning off the lamp or, more preferably, by a fast shutter 2748 in front of the lamp 2712 that allows its light to be blocked without turning off the lamp). To record a reflectance spectrum, when the "white light" is on the tissue the rotary filter wheel 2763 places a hole (no filter) in collected light's 2757 path (the rotary position shown) and the light is collimated by a lens (or system of lenses) 2766 into the spectrometer 2703.

In another embodiment, that can be also applied to the system illustrated in FIG. 1, the broadband illumination may be stopped from reaching a spectrometer by a shutter placed in front of the entrance slit to the spectrometer, that is phase locked to a filter wheel so that as the filter wheel turns the shutter opens only during dark read periods of the imaging sensor (e.g., a CCD).

Still another embodiment of a light source and detector system for a both a light scattering spectroscopy system and the optical probes of the present invention is shown schematically in FIGS. 28A-D, which present different views of one embodiment of operating the system. As illustrated in FIGS. 28A-D, lamps are used as light sources, however, any suitable light source, including laser sources, can be used.

Figure 28A:
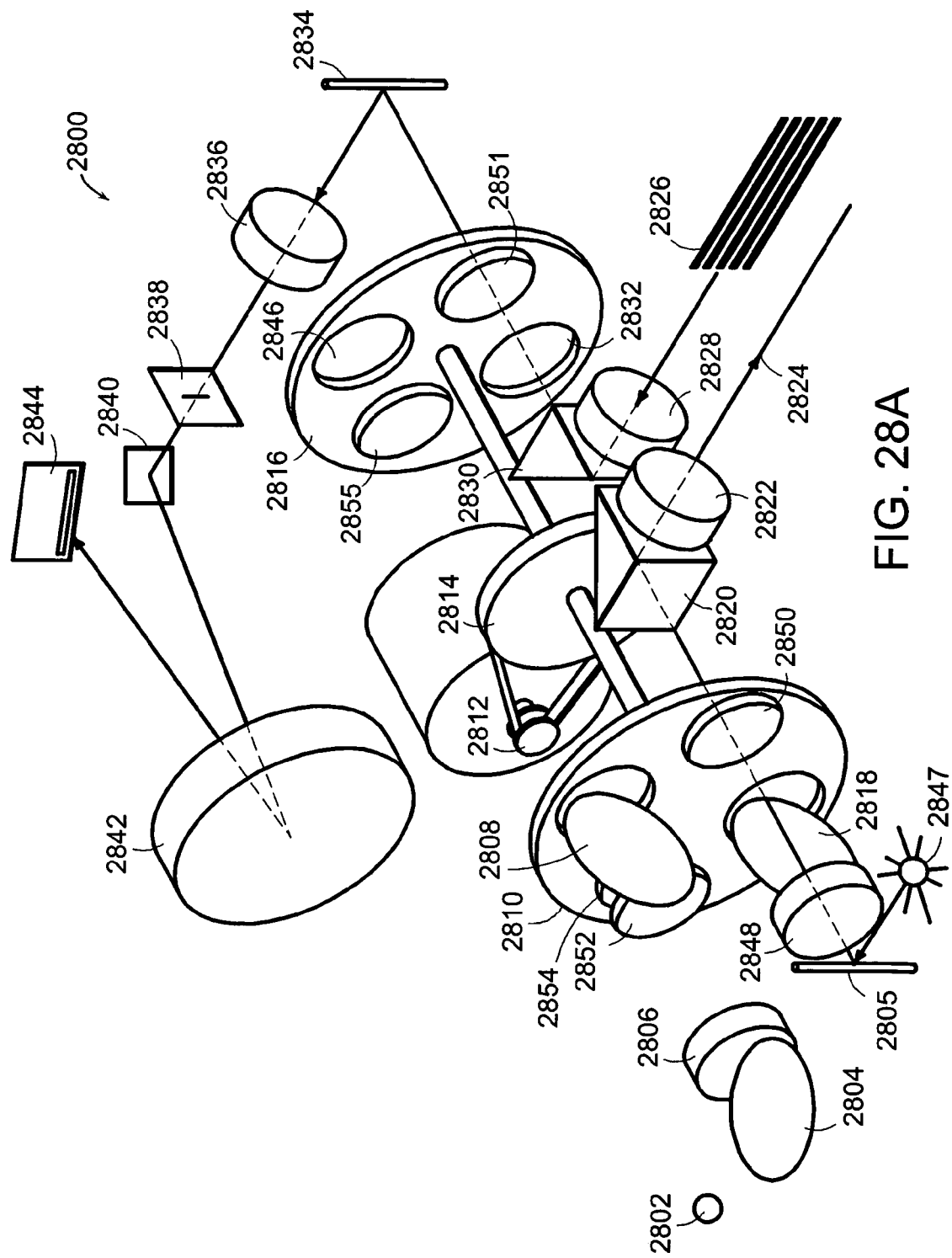
FIGS. 28A-28D are various schematical views of one configuration of a light source and detector system for a light scattering spectroscopic system.
Figure 28B:
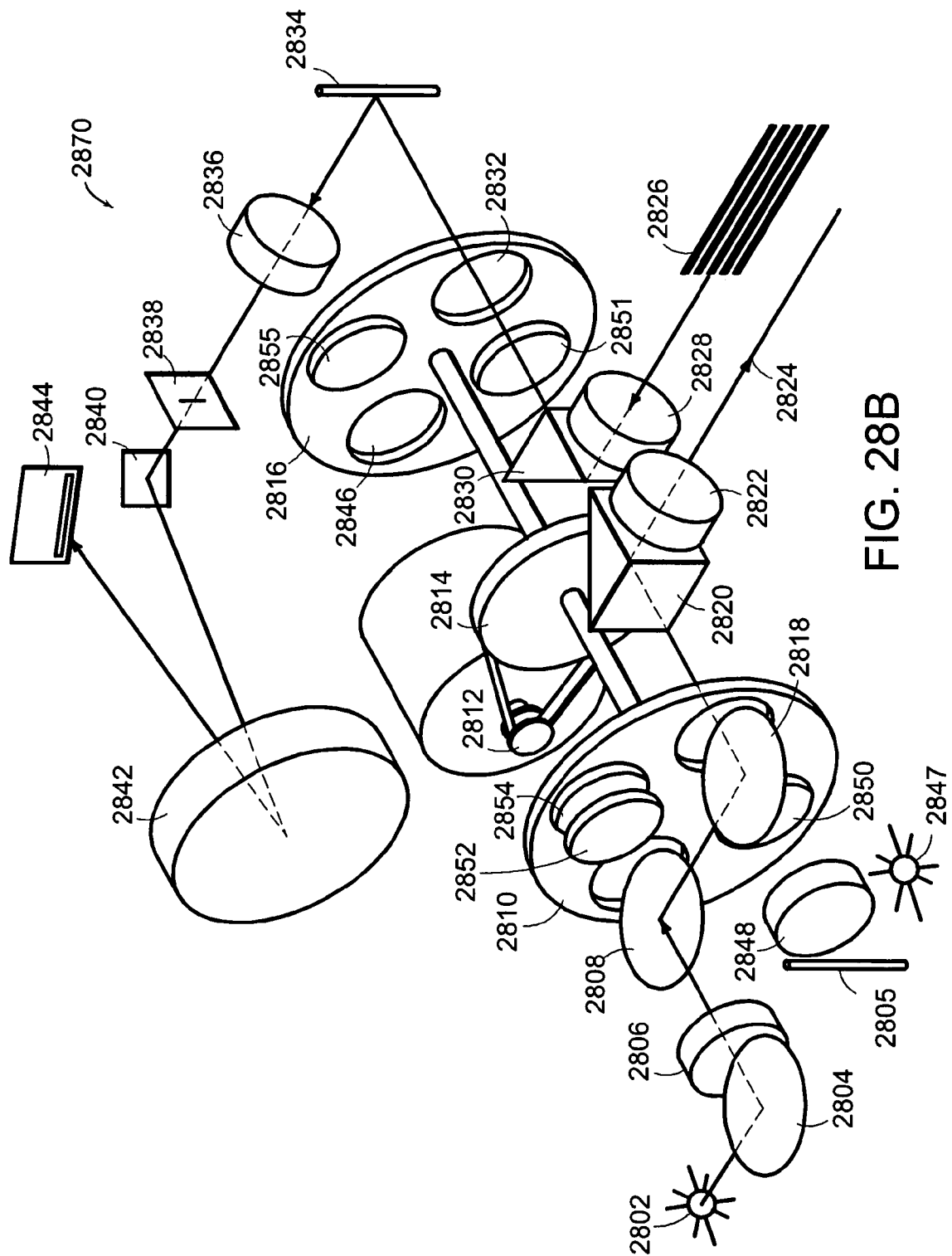
Figure 28C:
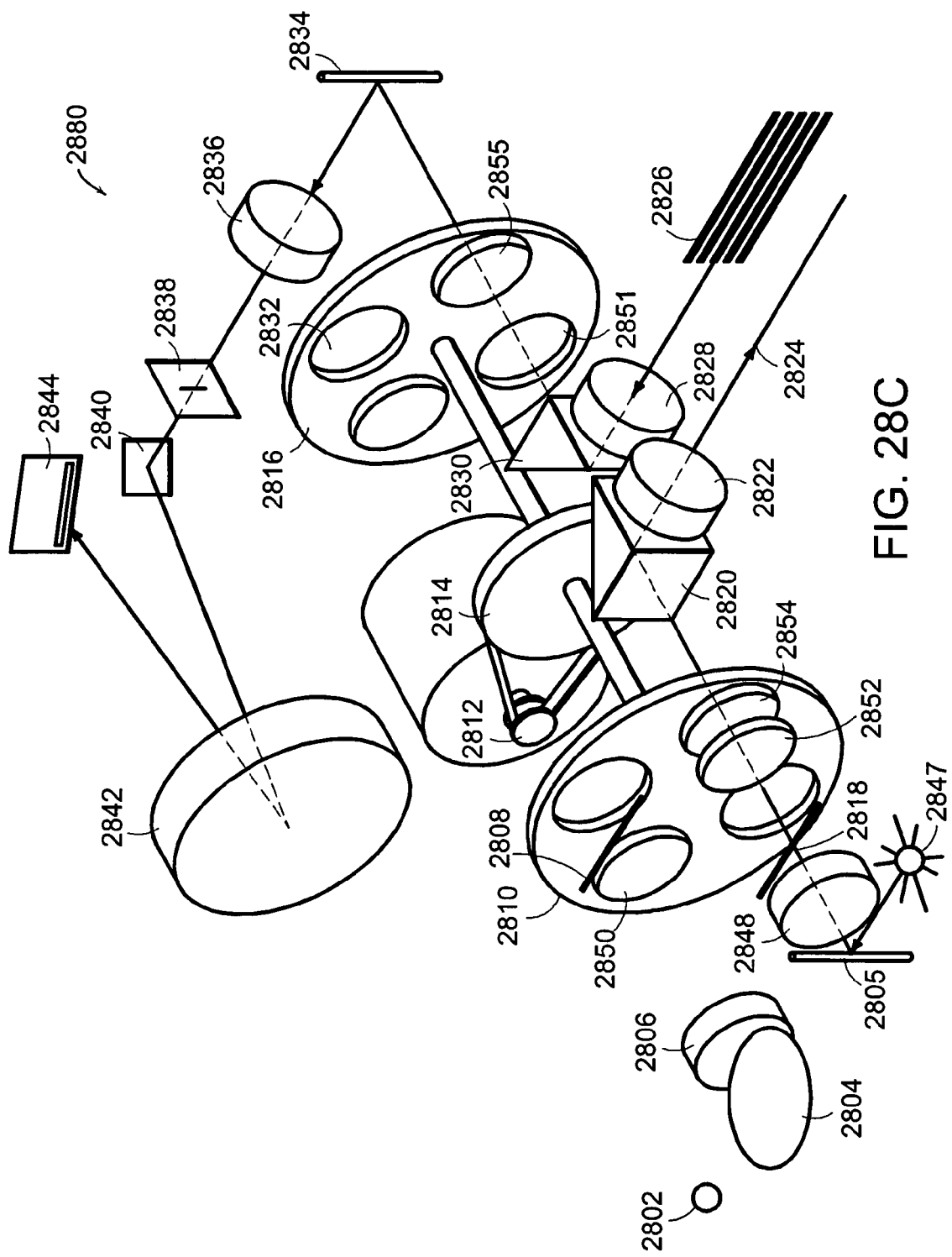
Figure 28D:
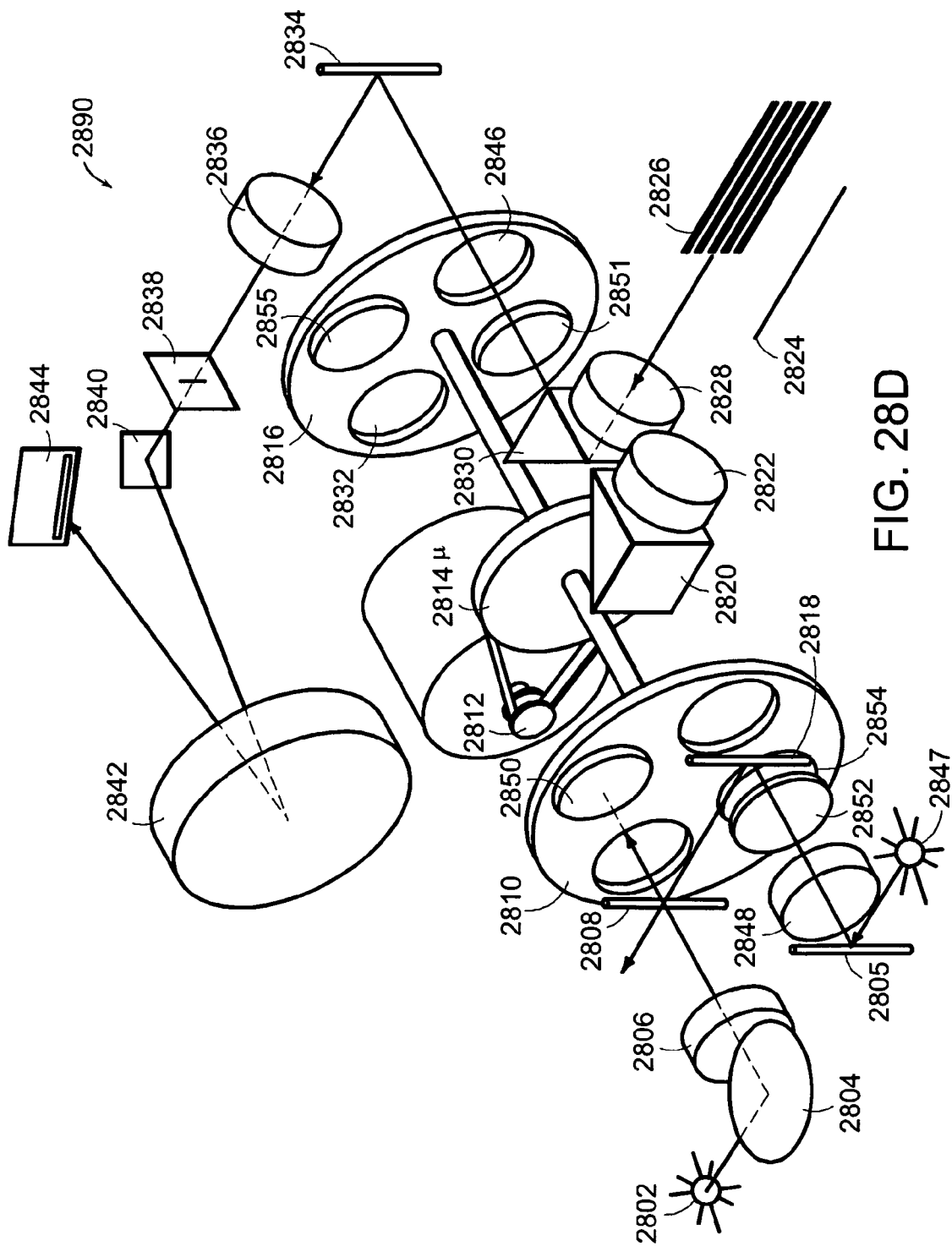
Figure 29:
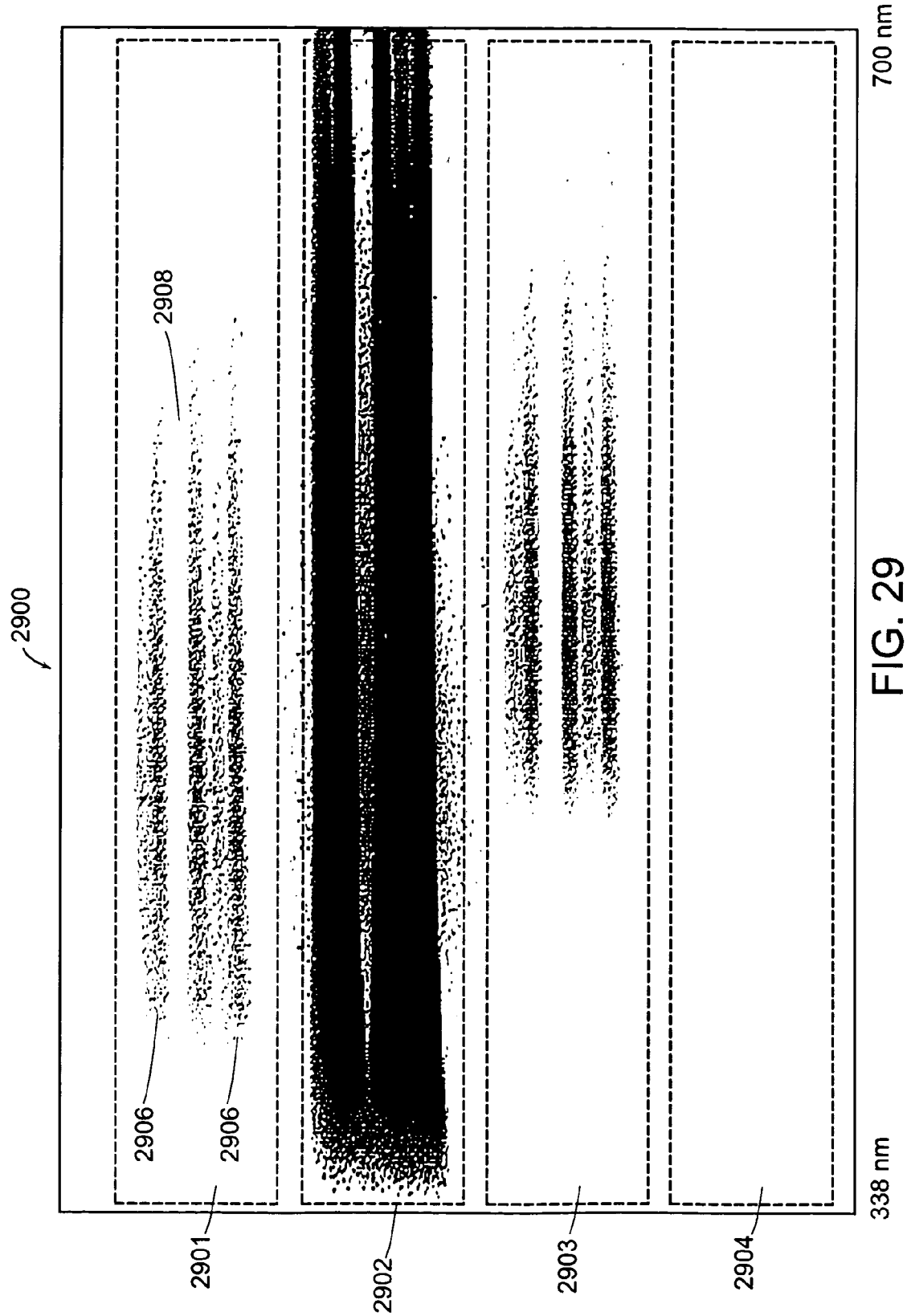
FIG. 29 is a set of spectra measured from a human vermilion border epithelial layer of the lower lip using a system substantially similar to that of FIGS. 28A-D.

FIGS. 28A-D is a sequence of four figures showing one embodiment of the acquisition of data to produce a series of spectra as illustrated in FIG. 29. FIG. 28A shows the system in a first excitation wavelength position 2800. The fluorescence excitation light source 2847 is typically a Hg lamp, but may be any suitable excitation light source, such as for example, a laser. Further, the excitation light source can comprise two lasers (e.g., laser diodes) where, e.g., a first is placed substantially at the position of the illustrated source 2847, and a second behind reflector 2805 (which may be a dichroic reflector).

In another embodiment, the light source comprises a laser diode operating in the red (e.g., from about 630-670 nm) a laser diode operating in the green (e.g. from about 500-550 nm), and a laser diode operating in the violet (e.g. from about 380-460 nm).

In one version, the red, green and violet laser diodes are operated to provide both "white light" to serve as an illumination light source and excitation light. For example, corrected broadband illumination ("white light") can be provided by controlling the intensity and bandwidth of the light that reaches the tissue from each the three laser diodes. Excitation light could, e.g., then be provided by the violet laser diode, by frequency doubling the light from the red laser diode (e.g., with a $KTiOPO_4$ (KTP) crystal), or both, to provide one or more excitation wavelengths.

With the system in the first excitation wavelength position, the light from the fluorescence excitation light source is collimated by lens 2848 and passed preferably through a bandpass filter 2850 in source wheel 2810 to select a particular band of wavelengths for input to the illumination fiber. The precise axial positions of lenses 2848 and 2806 are set so that both the white light and the first excitation light are optimally focused onto the illumination fiber 2824 by lens 2822. With simple achromatic or fused silica lenses, these two conditions use up all of the focusing degrees of freedom. When the wheel system 2810-2816 is turned 90 degrees clockwise from the position of FIG. 28A to the position of FIG. 28B, the light from the "white light" source is passed to the illumination fiber 2824. The wheel system is moved to a desired rotary angle by the stepper (or servo) motor 2812 through the reduction belt drive system 2814. Wheels 2810 and 2816 and the drive pulley 2814 are fixed rigidly to the same shaft so that they stay in rotary phase.

FIG. 28B shows the system in the "white light" position 2870. The "white light" source 2802 is typically a Xe arc lamp but may be any suitable broadband illumination source as described above. The tip and tilt of mirror 2804 is used to adjust the arc position to the optical axis of achromatic collection lens 2806 without having to move the arc itself. The collimated "white light" beam exiting lens 2806 arrives at turning reflector (e.g., a mirror or prism) 2808, attached to wheel 2810, traveling parallel to the rotation axis of the wheel system 2810-2816. Reflector (e.g., a mirror or prism) 2818 is fixed to wheel 2810 so that it is parallel to turning mirror 2808. This condition assures that the beam reflected off of reflector 2818 is also traveling parallel to the rotary axis of the wheel system. The propagation direction of the beam reflected off of the reflector 2818 is invariant to the position of the wheel system (including rotational position) as long as the wheel system and its attached mirrors move as a single rigid body.

The direction of the "white light" beam is then turned by 90 degrees by reflecting prism 2820 onto the optical axis of focusing lens 2822. The end of the illumination fiber for the system 2824 is set at the focus of lens 2822. Since the "white light" entering the lens 2822 is parallel to its optical axis, the light will reach the focus and the end of the illumination fiber 2824. The purpose of this arrangement is so that the "white light" from source 2802 enters the end of the illumination fiber 2824 over an extended rotational angle of the wheel system so that the positioning of the wheel system is not critical to the practical performance of the system.

When the wheel system 2810-2816 is turned 90 degrees clockwise from the position of FIG. 28B to the position of FIG. 28C, the second excitation wavelength position is reached. FIG. 28C shows the system in the second excitation wavelength position 2880. A lens 2852 adjusts the focus of the second excitation wavelength so that it is also optimally focused onto the illumination fiber 2824. This lens may be either positive or negative, for second excitation band wavelengths, which are relatively longer or shorter than the first excitation wavelengths. Preferably, a bandpass filter 2854 sets the wavelengths of the second excitation band.

With a Hg arc lamp source 2847, providing the excitation wavelengths, the system can provide fluorescence excitation power at wavelengths from 300 nm to 420 nm. Wavelengths near prominent mercury lines at 340 nm, 365 nm and 405 nm are most useful if the lamp current is not pulsed. With pulsed current operation the higher blackbody continuum makes all wavelengths in the 300 to 420 nm region usable. With solid-state fluorescence excitation sources at different central wavelengths, the sources can be effectively combined with dichroic mirrors to present a single bright source at the position of source 2847. In this case, the bandpass filters 2850 and 2854 may not be necessary.

When the wheel system 2810-2816 is turned 90 degrees clockwise from the position of FIG. 28C to the position of FIG. 28D, the "no light" position is reached. FIG. 28D shows the system in the "no light" position, no light enters the end of the illumination fiber 2824. The light from the fluorescence excitation light source 2847, in this case, reflects off of reflectors 2808 and 2818 and exits the wheel system on the opposite side where it is dumped. The light from the "white light" source 2802, is reflected off reflector 2808 to the side where it is dumped.

In another embodiment the broadband illumination may be stopped from reaching a spectrometer by a shutter placed in front of the entrance slit to the spectrometer, that is phase locked to a filter wheel so that as the filter wheel turns the shutter opens only during dark read periods of the imaging sensor (e.g., a CCD).

Referring to FIGS. 28A-D, light from the optical probe is returned to the system by collection optical fibers 2826. The proximal ends of the collection fibers 2826 from the fiberoptic probe are preferably arranged vertically in a line to match a vertical slit 2838 of a spectrometer 2840-2844. The spacing of the collection fibers 2826 is exaggerated in the FIGS. 28A-D for clarity. The light received from the probe (e.g., received fluorescence/reflectance light) is collimated by a lens 2828 and turned by a prism 2830 through filter wheel 2816, onto a reflector 2834 that directs light onto lens 2836, which focuses it onto the entrance slit 2838 of the spectrometer.

When the wheel system 2810-2816 is in the first excitation wavelength position (FIG. 28A), a filter blocking that excitation band 2851 in the filter wheel 2816 is in the light path between steering prism 2830 and the reflector 2834 to prevent excitation light from reaching the spectrometer as a first excitation wavelength fluorescence spectrum is obtained by the spectrometer. Similarly, when the wheel system 2810-2816 is in the second excitation wavelength position (FIG. 28C), a blocking filter for the second excitation band 2855 is carried into the receiving path by the rotation of the wheel system. A second excitation wavelength fluorescence spectrum is obtained then by the spectrometer.

The presence of the excitation light blocking filters is important because the fluorescence is typically a thousand times weaker than the excitation light. If reflections of the excitation light from the tissue made it into the spectrometer, they can saturate the CCD pixels, thereby causing defects in the image of the fluorescence spectra.

When the wheel system 2810-2816 is in the "white light" position (FIG. 28B), a clear hole 2832 in filter wheel 2816 allows all of the received light to pass through and a "white light" reflectance spectrum is obtained by the spectrometer. Similarly, when the wheel system 2810-2816 is in the "no light" position (FIG. 28D), a clear hole 2846 in filter wheel 2816 allows all of the received light to pass through to the spectrometer to produce a background spectrum. When both light sources 2804, 2847 are blocked by the reflectors on the source wheel 2810 there is a clear opening 2846 on the filter wheel which allows light from the tissue due to outside illumination (room lights, endoscope illuminators, etc.) to reach the spectrometer. The background spectra taken in this position are preferably subtracted from the other spectra to reduce this source of noise. For example, if the illumination light of the endoscope used to position the fiberoptic probe remains on during the measurements, the spectrum of external light transmitted through the tissue to the tip of the fiber optic probe can be measured in the "no light" configuration.

Inside the spectrometer a reflector 2840 directs the expanding beam of light to a holographic/focusing grating 2842 which reimages the slit onto a CCD camera 2844 with wavelength dispersion. Preferably, the first spectrum is imaged onto the bottom of the CCD 2844 so that successive shifts of the CCD pixels towards the read register serve as a storage mechanism for the obtained spectra, such as, e.g.,: (1) first excitation wavelength fluorescence; (2) "white light" reflectance; (3) second excitation wavelength fluorescence; and (4) background light. FIG. 29 shows a set of such spectra measured from a human vermilion border epithelial layer of the lower lip using a system substantially similar to that of FIGS. 28A-D.

FIG. 29 illustrates spectra of human vermilion border epithelial tissue (the red portion of the lip) obtained with a light scattering spectroscopy system substantially similar to FIGS. 28A-D where the excitation light source comprised a Hg arc lamp and the illumination source a Xe arc lamp. The display 2900 schematically shows photoelectron generation by CCD pixels, where increased darkness (e.g., black dots) indicate increased photoelectron generation. The vertical axis of the display 2900 indicates the order of spectra acquisition. For example, the first spectrum 2901 is imaged onto the bottom of the CCD, the pixels of the first spectrum are then shifted towards the read register and a second spectrum 2902 is obtained. This shift appears as a vertical displacement upward of the first spectrum 2901 in the display 2900. The shifting and acquisition of spectra continues to obtain a third spectrum 2903 and a fourth spectrum 2904. This shifting causes the first spectrum 2901 to appear at the top of the display and the fourth spectrum 2904 at the bottom when all four spectra are displayed together. The horizontal axis of the display 2900 is representative of the wavelength of light striking the CCD camera due to the dispersion of the light by the holographic/focusing grating.

The first spectrum 2901 is a first excitation wavelength fluorescence spectrum for a first excitation wavelength band centered at 340 nm obtained with a system configuration substantially similar to that of FIG. 28A. The first spectrum 2901 was obtained through a 340 nm blocking filter (long pass filter) in the filer wheel and with a 100 ms CCD camera exposure. The "tracks" 2906 in the spectra 2901-2904 represent light from collection optical fibers returned and passed to the spectrometer. The "gap" 2908 in the spectra 2901-2904 is due to a broken collection optical fiber.

The second spectrum 2902 is a "white light" reflectance spectrum obtained with a system configuration substantially similar to that of FIG. 28B with a 6 ms CCD camera exposure. The shorted exposure time during acquisition of the reflectance spectrum facilitates avoiding saturation of the CCD camera and improves the duty cycle for obtaining multiple spectra sets.

The third spectrum 2903 is a second excitation wavelength fluorescence spectrum for a second excitation wavelength band centered at 405 nm obtained with a system configuration substantially similar to that of FIG. 28C. The third spectrum 2903 was obtained through a 405 nm blocking filter (long pass filter) in the filer wheel and with a 100 ms CCD camera exposure. The fourth spectrum 2904 is a background spectra obtained with a system configuration substantially similar to that of FIG. 28D with a 100 ms CCD camera exposure. In a preferred embodiment, the total acquisition time for the four spectra is approximately one second.

In one embodiment, where endoscope illumination remains on the tissue during fluorescence spectra acquisition, the "background" spectrum is substrated from the combined fluorescence and background spectra to obtain a corrected fluorescence spectra without the endoscope illumination. This method adds noise to the corrected fluorescence spectra even if the background spectra could be perfectly subtracted because shot noise on the background is uncorrelated with the shot noise on the fluorescence.

The imaging sensor of the detector system, for example, a CCD, CMOS imaging device or other imaging sensor, generates an electronic representation of the spectrum imaged onto the sensor. A CCD, for example, can provide the ability to detect, store and display multiple frames of data (e.g., sequential spectrums) to achieve a real-time visualization of the imaged light and, hence, the tissue imaged. In one embodiment, a CCD stores each sequential spectrum as the illumination and collection paths are switched open. The acquired spectra are read-out at one time as a spectral "image" using standard CCD read-out electronics. In some embodiments, a plurality of detector elements (pixels) can be grouped or binned to provide desired resolutions, e.g., in acquisition of fluorescence spectra. In other embodiments, the CCD has sufficient dynamic range, with respect to read-out speed, to reduce or eliminate binning.

In addition, in preferred embodiments of the systems of the present invention, the detector system includes a frame grabber to acquire images, e.g., of the tissue under investigation as provided by an endoscope, the imaging sensor, or both. Preferably, images are acquired for every reference location in a tissue investigation to provide, for example, information on the location on a tissue from which spectra are obtained.

Preferably, the spectral output of the light source is measured and the spectral sensitivity of the detector system calibrated. In one embodiment, the spectral output of the light source for, e.g., the corrected broadband illumination ("white light") and excitation light, is measured by using the output of the illumination fiber, or fibers, as the input to the detector system. For example, referring to FIGS. 28A-D, the distal end of the illumination optical fiber 2824, instead of the collection optical fibers 2826, is used as the input into the lens 2828 to measure the spectral output of the light source in each of the four acquisition positions 2800, 2870, 2880, 2890. In one embodiment, the detector system is calibrated by providing a reference light source and determining a correction factor for the detector system, which may vary with wavelength, based on a comparison of the reference light source output with the detector system response. An example of one embodiment of detector system calibration is illustrated in FIGS. 30A-D for a system substantially similar to that of FIGS. 28A-D.

Figure 30B:
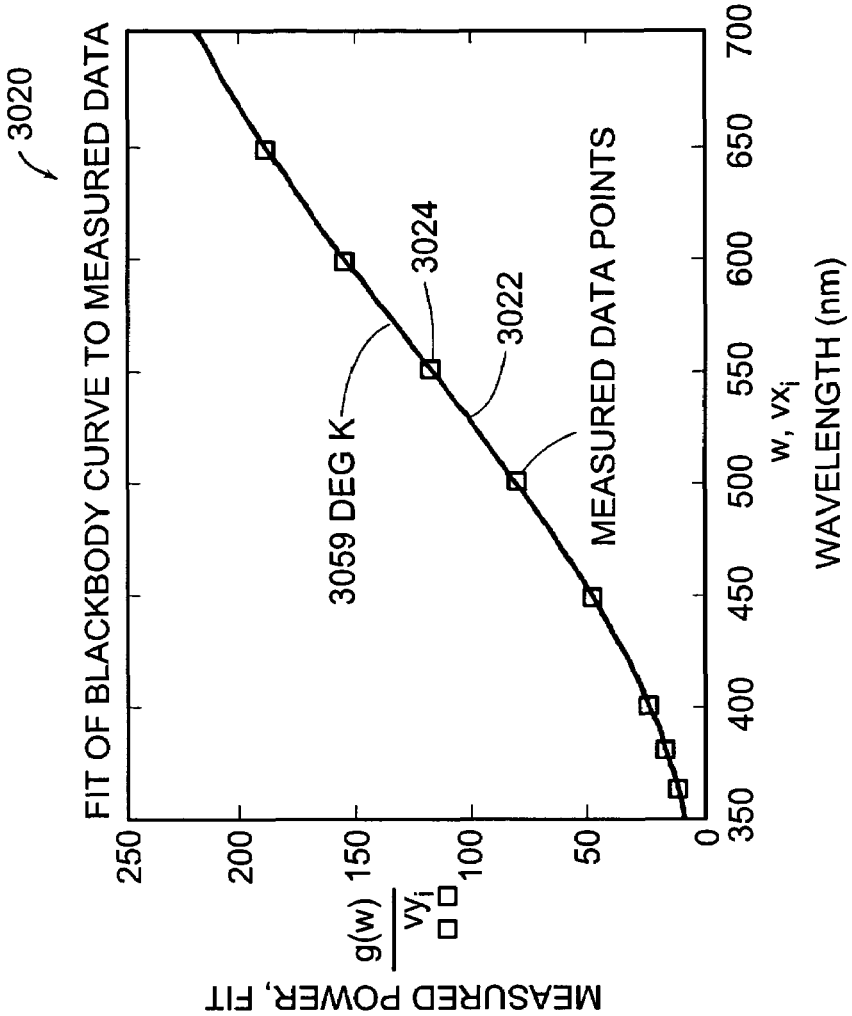
FIGS. 30A-D illustrate the calibration of a detector system in a system substantially similar to that of FIGS. 28A-D.
Figure 30A:
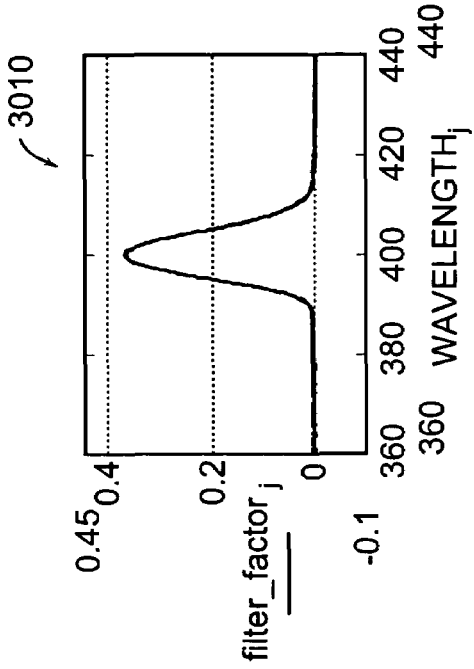
Figure 30D:
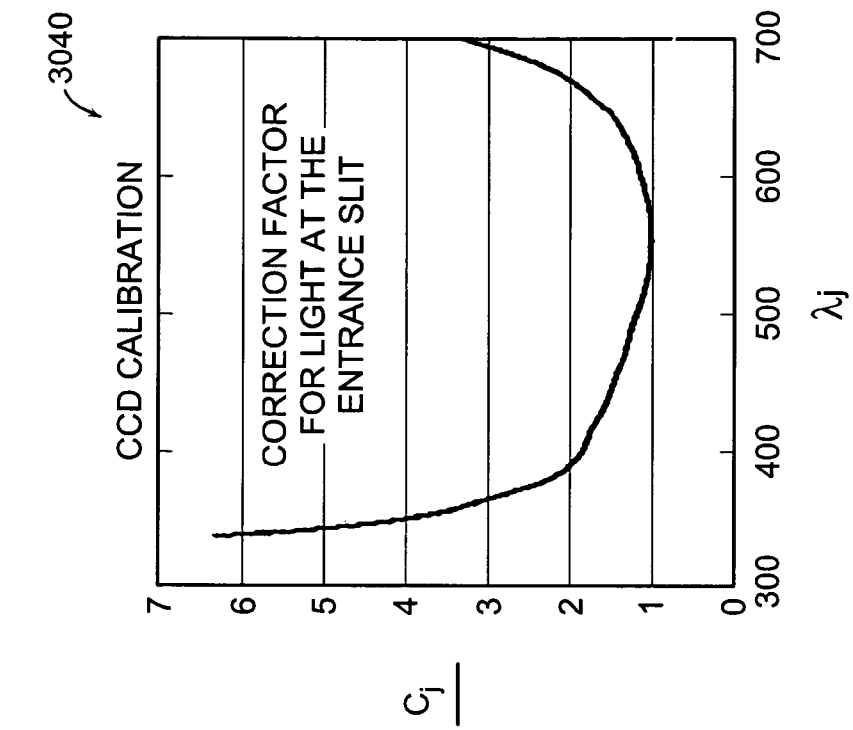
Figure 30C:
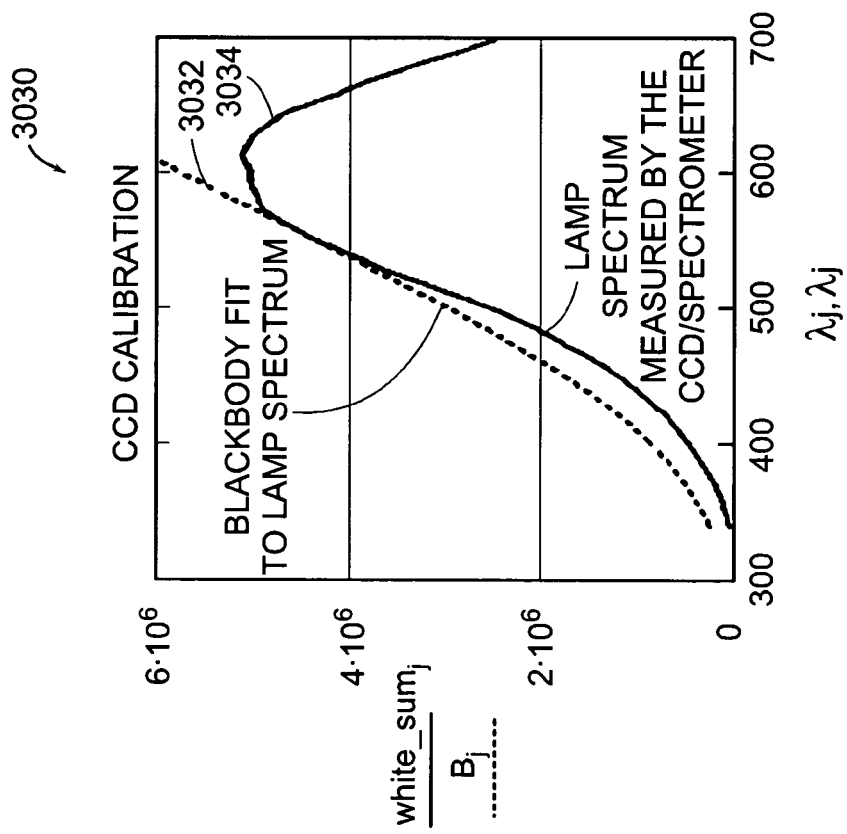

Referring to FIGS. 30A-D, in one embodiment, a 6V Ushio "3200 Kelvin" tungsten lamp was used as a reference source. The tungsten lamp's spectrum was measured with a calibrated photodiode and narrowband filters. The transmission curve of a narrowband filter 3010, centered approximately at 400 nm, is shown in FIG. 30A. The measured data is plotted as a power vs. wavelength curve 3020 to determine the actual tungsten lamp temperature as illustrated in FIG. 30B, where the solid line 3022 is the fit of a blackbody radiation curve to the measured data (unfilled squares) 3024. The fit yielding a tungsten lamp blackbody temperature of 3059 Kelvin. Dividing the calibrated lamp spectrum by the spectrum as measured by the CCD yields a correction factor. FIG. 30C shows CCD response as a function of wavelength 3030 where the blackbody fit to the tungsten lamp spectrum 3032 (dashed line) has been superimposed on the tungsten lamp spectrum as measured by the CCD 3034 (solid line). FIG. 30D shows the resultant CCD calibration as a correction curve 3040, which provides a correction factor (x-axis) as a function of wavelength (y-axis) for the detector system.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, in other embodiments in hardware or firmware implementations may alternatively be used, and vice-versa.

Referring back to FIG. 27, a controller 2794 is electrically coupled to the imaging sensor or detector 2775 or a detector coupled to the spectrometer 2703. Further, a processing unit, such as a data processor 2790 capable of executing analysis programs for processing the acquired spectra, and determining particle size distribution is coupled to the spectrometer. An image display 2792 can be coupled to the processor. Although illustrated with respect to FIG. 27, the controller, processor and display units can be coupled to any of the illustrated embodiments.

In some embodiments, the data processor may implement an analysis program and/or functionality of the methods of the present invention as software on a general purpose computer. In addition, such a program may set aside portions of a computer's random access memory to provide control logic that affects the analysis program, light source control, detector systems spectra acquisition, and the operations with and on the measured spectra. In such an embodiment, the program may be written in any one of a number of high-level languages, such as FORTRAN, PASCAL, C, C++, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, computer usable medium such as a hard drive device, a CD-ROM, a DVD-ROM, or a computer diskette, having computer readable program code segments stored thereon.

It will be apparent to those of ordinary skill in the art that methods involved in the system and method for light scattering spectroscopy may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

What is claimed:

1. A light scattering spectroscopic system comprising:
an optical probe comprising;
an illumination optical fiber extending along a probe central axis;
a plurality of collection optical fibers tilted at different collection angles relative to the probe central axis, the collection optical fibers being held at the different collection angles by a tapered retainer in the probe, such that the optical probe illuminates and collects light from overlapping areas; and
a polarizer that is optically coupled to at least one collection optical fiber;
a light source optically coupled to the illumination optical fiber;
a detector system optically coupled to the first collection optical fiber and the second collection optical fiber, the detector system generating a spectrum from light transmitted by at least one of the first collection fiber and the second collection fiber to the detector system; and
a data processor in communication with the detector system.

2. The system of claim 1, wherein the optical probe further comprises a plurality of illumination optical fibers optically coupled to the light source.

3. The system of claim 2, wherein the illumination optical fibers are coupled to a broadband light source to transmit broadband illumination in a range from about 300 nm to about 460 nm.

4. The system of claim 1, wherein a first illumination optical fiber transmits a first wavelength of light from the light source in a range from about 300 nm to about 460 nm; and
a second illumination optical fiber optically coupled to the light source that transmits a second wavelength of light in a range from about 300 nm to about 460 nm, the second wavelength of light being different from the first wavelength of light.

5. The system of claim 1, wherein light collected in response to a first wavelength of light in a range from about 300 nm to about 460 nm and light collected in response. to a second wavelength of light in a range from about 300 nm to about 460 nm, the second wavelength of light being different from the first wavelength of light, the first wavelength of light and the second wavelength of light being collected through separate collection optical fibers.

6. The system of claim 1, wherein the optical probe further comprises a plurality of collection optical fibers that couple polarized light to the detector system.

7. The system of claim 6, wherein the plurality of light collection optical fibers are coupled to the polarizer to transmit polarized light in the wavelength range from about 335 nm to about 700 nm.

8. The system of claim 1, wherein the optical probe further comprises a second polarizer.

9. The system of claim 8, wherein the optical probe comprises at least two polarizers, wherein a polarization axis of one polarizer is substantially orthogonal to a polarization axis of another polarizer.

10. The system of claim 1, wherein the collection optical fibers have a proximal end optically coupled to the detector system and a distal end that is optically coupled to one or more polarizers.

11. The system of claim 1, wherein the light source comprises a mercury lamp.

12. The system of claim 1, wherein the light source comprises a xenon lamp.

13. The system of claim 1, wherein the light source comprises one or more laser diodes.

14. The system of claim 13, wherein the light source comprises:
a first laser diode emitting light having a wavelength in the range from about 380 nm to about 460 nm; and
a second laser diode emitting light having a wavelength in the range from about 630 nm to about 670 nm.

15. The system of claim 14, further comprising a third laser diode emitting light having a wavelength in the range from about 500 nm to about 550 nm.

16. The system of claim 1, wherein the detector system comprises a charge, coupled device.

17. The system of claim 1, wherein the detector system comprises a holographic grating.

18. The system of claim 1, wherein the detector system comprises a phase locked shutter.

19. The system of claim 1, wherein the data processor stores instructions to determine a particle characteristic based at least in part on one or more spectra generated by the detector system.

20. The system of claim 19, wherein the particle characteristic is a particle size distribution.

21. The system of claim 1, wherein the data processor stores instructions to subtract a spectrum acquired from a collection optical fiber oriented to collect light polarized parallel to a plane of polarization of the illumination light from a spectrum acquired from a collection optical fiber oriented to collect light polarized perpendicular to the plane of polarization of the illumination light.

22. The system of claim 1 wherein the detector system comprises a pixellated image sensor.

23. The system of claim 1 wherein the data processor determines a periodic component of detected light as a function of wavelength to determine a physical characteristic of tissue illuminated with the illumination fiber.

24. The system of claim 1 wherein the detector detects one or more of a light scattering spectrum, a reflectance spectrum and a fluorescence spectrum.

25. The system of claim 1 wherein the processor determines a cell nuclear size distribution within the tissue.

26. The system of claim 1 further comprising a filter wheel that filters light coupled to an optical fiber.

27. The system of claim 1 further comprising a shutter that controls coupling of light from the collection fibers to the detector system.

28. The system of claim 1 further comprising a plurality of fluorescence collecting fibers and a reflectance collecting fiber.

29. The system of claim 1 wherein the data processor processes a first collected polarization component and a second collected polarization component to obtain a difference spectrum.

30. The system of claim 1 further comprising a retainer holding the collection fibers at a plurality of tapered angles relative to the illumination fiber.

31. The system of claim 1 wherein the processor determines a frequency spectrum with a Fourier transform.

32. The system of claim 1 wherein the light source comprises a first emitter emitting a first frequency, a second emitter emitting at a second frequency and a third emitter at a third frequency such that the emitters can operate as a white light source.

33. The system of claim 1 wherein the light source includes a calibration light source.

34. The system of claim 1 wherein the data processor determines normal from dysplastic or cancerous tissue.

35. The system of claim 2 further comprising an imaging detector at a distal end of the probe and a fluorescence spectrometer that is optically coupled to a distal end of the probe with an additional optical fiber or fiber bundle.

36. The system of claim 35 wherein the light source comprises a first laser diode, a second laser diode and a white light source.

37. The system of claim 35 further comprising a bifurcated illumination fiber bundle.

38. The system of claim 1 further comprising a first filter wheel on an illumination optical path and a second filter wheel on a collection optical path, the first wheel and second wheel being controlled by an actuator.

39. The system of claim 1 wherein the polarizer comprises one or more thin films positioned between a polished fiber retainer surface and a distal window.

* * * * *